United States Patent
Peng et al.

(10) Patent No.: US 10,806,798 B2
(45) Date of Patent: Oct. 20, 2020

(54) COMPOUND WITH EFFECTS OF THROMBOLYSIS, FREE RADICAL SCAVENGING AND THROMBUS-TARGETING

(71) Applicant: Shanghai Lumosa Therapeutics Co., Ltd., Shanghai (CN)

(72) Inventors: Shiqi Peng, Beijing (CN); Ming Zhao, Beijing (CN); Xueyun Jiang, Beijing (CN)

(73) Assignee: Shanghai Lumosa Therapeutics Co., Ltd., Shanghai (CN)

( * ) Notice: Subject to any disclaimer, the term of this patent is extended or adjusted under 35 U.S.C. 154(b) by 206 days.

(21) Appl. No.: 15/991,297

(22) Filed: May 29, 2018

(65) Prior Publication Data

US 2018/0264126 A1    Sep. 20, 2018

Related U.S. Application Data

(63) Continuation of application No. 14/425,909, filed as application No. PCT/CN2013/072731 on Mar. 15, 2013, now abandoned.

(30) Foreign Application Priority Data

| Sep. 5, 2012 | (CN) | ............ 2012 1 0323848 |
| Sep. 5, 2012 | (CN) | ............ 2012 1 0323849 |
| Sep. 5, 2012 | (CN) | ............ 2012 1 0323850 |
| Sep. 5, 2012 | (CN) | ............ 2012 1 0323951 |
| Mar. 5, 2013 | (CN) | ............ 2013 1 0068532 |

(51) Int. Cl.

| A61K 47/64 | (2017.01) |
| C07K 7/06 | (2006.01) |
| C07K 5/09 | (2006.01) |
| C07K 5/083 | (2006.01) |
| A61K 38/06 | (2006.01) |
| A61K 38/07 | (2006.01) |
| A61K 47/69 | (2017.01) |
| A61K 38/00 | (2006.01) |
| C07K 5/097 | (2006.01) |
| A61K 31/4164 | (2006.01) |
| A61K 38/08 | (2019.01) |
| A61K 47/54 | (2017.01) |

(52) U.S. Cl.
CPC .......... *A61K 47/64* (2017.08); *A61K 31/4164* (2013.01); *A61K 38/06* (2013.01); *A61K 38/07* (2013.01); *A61K 38/08* (2013.01); *A61K 47/542* (2017.08); *A61K 47/6929* (2017.08); *C07K 5/0806* (2013.01); *C07K 5/0815* (2013.01); *C07K 5/0821* (2013.01); *C07K 7/06* (2013.01); *A61K 38/00* (2013.01)

(58) Field of Classification Search
CPC .... A61K 31/4164; A61K 38/00; A61K 38/06; A61K 38/07; A61K 38/08; A61K 47/542; A61K 47/64; A61K 47/6929; A61P 17/00; A61P 19/02; A61P 25/00; A61P 25/18; A61P 25/28; A61P 29/00; A61P 35/00; A61P 35/02; A61P 39/06; A61P 3/10; A61P 7/02; A61P 7/12; A61P 9/00; A61P 9/10; C07K 5/0806; C07K 5/0815; C07K 5/0821; C07K 7/06
USPC .......................................... 424/489; 530/328
See application file for complete search history.

(56) References Cited

FOREIGN PATENT DOCUMENTS

| CN | 1146458 A | 4/1997 |
| CN | 1490328 A | 4/2004 |
| CN | 1490329 A | 4/2004 |
| CN | 1743314 A | 3/2006 |
| CN | 1743315 A | 3/2006 |
| CN | 1743316 A | 3/2006 |
| CN | 1978462 A | 6/2007 |
| CN | 101085806 A | 12/2007 |
| CN | 101190941 A | 4/2008 |
| CN | 101190940 A | 6/2008 |
| CN | 101318993 A | 12/2008 |
| CN | 101591376 A | 12/2009 |
| CN | 102120757 A | 7/2011 |
| CN | 102477072 A | 5/2012 |
| CN | 102477075 A | 5/2012 |
| CN | 102477076 A | 5/2012 |
| CN | 102485746 A | 6/2012 |
| CN | 102485747 A | 6/2012 |
| CN | 102485748 A | 6/2012 |
| CN | 102796046 A | 11/2012 |
| CN | 102807604 A | 12/2012 |
| CN | 102807605 A | 12/2012 |
| CN | 102875644 A | 1/2013 |

(Continued)

OTHER PUBLICATIONS

English Translation of CN1978462 B, published Apr. 21, 2010, Peng Shiqi.

(Continued)

*Primary Examiner* — James H Alstrum-Acevedo
*Assistant Examiner* — Erinne R Dabkowski
(74) *Attorney, Agent, or Firm* — Perkins Coie LLP; Viola Kung

(57) ABSTRACT

The present invention discloses a novel compound with effects of thrombolysis, free radical scavenging and thrombus-targeting, as well as a preparation method and use thereof. The compound is a ternary conjugate formed by conjugating a thrombolytic peptide, a free radical scavenger and a thrombus-targeting/antithrombotic peptide together via a linking arm. The present invention also discloses a pharmaceutical composition containing the compounds, wherein the compounds form a nanospherical structure.

6 Claims, 28 Drawing Sheets

Specification includes a Sequence Listing.

(56) References Cited

FOREIGN PATENT DOCUMENTS

| | | |
|---|---|---|
| CN | 102887941 A | 1/2013 |
| CN | 102898505 A | 1/2013 |
| CN | 102898506 A | 1/2013 |
| CN | 102898507 A | 1/2013 |
| CN | 103159835 A | 6/2013 |
| RU | 2214416 C2 | 10/2003 |
| WO | 9407918 A1 | 4/1994 |

OTHER PUBLICATIONS

Guijuan et al., "Synthesis, Free Radical Scavenging and Thrombolytic Activities of Nitronyl Nitroxide Modified Peptide 6A and Analogues," Journal of Capital University of Medical Sciences. 26(1):42 (2005). English abstract provided.
International Search Report for PCT/CN2013/072731, dated Jun. 24, 2013 (10 pages).
Sarabjeet Singh Suri, Nanotechnology-based drug delivery systems, Journal of Occupational Medicine and Toxicology, 2007, 2:16.
Wang et al., "The Antithrombotic Effects of P6A and its Derivatives," Journal of Chinese Pharmaceutical Sciences. 5 (4):174-6 (1996).
Yisong, Zhao, Journal of Capital Medical University, Feb. 2008, vol. 29 No. 1. English Translation using google translation.
Zhang et al., "A class of novel nitronyl nitroxide labeling basic and acidic amino acids: Synthesis, application for preparing ESR optionally labeling peptides, and bioactivity investigations," Bioorganic & Medicinal Chemistry. 16(7):4019-28 (2008).
Zhao et al., "Targeting Thrombolytic Oligopeptide," Chemical Biology and Pharmaceutical Laboratory, School of Chemical Biology and Pharmaceutical Sciences, Capital Medical University, Journal of Capital Medical University, 29 (1): 103-105 (2008).

$1 \times 10^{-6}$M  $1 \times 10^{-9}$M  $1 \times 10^{-12}$M $1 \times 10^{-6}$M  $1 \times 10^{-9}$M  $1 \times 10^{-12}$M $1 \times 10^{-6}$M  $1 \times 10^{-9}$M  $1 \times 10^{-12}$M $1 \times 10^{-6}$M  $1 \times 10^{-9}$M  $1 \times 10^{-12}$M

1 × 10⁻⁶M        1 × 10⁻⁹M        1 × 10⁻¹²M

1 × 10⁻⁶M        1 × 10⁻⁹M        1 × 10⁻¹²M

1 × 10⁻⁶M        1 × 10⁻⁹M        1 × 10⁻¹²M

1 × 10⁻⁶M        1 × 10⁻⁹M        1 × 10⁻¹²M $1 \times 10^{-6}M$     $1 \times 10^{-9}M$     $1 \times 10^{-12}M$ $1 \times 10^{-6}M$     $1 \times 10^{-9}M$     $1 \times 10^{-12}M$ $1 \times 10^{-6}M$     $1 \times 10^{-9}M$     $1 \times 10^{-12}M$ $1 \times 10^{-6}M$     $1 \times 10^{-9}M$     $1 \times 10^{-12}M$

SEQUENCE LISTING

```
<160> NUMBER OF SEQ ID NOS: 35

<210> SEQ ID NO 1
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 1

Lys Arg Gly Asp Val
1               5

<210> SEQ ID NO 2
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 2

Lys Arg Gly Asp Phe
1               5

<210> SEQ ID NO 3
<211> LENGTH: 4
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 3

Arg Pro Ala Lys
1

<210> SEQ ID NO 4
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 4

Ala Arg Pro Ala Lys
1               5

<210> SEQ ID NO 5
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 5

Gly Arg Pro Ala Lys
1               5

<210> SEQ ID NO 6
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 6

Gln Arg Pro Ala Lys
1               5

<210> SEQ ID NO 7
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 7

Lys Pro Ala Lys
1

<210> SEQ ID NO 8
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 8

Pro Ala Lys Pro
1

<210> SEQ ID NO 9
<211> LENGTH: 5
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 9

Ala Lys Pro Ala Lys
1               5

<210> SEQ ID NO 10
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 10

Pro Ala Lys Pro Ala
1               5

<210> SEQ ID NO 11
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 11

Arg Gly Asp Ser
1

<210> SEQ ID NO 12
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 12

Arg Gly Asp Val
1

<210> SEQ ID NO 13
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 13

Arg Gly Asp Phe
1

<210> SEQ ID NO 14
<211> LENGTH: 4
<212> TYPE: PRT
<213> ORGANISM: ARTIFICIAL SEQUENCE
<220> FEATURE:
<223> OTHER INFORMATION: SYNTHESIZED

<400> SEQUENCE: 14

Tyr Ile Gly Ser
1

<210> SEQ ID NO 15
<211> LENGTH: 9
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 15

Tyr Ile Gly Ser Arg Arg Gly Asp Ser
1               5

<210> SEQ ID NO 16
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 16

Tyr Ile Gly Ser Arg Arg Gly Asp Val
1               5

<210> SEQ ID NO 17
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 17

Tyr Ile Gly Ser Arg Arg Gly Asp Phe
1               5

<210> SEQ ID NO 18
<211> LENGTH: 10
<212> TYPE: PRT
<213> ORGANISM: ARTIFICIAL SEQUENCE
<220> FEATURE:
<223> OTHER INFORMATION: SYNTHESIZED

<400> SEQUENCE: 18

Tyr Ile Gly Ser Arg Tyr Ile Gly Ser Lys
1               5                   10

<210> SEQ ID NO 19
<211> LENGTH: 10
<212> TYPE: PRT
<213> ORGANISM: ARTIFICIAL SEQUENCE
<220> FEATURE:
<223> OTHER INFORMATION: SYNTHESIZED

<400> SEQUENCE: 19

Tyr Ile Gly Ser Arg Tyr Ile Gly Ser Arg
1               5                   10

<210> SEQ ID NO 20
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 20

Tyr Ile Gly Ser Lys Arg Gly Asp Ser
1               5

<210> SEQ ID NO 21
<211> LENGTH: 9
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 21

Tyr Ile Gly Ser Lys Arg Gly Asp Phe
1               5

<210> SEQ ID NO 22
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 22

Tyr Ile Gly Ser Lys Arg Gly Asp Val
1               5

<210> SEQ ID NO 23
<211> LENGTH: 10
<212> TYPE: PRT
<213> ORGANISM: ARTIFICIAL SEQUENCE
<220> FEATURE:
<223> OTHER INFORMATION: SYNTHESIZED

<400> SEQUENCE: 23

Tyr Ile Gly Ser Lys Tyr Ile Gly Ser Lys
1               5                   10

<210> SEQ ID NO 24
<211> LENGTH: 10
<212> TYPE: PRT
<213> ORGANISM: ARTIFICIAL SEQUENCE
<220> FEATURE:
<223> OTHER INFORMATION: SYNTHESIZED

<400> SEQUENCE: 24

Tyr Ile Gly Ser Lys Tyr Ile Gly Ser Arg
1               5                   10

<210> SEQ ID NO 25
<211> LENGTH: 8
<212> TYPE: PRT
<213> ORGANISM: ARTIFICIAL SEQUENCE
<220> FEATURE:
<223> OTHER INFORMATION: SYNTHESIZED

<400> SEQUENCE: 25

Arg Gly Asp Ser Arg Gly Asp Ser
1               5

<210> SEQ ID NO 26
<211> LENGTH: 8
<212> TYPE: PRT
<213> ORGANISM: ARTIFICIAL SEQUENCE
<220> FEATURE:
<223> OTHER INFORMATION: SYNTHESIZED

<400> SEQUENCE: 26

Arg Gly Asp Val Arg Gly Asp Val
1               5

<210> SEQ ID NO 27
<211> LENGTH: 8
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 27

Arg Gly Asp Phe Arg Gly Asp Phe
1               5

<210> SEQ ID NO 28
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 28

Arg Gly Asp Ser Tyr Ile Gly Ser Arg
1               5

<210> SEQ ID NO 29
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 29

Arg Gly Asp Ser Tyr Ile Gly Ser Lys
1               5

<210> SEQ ID NO 30
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 30

Arg Gly Asp Val Tyr Ile Gly Ser Arg
1               5

<210> SEQ ID NO 31
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 31

Arg Gly Asp Val Tyr Ile Gly Ser Lys
1               5

<210> SEQ ID NO 32
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 32

Arg Gly Asp Phe Tyr Ile Gly Ser Arg
1               5

<210> SEQ ID NO 33
<211> LENGTH: 9
<212> TYPE: PRT
<213> ORGANISM: ARTIFICIAL SEQUENCE
```

```
<220> FEATURE:
<223> OTHER INFORMATION: SYNTHESIZED

<400> SEQUENCE: 33

Arg Gly Asp Phe Tyr Ile Gly Ser Lys
1               5

<210> SEQ ID NO 34
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 34

Lys Ala Pro Arg Ala
1               5

<210> SEQ ID NO 35
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 35

Lys Ala Pro Arg Gly
1               5
```

COMPOUND WITH EFFECTS OF THROMBOLYSIS, FREE RADICAL SCAVENGING AND THROMBUS-TARGETING

CROSS-REFERENCE TO RELATED APPLICATIONS

This application is continuation of U.S. application Ser. No. 14/425,909, filed Apr. 17, 2015; which is the US National Stage of PCT/CN2013/072731, filed Mar. 15, 2013; which claims priority to Chinese Patent Application No. 201310068532.4, filed Mar. 5, 2013, and Chinese Patent Application Nos. 201210323848.9, 201210323849.3, 201210323850.6, and 201210323951.3, each filed Sep. 5, 2012. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing and a creation date of Jun. 17, 2017, and a size of 6.4 kilobytes. The Sequence Listing filed via EFS-Web is part of the specification and is hereby incorporated in its entirety by reference herein.

TECHNICAL FIELD

The present invention relates to a novel compound simultaneously having effects of thrombolysis, free radical scavenging and thrombus-targeting, as well as a preparation method and use thereof. The present invention further relates to a novel ternary conjugate of "a peptide comprising a PAK sequence/imidazoline/a peptide comprising an RGD sequence" formed by linking together a thrombolytic oligopeptide comprising a PAK (Pro-Ala-Lys) sequence, 1-(4-oxyacetyl-phenyl)-3,3,4,4-tetramethylimidazoline and a thrombus-targeting peptide/anti-thrombus oligopeptide comprising an RGD (Arg-Gly-Asp) sequence via a linking arm containing carboxyl and amino groups. The present invention further relates to a pharmaceutical composition comprising the above compound for use in NO free radical scavenging, thrombolysis, thrombus targeting/antithrombus therapy, and treatment of stroke/cerebral infarction. The present invention further relates to a method for preparation of the compound.

BACKGROUND ART

Thrombotic diseases rank the first in morbidity and mortality globally. Coronary artery thrombosis results in myocardial infarction. Cerebral vascular thrombosis leads to cerebral infarction, i.e., the clinical ischemic stroke. Patients with myocardial infarction may be intravenously injected with thrombolytic agents or have bypass surgeries. It should be noted that the positive outcome of intravenous injection of thrombolytic agents to patients with myocardial infarction is ischemia/reperfusion. Since a large amount of NO free radicals are generated during the process of ischemia/reperfusion, the thrombolysis process is associated with myocardial damage and patient death. This is a serious problem in current thrombolysis treatment of myocardial infarction. Presently, the treatment of cerebral infarction is confronted with even more complicated problems. For example, current thrombolytic agents are all not able to cross the blood-brain barrier, and therefore the efficacy of intravenous injection of thrombolytic agents in patients with cerebral infarction is rather limited. Also, for example, no appropriate surgical procedure that could save patients with cerebral infarction is available currently. Similarly, even if there is a positive outcome from intravenously injecting thrombolytic agents into patients with cerebral infarction, a tremendous amount of NO free radicals may still be generated in the process of ischemia/reperfusion such that the thrombolysis process is associated with damage of brain tissues and patient death. This is a serious problem in current thrombolysis treatment of cerebral infarction. Moreover, four serious problems are present in the clinical treatment for stroke patients: 1) no medicament other than tPA (tissue-type plasminogen activator) shows efficacy in stroke patients; 2) tPA treatment is only effective within 3 hours from the stroke onset, i.e., there is only a 3-hour window for tPA treatment; 3) tPA treatment often results in systemic bleeding; 4) brain tissue damage in patients and patient death associated with the tremendous amount of NO free radicals produced in the process of ischemia/reperfusion cannot be avoided by tPA treatment. It is thus imperative to solve these four problems in order to achieve a substantive breakthrough in clinical treatment of stroke patients.

Two compounds, $N^\alpha$-(1,3-dioxo-4,4,5,5-tetramethylimidazoline-2-phenyl-4'-oxyacetyl)-$n^\omega$-fatty acyl-Lys-Arg-Gly-Asp-Val (SEQ. ID NO. 1) and $N^\alpha$-(1,3-dioxo-4,4,5,5-tetramethylimidazoline-2-phenyl-4'-oxyacetyl)-$n^\omega$-fatty acyl-Lys-Arg-Gly-Asp-Phe (SEQ. ID NO. 2), are disclosed in Chinese Patent Publication CN102807604 and CN102807605. Both compounds are derived from a conjugation of an imidazoline having NO free radical scavenging activity with an anti-thrombus oligopeptide comprising an RGD sequence (Arg-Gly-Asp) via lysine. Unlike the compound of the present invention, these two compounds do not have a thrombolytic peptide attached therein. These two compounds do not have a function in thrombolysis, and therefore are not suitable in the manufacture of thrombolytic medicaments and not suitable in treatment of patients with ischemic stroke.

To solve the above problems, there is a need for a new compound simultaneously having effects of thrombolysis, free radical scavenging and thrombus-targeting. Furthermore, it is required that such a new compound is able to be effective even if administered after 3 hours from the onset of stroke in patients, i.e., not restricted by the 3-hour window as in the treatment using tPA; does not cause a systemic bleeding response as in tPA treatment; and can clear the tremendous amount of NO free radicals generated during ischemia/reperfusion.

SUMMARY OF THE INVENTION

The present invention provides a ternary conjugate simultaneously having activities of crossing blood-brain barrier, thrombolysis, anti-thrombus and NO free radical scavenging, in which the three members in the ternary conjugate refer to an imidazoline having NO free radical scavenging activity, a peptide having thrombolytic activity, and a thrombus-targeting peptide, wherein the three members are linked together via a proper linking arm.

Specifically, the ternary conjugate of the present invention may be represented by the compound of formula I:

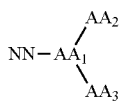

(I)

wherein, NN represents an imidazoline having NO free radical scavenging activity; $AA_1$ represents a linking arm having at least three groups for linking; $AA_2$ represents a peptide having thrombolytic activity; and $AA_3$ represents a thrombus-targeting peptide.

The imidazoline used in the present invention may include imidazole nitroxyl nitroxide (NN) radicals, which can clear NO and function to clear oxygen free radicals, providing strong protection for cells damaged by oxygen free radicals. The imidazoline having NO free radical scavenging activity according to the present invention is preferably 1,3-dioxo-2-[(4-oxyacetoxy)phenyl]-4,4,5,5-tetramethylimidazoline, which has excellent chemical and physical stability, and is not only suitable for any chemical reaction of conjugating a peptide having thrombolytic activity with a thrombus-targeting peptide, but also not susceptible to decomposition during storage, thereby satisfying the requirements for formulations.

The linking arm used in the present invention may comprise at least three groups for linking, e.g., carboxyl and amino groups, which is used to link the imidazoline, the peptide having thrombolytic activity, and the thrombus-targeting peptide together. The linking arm according to the present invention may be natural amino acids, for example, L-Lys, L-Asp, and L-Glu. When the linking arm ($AA_1$) used in the present invention has three or more groups for linking, one or more NN, $AA_2$ or $AA_3$ may be linked thereby, wherein two or more NN, $AA_2$ or $AA_3$ may be the same or different. For example, when $AA_1$ has four groups for linking, one NN, two $AA_2$ and one $AA_3$ may be linked thereby while the two $AA_2$ may be the same or different peptides having thrombolytic activity.

The peptide having thrombolytic activity used in the present invention may be an oligopeptide comprising a PAK (Pro-Ala-Lys) sequence, an AKP (Ala-Lys-Pro) sequence or a KAP (Lys-Ala-Pro) sequence, or a peptide having repeating units of the PAK sequence, the AKP sequence or the KAP sequence. An oligopeptide refer to a small-molecule peptide having a molecular weight of 1000 Dalton (D) or less, which is generally composed of 3 to 8 amino acids. The oligopeptide having thrombolytic activity according to the present invention may be a tripeptide to octopeptide that comprises a PAK sequence, an AKP sequence, or a KAP sequence, preferably a tripeptide to pentapeptide that comprises a PAK sequence, an AKP sequence, or a KAP sequence. For instance, the oligopeptide used for the present invention that comprises a PAK sequence, an AKP sequence, or a KAP sequence may be PAK, RPAK (Arg-Pro-Ala-Lys) (SEQ. ID NO. 3), ARPAK (Ala-Arg-Pro-Ala-Lys) (SEQ. ID NO. 4), GRPAK (Gly-Arg-Pro-Ala-Lys) (SEQ. ID NO. 5), QRPAK (Gln-Arg-Pro-Ala-Lys) (SEQ. ID NO. 6), AKP, KAP, KPAK (Lys-Pro-Ala-Lys) (SEQ. ID NO. 7), PAKP (Pro-Ala-Lys-Pro) (SEQ. ID NO. 8), AKPAK (Ala-Lys-Pro-Ala-Lys) (SEQ. ID NO. 9) or PAKPA (Pro-Ala-Lys-Pro-Ala) (SEQ. ID NO. 10). For example, the peptide having repeating units of the PAK sequence, the AKP sequence or the KAP sequence used in the present invention may be any of those peptides being described in the Chinese patent publication CN101190941 as a peptide having thrombolytic activity, including a peptide having repeating units of the PAK sequence, such as $(PAK)_2$, $(PAK)_3$, $(PAK)_4$, $(PAK)_5$ and $(PAK)_6$; a peptide having repeating units of the AKP sequence, such as $(AKP)_2$, $(AKP)_3$, $(AKP)_4$, $(AKP)_5$ and $(AKP)_6$; and a peptide having repeating units of the KPA sequence, such as $(KPA)_2$, $(KPA)_3$, $(KPA)_4$, $(KPA)_5$ and $(KPA)_6$.

The thrombus-targeting/anti-thrombus peptide used in the present invention may be an oligopeptide containing an RGD sequence (Arg-Gly-Asp). The oligopeptide containing an RGD sequence may be an RGD-based tetrapeptide, such as RGDS (Arg-Gly-Asp-Ser) (SEQ. ID NO. 11), RGDV (Arg-Gly-Asp-Val) (SEQ. ID NO. 12) and RGDF (Arg-Gly-Asp-Phe) (SEQ. ID NO. 13). Specific binding of fibrinogen (Fg) to activated platelet membrane glycoprotein (GP) IIb/IIIa receptor is the common final pathway leading to platelet aggregation triggered by various physiological inducers, and plays an important role in the formation of thrombus. Further, RGD sequences serve as active sites for the binding of Fg ligands and activated GPIIb/IIIa receptors and have an activated platelet-targeting property. Structures comprising an RGD sequence may competitively inhibit and block the binding of Fg and GPIIb/IIIa receptors, thereby preventing platelet aggregation and thrombus formation, so as to enable an RGD-containing oligopeptide become an effective thrombus-targeting molecule and anti-thrombus agent.

Further, the thrombus-targeting peptide used in the present invention may be any of those polypeptides being described in Chinese patent publication CN101190940 as a polypeptide having targeting and anti-thrombus activity, including the polypeptides obtained from conjugating modification of an RGD peptide with a YIGS (Tyr-Ile-Gly-Ser) (SEQ. ID NO. 14) peptide. The polypeptides obtained by modification includes YIGSRRGDS (SEQ. ID NO. 15), YIGSRRGDV (SEQ. ID NO. 16), YIGSRRGDF (SEQ. ID NO. 17), YIGSRYIGSK (SEQ. ID NO. 18), YIGSRYIGSR (SEQ. ID NO. 19), YIGSKRGDS (SEQ. ID NO. 20), YIGSKRGDF (SEQ. ID NO. 21), YIGSKRGDV (SEQ. ID NO. 22), YIGSKYIGSK (SEQ. ID NO. 23), YIGSKYIGSR (SEQ. ID NO. 24), RGDSRGDS (SEQ. ID NO. 25), RGDVRGDV (SEQ. ID NO. 26), RGDFRGDF (SEQ. ID NO. 27), RGDSYIGSR (SEQ. ID NO. 28), RGDSYIGSK (SEQ. ID NO. 29), RGDVYIGSR (SEQ. ID NO. 30), RGDVYIGSK (SEQ. ID NO. 31), RGDFYIGSR (SEQ. ID NO. 32), or RGDFYIGSK (SEQ. ID NO. 33).

In a preferred embodiment, in the compound according to the present invention, the imidazoline having NO free radical scavenging activity is 1,3-dioxo-2-[(4-oxyacetoxy)phenyl]-4,4,5,5-tetramethylimidazoline, the peptide having thrombolytic activity is an oligopeptide comprising a PAK sequence (Pro-Ala-Lys), and the thrombus-targeting peptide is an oligopeptide comprising an RGD sequence (Arg-Gly-Asp). Thus, the present invention provides a ternary conjugate of "a peptide comprising a PAK sequence/imidazoline/a peptide comprising an RGD sequence" simultaneously having activities in crossing blood-brain barrier, thrombolysis, anti-thrombus and NO free radical scavenging.

In an embodiment, in the compound according to the present invention, the imidazoline having NO free radical scavenging activity is 1,3-dioxo-2-[(4-oxyacetoxy)phenyl]-4,4,5,5-tetramethylimidazoline, the linking arm is L-Lys, the peptide having thrombolytic activity is an oligopeptide comprising a PAK sequence (Pro-Ala-Lys), and the thrombus-targeting peptide is an oligopeptide comprising an RGD sequence (Arg-Gly-Asp). In this case, the oligopeptide comprising a PAK sequence may be an ARPAK (SEQ. ID NO. 4) pentapeptide, a GRPAK (SEQ. ID NO. 5) pentapeptide, an RPAK (SEQ. ID NO. 3) tetrapeptide, or a PAK tripeptide; the oligopeptide comprising an RGD sequence (Arg-Gly-Asp) may be an RGD-based tetrapeptide, such as RGDS (SEQ. ID NO. 11), RGDV (SEQ. ID NO. 12) or RGDF (SEQ. ID NO. 13). When L-Lys is used as the linking arm, the compound according to the present invention may be of following general formula I-1 or I-2:

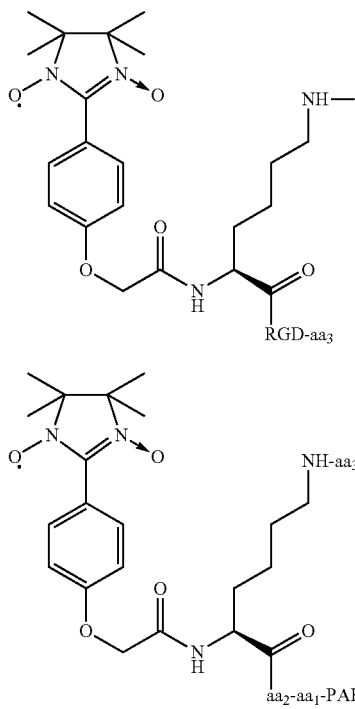

I-1

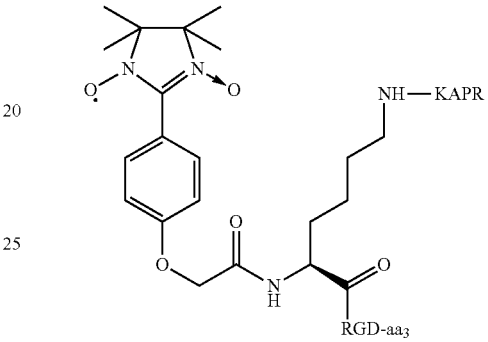

I-1-2

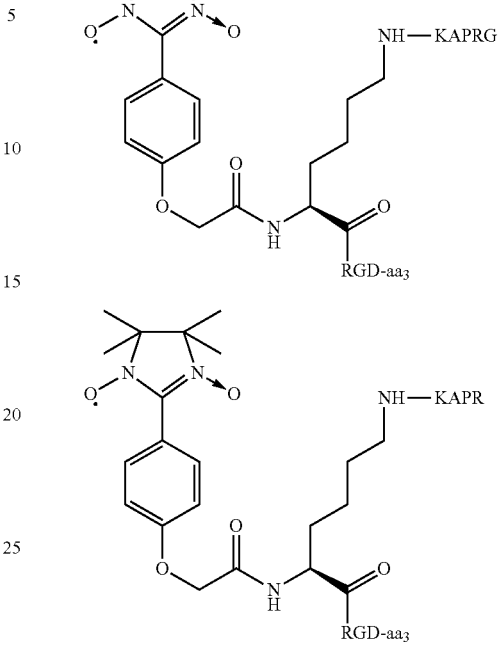

I-2

I-1-3

I-1-4 wherein, aa₁ and aa₂ may be both present or both absent, or aa₁ is present but aa₂ is absent; when both of aa₁ and aa₂ are present, aa₁ is R (Arg), and aa₂ is G (Gly), A (Ala) or Q (Gln); when aa₁ is present but aa₂ is absent, aa₁ is R (Arg); aa₃ may be S (Ser), V (Val), or F (Phe).

For examples related to the compound of general formula I-1, in a preferred example, the compound according to the present invention may be a ternary conjugate of ARPAK (SEQ. ID NO. 4)/imidazoline/RGD represented by following formula I-1-1; in another preferred example, the compound according to the present invention may be a ternary conjugate of GRPAK (SEQ. ID NO. 5)/imidazoline/RGD represented by following formula I-1-2; in still another preferred example, the compound according to the present invention may be a ternary conjugate of RPAK (SEQ. ID NO. 3)/imidazoline/RGD represented by following formula I-1-3; and in still another preferred example, the compound according to the present invention may be a ternary conjugate of PAK/imidazoline/RGD represented by following formula I-1-4:

wherein ARPAK is (SEQ. ID NO. 4), GRPAK is (SEQ. ID NO. 5), RPAK is (SEQ. ID NO. 3), aa₃ may be S (Ser), V (Val) or F (Phe), preferably V (Val).

For examples related to the compound of general formula I-2, the compound according to the present invention may be preferably of following general formula I-2-1, I-2-2, I-2-3 or I-2-4:

I-1-1

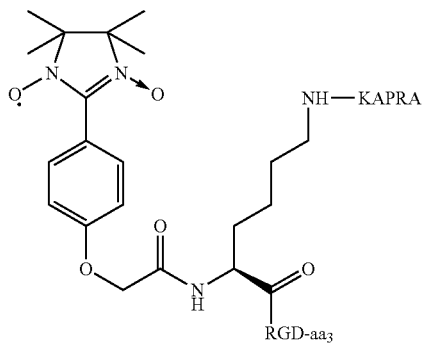

I-2-1

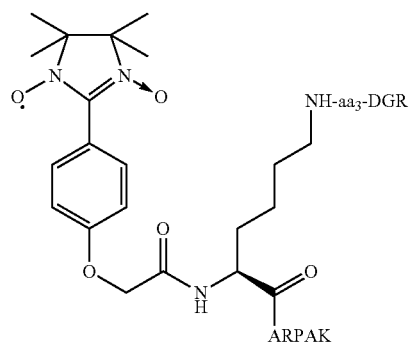

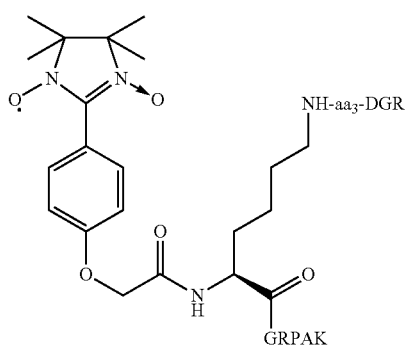

I-2-2

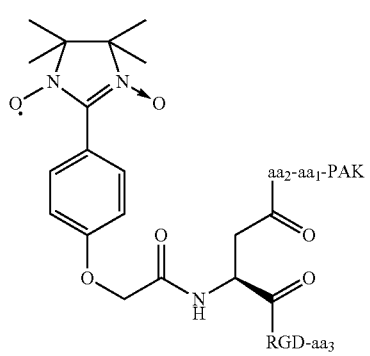

I-3

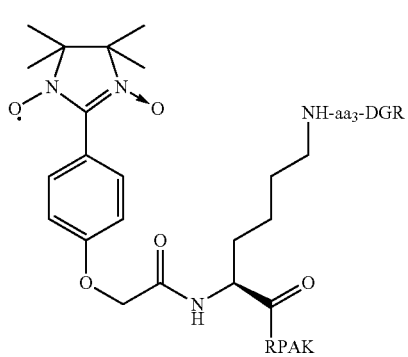

I-2-3

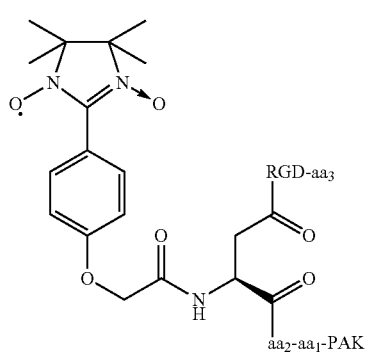

I-4

I-2-4 wherein, aa$_1$ and aa$_2$ may be both present or both absent, or aa$_1$ is present but aa$_2$ is absent; when both of aa$_1$ and aa$_2$ are present, aa$_1$ is R (Arg), and aa$_2$ is G (Gly), A (Ala) or Q (Gln); when aa$_1$ is present but aa$_2$ is absent, aa$_1$ is R (Arg); aa$_3$ may be S (Ser), V (Val), or F (Phe). aa$_1$ is preferably R (Arg), aa$_2$ is preferably G (Gly), and aa$_3$ is preferably V (Val).

wherein ARPAK is (SEQ. ID NO. 4), GRPAK is (SEQ. ID NO. 5), RPAK is (SEQ. ID NO. 3), aa$_3$ may be S (Ser), V (Val) or F (Phe), preferably V (Val).

For examples related to the compound of general formula I-3, the compound according to the present invention may be preferably of following general formula I-3-1, I-3-2, I-3-3 or I-3-4:

In another embodiment, in the compound according to the present invention, the imidazoline having NO free radical scavenging activity is 1,3-dioxo-2-[(4-oxyacetoxy)phenyl]-4,4,5,5-tetramethylimidazoline, the linking arm is L-Asp, the peptide having thrombolytic activity is an oligopeptide comprising a PAK sequence (Pro-Ala-Lys), and the thrombus-targeting peptide is an oligopeptide comprising an RGD sequence (Arg-Gly-Asp). When L-Asp is used as the linking arm, the compound according to the present invention may be of following general formula I-3 or I-4:

I-3-1

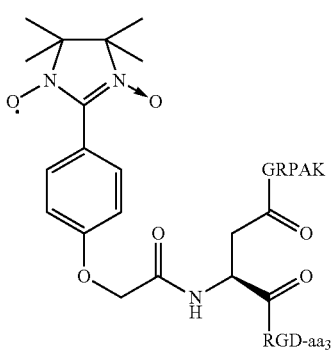
I-3-2

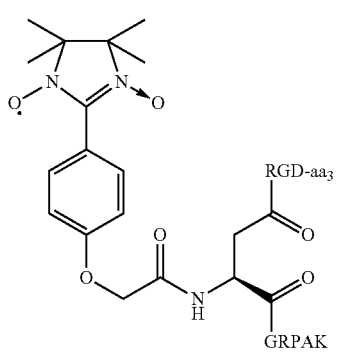
I-4-2

I-3-3

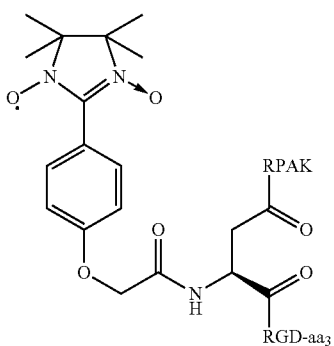

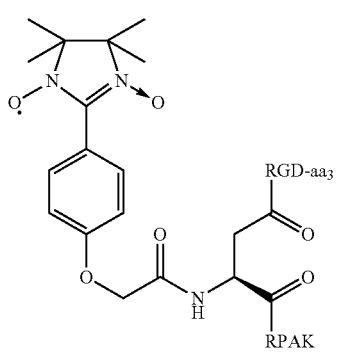
I-4-3

I-3-4

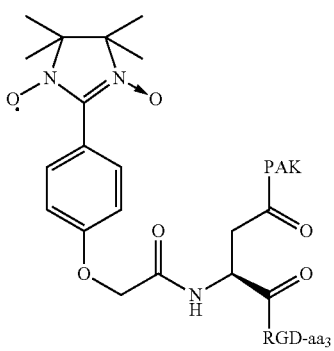

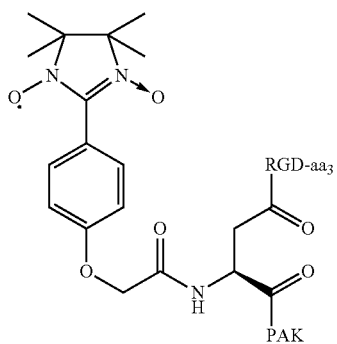
I-4-4 wherein ARPAK is (SEQ. ID NO. 4), GRPAK is (SEQ. ID NO. 5), RPAK is (SEQ. ID NO. 3) aa₃ may be S (Ser), V (Val) or F (Phe), preferably V (Val).

For examples related to the compound of general formula I-4, the compound according to the present invention may be preferably of following general formula I-4-1, I-4-2, I-4-3 or I-4-4:

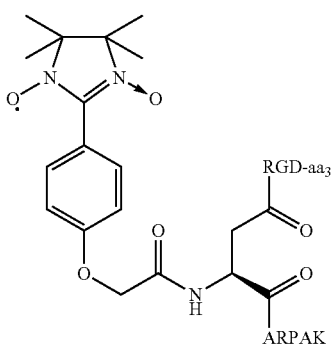
I-4-1 wherein ARPAK is (SEQ. ID NO. 4), GRPAK is (SEQ. ID NO. 5), RPAK is (SEQ. ID NO. 3), aa₃ may be S (Ser), V (Val) or F (Phe), preferably V (Val).

In still another embodiment, in the compound according to the present invention, the imidazoline having NO free radical scavenging activity is 1,3-dioxo-2-[(4-oxyacetoxy)phenyl]-4,4,5,5-tetramethylimidazoline, the linking arm is L-Glu, the peptide having thrombolytic activity is an oligopeptide comprising a PAK sequence (Pro-Ala-Lys), and the thrombus-targeting peptide is an oligopeptide comprising an RGD sequence (Arg-Gly-Asp). When L-Glu is used as the linking arm, the compound according to the present invention may be of following general formula I-5 or 1-6:

I-5

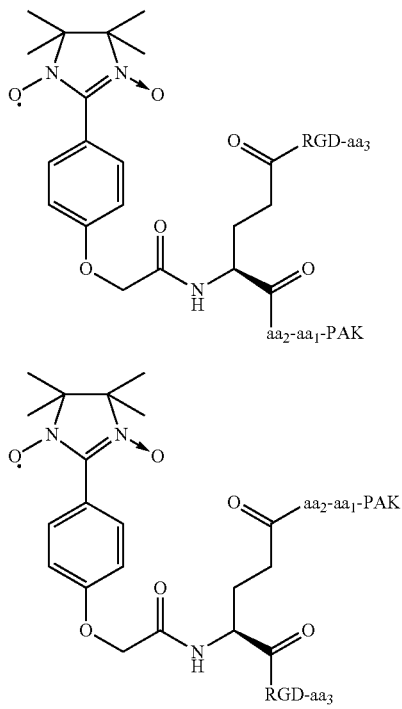

I-6

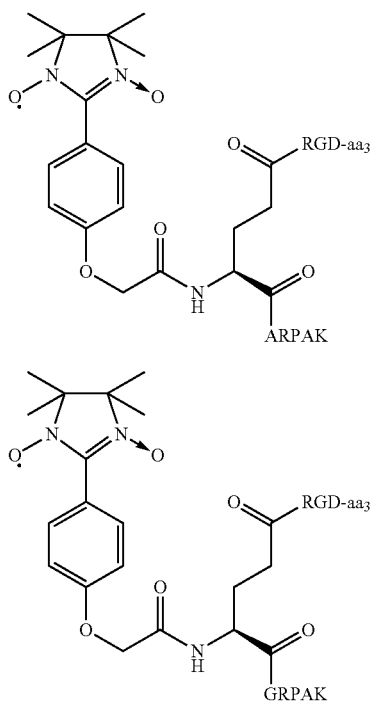

wherein, aa$_1$ and aa$_2$ may be both present or both absent, or aa$_1$ is present but aa$_2$ is absent; when both of aa$_1$ and aa$_2$ are present, aa$_1$ is R (Arg), and aa$_2$ is G (Gly), A (Ala) or Q (Gln); when aa$_1$ is present but aa$_2$ is absent, aa$_1$ is R (Arg); aa$_3$ may be S (Ser), V (Val), or F (Phe). aa$_1$ is preferably R (Arg), aa$_2$ is preferably G (Gly), and aa$_3$ is preferably V (Val).

For examples related to the compound of general formula I-5, the compound according to the present invention may be preferably of following general formula I-5-1, I-5-2, I-5-3 or I-5-4:

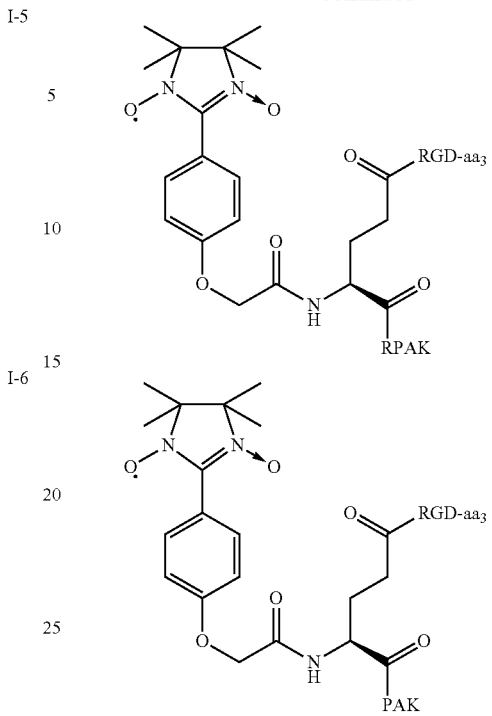

wherein ARPAK is (SEQ. ID NO. 4), GRPAK is (SEQ. ID NO. 5), RPAK is (SEQ. ID NO. 3), aa$_3$ may be S (Ser), V (Val) or F (Phe), preferably V (Val).

For examples related to the compound of general formula I-6, the compound according to the present invention may be preferably of following general formula I-6-1, I-6-2, I-6-3 or I-6-4:

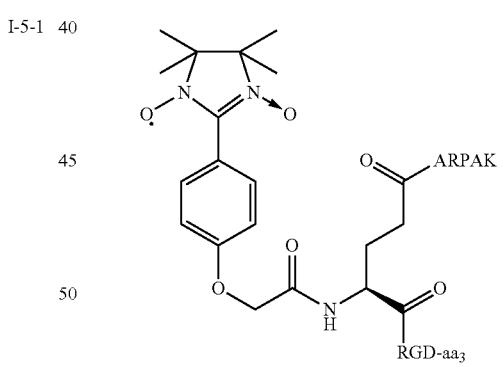

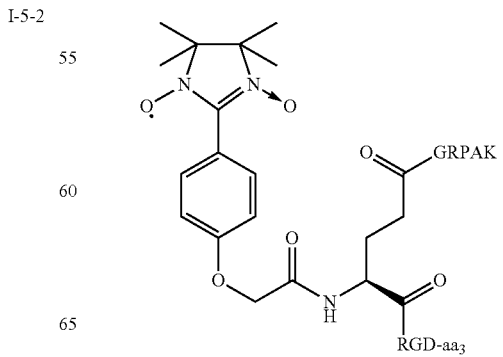

-continued

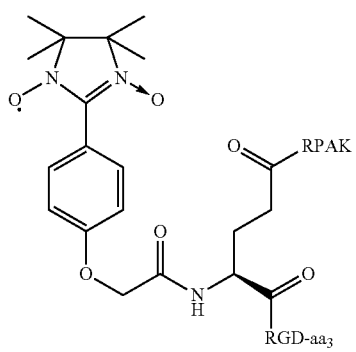

I-6-3

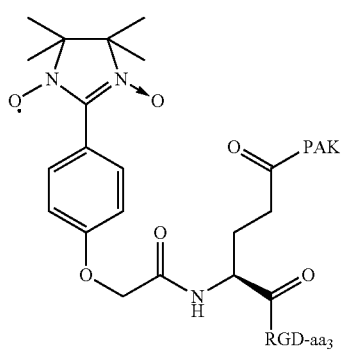

I-6-4 wherein ARPAK is (SEQ. ID NO. 4), GRPAK is (SEQ. ID NO. 5), and RPAK is (SEQ. ID NO. 3) aa₃ may be S (Ser), V (Val) or F (Phe), preferably V (Val).

In another aspect, the present invention further relates to a pharmaceutical composition comprising the above compound according to the present invention and a pharmaceutically acceptable carrier. Preferably, the pharmaceutical composition according to the present invention comprises the compound of above general formula I-1, I-2, I-3, I-4, I-5 or I-6. More preferably, the pharmaceutical composition according to the present invention comprises the compound of above general formula I-1-1, I-1-2, I-1-3 or I-1-4. When the pharmaceutical composition according to the present invention comprises the compound of the general formula I-1-1, I-1-2, I-1-3 or I-1-4, the compound may be in the form of a dimer, trimer or tetramer structure in the pharmaceutical composition, and may be in the form of a nanosphere having a diameter of 2 to 300 nm. In the pharmaceutical composition according to the present invention, the nanospherical structure may preferably have a diameter of 2 to 100 nm. It is a fact well known in nanopharmacology that nanospheres having a diameter of less than 100 nm are less prone to be engulfed by macrophages during transportation in blood and may readily cross the blood capillary wall. These properties allow the compound according to the present invention to cross the blood-brain barrier. The pharmaceutical composition according to the present invention may be used as a thrombolytic drug in treating diseases such as myocardial infarction, ischemic stroke, deep vein thrombosis, pulmonary embolism, peripheral arterial occlusive disease, occluded central vascular access devices, clotted arteriovenous fistula and shunts, and carotid stenosis. The pharmaceutical composition according to the present invention may also be used as an NO free radical-scavenging drug in treating neurodegenerative diseases, such as Alzheimer's disease, Parkinson's disease, motor neuron diseases, amyotrophic lateral sclerosis, noise-induced hearing loss, Lou Gehrig's disease or Huntington's disease; in treating cardiovascular diseases, such as atherosclerosis, coronary heart disease or myocardial infarction; in treating mental diseases, such as bipolar disorder, schizophrenia or autism; and in treating diseases including altitude sickness, diabetes, rheumatoid arthritis, traumatic brain injury, cancer, fragile X syndrome, sickle cell disease, Lichen planus, vitiligo, chronic fatigue syndrome and so on. The pharmaceutical composition according to the present invention may further be used as a thrombus targeting/anti-thrombus drug in treating diseases such as thrombocytosis, myeloproliferative disease, polycythemia vera or Budd-Chiari syndrome. The pharmaceutical composition according to the present invention may also be used as a drug in treating stroke or cerebral infarction, preferably in treating stroke or cerebral infarction beyond 3, 4, 6 and 24 hours from the onset of symptoms with successive administrations. The pharmaceutical composition/compound according to the present invention simultaneously has functions of NO free radical scavenging, thrombolysis, and anti-thrombus/thrombus targeting, and therefore shows efficacy even when being administered after 3 hours from the onset of stroke in patients; namely, it is not restricted by the 3-hour window as in the treatment using tPA, does not cause a systemic bleeding response as tPA, and can clear the tremendous amount of NO free radicals generated during ischemia/reperfusion, preventing damage to cranial nerve tissues in patients during the treatment. In the pharmaceutical composition according to the present invention, the nanospherical structures of the compounds are able to maximize the effects of blood-brain barrier crossing, thrombolysis, thrombus targeting/anti-thrombus, as well as the effect of clearing the NO free radicals generated during ischemia/reperfusion.

The pharmaceutical composition according to the present invention may be any clinically acceptable formulation, for example, an injectable formulation (powder for injection, lyophilized powder for injection, liquid for injection, infusion etc.), a tablet, oral liquid, a granule, a capsule, a soft capsule, a dripping pill and so on, wherein the pharmaceutically acceptable carriers may be one or more of xylitol, manitol, lactose, fructose, dextran, glucose, polyvinylpyrrolidone, low-molecular-weight dextran, sodium chloride, calcium gluconate, or calcium phosphate. In addition, the pharmaceutical composition according to the present invention may further comprise an excipient that may be an antioxidant complexing agent, a filler, a framework material, and so on.

In another aspect, the present invention further relates to a preparation method of the aforementioned compound of formula I, comprising the steps of:

(1) providing an imidazoline having NO free radical scavenging activity (NN), a linking arm having at least three groups for linking (AA₁), a peptide having thrombolytic activity (AA₂) and a thrombus-targeting peptide (AA₃), wherein the linking arm has a first group for linking, a second group for linking, and a third group for linking;

(2) under appropriate reaction conditions, linking the imidazoline having NO free radical scavenging activity (NN) to the first group for linking on the linking arm (AA₁), to form a compound of general formula IM-1:

NN-AA₁    (IM-1);

(3) under appropriate reaction conditions, linking the peptide having thrombolytic activity (AA₂) to the compound of general formula IM-1, wherein one end of the peptide having thrombolytic activity is linked to the second group for linking on the linking arm, to form a compound of general formula IM-2:

$$NN-AA_1-AA_2 \qquad (IM-2); \text{ and}$$

(4) under appropriate reaction conditions, linking the thrombus-targeting peptide ($AA_3$) to the compound of general formula IM-2, wherein one end of the thrombus-targeting peptide is linked to the third group for linking on the linking arm, to form the compound of formula I;

wherein step (3) and (4) are exchangeable in order.

In the preparation method according to the present invention, step (1) further comprises protecting the second and the third groups for linking on the linking arm ($AA_1$) with protecting groups, and protecting active groups of the peptide having thrombolytic activity ($AA_2$) and of the thrombus-targeting peptide ($AA_3$), other than the end to be used for linking, with protecting groups; step (3) further comprises deprotecting the protected second group for linking first, and then linking the peptide having thrombolytic activity to the deprotected second group for linking; step (4) further comprises deprotecting the protected third group for linking first, and then linking the thrombus-targeting peptide to the deprotected third group for linking; and after step (4), there is further a step of deprotecting the protected active groups of the peptide having thrombolytic activity ($AA_2$) and of the thrombus-targeting peptide ($AA_3$). By applying techniques of adding and removing protecting groups, the order in which NN, $AA_2$ and $AA_3$ are linked to the linking arm and linking position thereof are controllable. Protecting groups on other active groups are then removed after completion of the coupling. Appropriate reaction conditions refer to conventional conditions employed in peptide synthesis. The imidazoline having NO free radical scavenging activity (NN), the linking arm having at least three groups for linking ($AA_1$), the peptide having thrombolytic activity ($AA_2$), and the thrombus-targeting peptide ($AA_3$) are the same as defined above for the compound of formula I according to the present invention.

The preparation method of the present invention may be further understood from the more detailed description as follows.

In an embodiment, the first group for linking on the linking arm in the preparation method according to the present invention is an amino group, while the second and the third groups for linking are selected from the group consisting of a carboxyl group and an amino group.

In a preferred embodiment of the preparation method according to the present invention, the imidazoline having NO free radical scavenging activity is 1,3-dioxo-2-[(4-oxyacetoxy)phenyl]-4,4,5,5-tetramethylimidazoline, the linking arm is L-Lys, the peptide having thrombolytic activity is an oligopeptide comprising a PAK sequence (Pro-Ala-Lys), and the thrombus-targeting peptide is an oligopeptide comprising an RGD sequence (Arg-Gly-Asp). When the linking arm is L-Lys, there may be the following two ways for conjugating:

(1) 1,3-dioxo-2-[(4-oxyacetoxy)phenyl]-4,4,5,5-tetramethylimidazoline is linked to an amino group on the L-Lys linking arm, a carboxyl group on the oligopeptide comprising a PAK sequence is linked to another amino group on the L-Lys linking arm, and an amino group on the oligopeptide comprising an RGD sequence is linked to a carboxyl group on the L-Lys linking arm (as shown in the above compound of formula I-1); or (2) 1,3-dioxo-2-[(4-oxyacetoxy)phenyl]-4,4,5,5-tetramethylimidazoline is linked to an amino group on the L-Lys linking arm, an amino group on the oligopeptide comprising a PAK sequence is linked to a carboxyl group on the L-Lys linking arm, and a carboxyl group on the oligopeptide comprising an RGD sequence is linked to another amino group on the L-Lys linking arm (as shown in the above compound of formula I-2).

For examples related to the compound of formula I-1, when the compound of general formula I-1-1, I-1-2, I-1-3 or I-1-4 is prepared, the preparation method of the present invention may be carried out according to the synthesis schemes shown in FIGS. 1 to 4. FIG. 1 shows a synthesis scheme for the compound of general formula I-1-1. FIG. 2 shows a synthesis scheme for the compound of general formula I-1-2. FIG. 3 shows a synthesis scheme for the compound of general formula I-1-3. FIG. 4 shows a synthesis scheme for the compound of general formula I-1-4. In FIGS. 1 to 4, $aa_3$ may be S (Ser), V (Val), or F (Phe), as described above. For examples related to the compound of general formula I-1-2, the preparation method according to the present invention is described as follows:

(1) preparing 1,3-dioxo-2-(4-oxyacetoxy-phenyl)-4,4,5,5-tetramethylimidazoline;

(2) preparing 1,3-dioxo-2-[(4'-oxyacetyl-Lys-OMe)phenyl]-4,4,5,5-tetramethylimidazoline (the carboxyl group on the Lys linking arm is protected with a protecting group);

(3) preparing HCl·Arg($NO_2$)-Gly-Asp(OBzl)-Ser(Bzl)-Obzl, HCl·Arg($NO_2$)-Gly-Asp(OBzl)-Val-Obzl or HCl·Arg($NO_2$)-Gly-Asp(OBzl)-Phe-Obzl;

(4) preparing Boc-Gly-Arg($NO_2$)-Pro-Ala-Lys(Z);

(5) linking Boc-Gly-Arg($NO_2$)-Pro-Ala-Lys(Z) to the lysine of 1,3-dioxo-2-[(4'-oxyacetyl-Lys-OMe)phenyl]-4,4,5,5-tetramethylimidazoline to provide 1,3-dioxo-2-{4'-oxyacetyl-{$N^\omega$–[Boc-Gly-Arg($NO_2$)-Pro-Ala-Lys(Z)]-Lys}phenyl}-4,4,5,5-tetramethylimidazoline;

(6) respectively conjugating HCl·Arg($NO_2$)-Gly-Asp(OBzl)-Ser(Bzl)-Obzl, HCl·Arg($NO_2$)-Gly-Asp(OBzl)-Val-Obzl, or HCl·Arg($NO_2$)-Gly-Asp(OBzl)-Phe-Obzl to 1,3-dioxo-2-{4'-oxyacetyl-{$N^\omega$-[Boc-Gly-Arg($NO_2$)-Pro-Ala-Lys(Z)]-Lys}phenyl}-4,4,5,5-tetramethylimidazoline to afford 1,3-dioxo-2-{4'-oxyacetyl-{$N^\omega$-[Boc-Gly-Arg($NO_2$)-Pro-Ala-Lys(Z)]-Lys-Arg($NO_2$)-Gly-Asp(OBzl)-Ser(Bzl)-OBzl}phenyl}-4,4,5,5-tetramethylimidazoline, 1,3-dioxo-2-{4'-oxyacetyl-{$N^\omega$-[Boc-Gly-Arg($NO_2$)-Pro-Ala-Lys(Z)]-Lys-Arg-($NO_2$)-Gly-Asp-(OBzl)-Val-OBzl}phenyl}-4,4,5,5-tetramethylimidazoline, or 1,3-dioxo-2-{4'-oxyacetyl-{$N^\omega$-[Boc-Gly-Arg($NO_2$)-Pro-Ala-Lys(Z)]-Lys-Arg($NO_2$)-Gly-Asp(OBzl)-Phe-OBzl}phenyl}-4,4,5,5-tetramethylimidazoline, respectively;

(7) deprotecting the compounds resulting from step (6) to afford 1,3-dioxo-2-{4'-oxyacetyl-{$N^\omega$-[Gly-Arg-Pro-Ala-Lys]-Lys-Arg-Gly-Asp-Ser}phenyl}-4,4,5,5-tetramethylimidazolin, 1,3-dioxo-2-{4'-oxyacetyl-{$N^\omega$-[Gly-Arg-Pro-Ala-Lys]-Lys-Arg-Gly-Asp-Val}phenyl}-4,4,5,5-tetramethylimidazoline or 1,3-dioxo-2-{4'-oxyacetyl-{$N^\omega$-[Gly-Arg-Pro-Ala-Lys]-Lys-Arg-Gly-Asp-Phe}phenyl}-4,4,5,5-tetramethylimidazoline.

In the case that the compounds of general formula I-1-1, I-1-3 and I-1-4 are prepared, the above manufacturing process is repeated but replacing "Boc-Gly-Arg($NO_2$)-Pro-Ala-Lys(Z)" in step (4) with "Boc-Ala-Arg($NO_2$)-Pro-Ala-Lys(Z)", "Boc-Arg($NO_2$)-Pro-Ala-Lys(Z)" and "Boc-Pro-Ala-Lys(Z)".

Active groups at appropriate positions on the oligopeptide comprising a PAK sequence and the oligopeptide comprising an RGD sequence may be protected per need of conjugation design, so that one end of the selected sequences (comprising an active group to be attached to the linking arm) is used to couple to an active group on the linking arm. The step of coupling the oligopeptide comprising a PAK sequence and the step of coupling the oligopeptide comprising an RGD sequence are exchangeable in order. For example, the oligopeptide comprising an RGD sequence is coupled to the linking arm first, and then the oligopeptide comprising a PAK sequence is coupled thereto.

Active groups include groups that may be subjected to condensation reaction, such as an amino group or a carboxyl group. Amino-protecting groups may be carboxybenzyl (CBz), t-butoxy carbonyl (Boc), 9-florenyl methoxy carbonyl (Fmoc), benzyl (Bn) or p-methoxyphenyl (PMP). Carboxyl-protecting groups may be methyl ester (OMe), benzyl ester (OBn), benzyl methyl ester (Obzl), t-butyl ester (OBUT), or silyl ester (OSi(CH$_3$)$_3$).

For examples related to the compound of formula I-2, when the compound of general formula I-2-1, I-2-2, I-2-3 or I-2-4 is prepared, the preparation method of the present invention may be carried out according to the synthesis schemes shown in FIGS. 5 to 8. FIG. 5 shows a synthesis scheme for the compound of general formula I-2-1. FIG. 6 shows a synthesis scheme for the compound of general formula I-2-2. FIG. 7 shows a synthesis scheme for the compound of general formula I-2-3. FIG. 8 shows a synthesis scheme for the compound of general formula I-2-4. In FIGS. 5 to 8, aa$_3$ may be S (Ser), V (Val), or F (Phe), as described above. When the compound of general formula I-2-1, I-2-2, I-2-3 or I-2-4 is prepared, 1,3-dioxo-2-[(4'-oxyacetyl-Lys-OMe)phenyl]-4,4,5,5-tetramethylimidazoline may be prepared first, and then the C terminal of the oligopeptide comprising an RGD sequence is attached to the amino group on the Lys linking arm; and finally, the N terminal of the oligopeptide comprising a PAK sequence is attached to the deprotected carboxyl group on the linking arm.

In another embodiment, in the preparation method according to the present invention, the imidazoline having NO free radical scavenging activity is 1,3-dioxo-2-[(4-oxyacetoxy)phenyl]-4,4,5,5-tetramethylimidazoline, the linking arm is L-Asp, the peptide having thrombolytic activity is an oligopeptide comprising a PAK sequence (Pro-Ala-Lys), and the thrombus-targeting peptide is an oligopeptide comprising an RGD sequence (Arg-Gly-Asp), wherein 1,3-dioxo-2-[(4-oxyacetoxy)phenyl]-4,4,5,5-tetramethylimidazoline is linked to the amino group on the L-Asp linking arm, the amino group on the oligopeptide comprising a PAK sequence is linked to one carboxyl group on the L-Asp linking arm, and the amino group on the oligopeptide comprising an RGD sequence is linked to another carboxyl group on the L-Asp linking arm (as shown in the above compound of formula I-3 or I-4).

For examples related to the compound of formula I-3, when the compound of general formula I-3-1, I-3-2, I-3-3 or I-3-4 is prepared, the preparation method of the present invention may be carried out according to the synthesis schemes shown in FIGS. 9 to 12. FIG. 9 shows a synthesis scheme for the compound of general formula I-3-1. FIG. 10 shows a synthesis scheme for the compound of general formula I-3-2. FIG. 11 shows a synthesis scheme for the compound of general formula I-3-3. FIG. 12 shows a synthesis scheme for the compound of general formula I-3-4. In FIGS. 9 to 12, aa$_3$ may be S (Ser), V (Val), or F (Phe), as described above. When the compound of general formula I-3-1, I-3-2, I-3-3 or I-3-4 is prepared, 1,3-dioxo-2-[(4'-oxyacetyl-Asp-OMe)phenyl]-4,4,5,5-tetramethylimidazoline may be prepared first, and then the N terminal of the oligopeptide comprising a PAK sequence is attached to one carboxyl group on the Asp linking arm; and finally, the N terminal of the oligopeptide comprising an RGD sequence is attached to another deprotected carboxyl group on the Asp linking arm.

For examples related to the compound of formula I-4, when the compound of general formula I-4-1, I-4-2, I-4-3 or I-4-4 is prepared, the preparation method of the present invention may be carried out according to the synthesis schemes shown in FIGS. 13 to 16. FIG. 13 shows a synthesis scheme for the compound of general formula I-4-1. FIG. 14 shows a synthesis scheme for the compound of general formula I-4-2. FIG. 15 shows a synthesis scheme for the compound of general formula I-4-3. FIG. 16 shows a synthesis scheme for the compound of general formula I-4-4. In FIGS. 13 to 16, aa$_3$ may be S (Ser), V (Val), or F (Phe), as described above. When the compound of general formula I-4-1, I-4-2, I-4-3 or I-4-4 is prepared, 1,3-dioxo-2-[(4'-oxyacetyl-Asp-OMe)phenyl]-4,4,5,5-tetramethylimidazoline may be prepared first, and then the N terminal of the oligopeptide comprising an RGD sequence is attached to one carboxyl group on the Asp linking arm; and finally, the N terminal of the oligopeptide comprising a PAK sequence is attached to another deprotected carboxyl group on the Asp linking arm.

In still another embodiment, in the preparation method according to the present invention, the imidazoline having NO free radical scavenging activity is 1,3-dioxo-2-[(4-oxyacetoxy)phenyl]-4,4,5,5-tetramethylimidazoline, the linking arm is L-Glu, the peptide having thrombolytic activity is an oligopeptide comprising a PAK sequence (Pro-Ala-Lys), and the thrombus-targeting peptide is an oligopeptide comprising an RGD sequence (Arg-Gly-Asp), wherein 1,3-dioxo-2-[(4-oxyacetoxy)phenyl]-4,4,5,5-tetramethylimidazoline is linked to the amino group on the L-Glu linking arm, the amino group on the oligopeptide comprising a PAK sequence is linked to one carboxyl group on the L-Glu linking arm, and the amino group on the oligopeptide comprising an RGD sequence is linked to another carboxyl group on the L-Glu linking arm (as shown in the above compound of formula I-5 or I-6).

For examples related to the compound of formula I-5, when the compound of general formula I-5-1, I-5-2, I-5-3 or I-5-4 is prepared, the preparation method of the present invention may be carried out according to the synthesis schemes shown in FIGS. 17 to 20. FIG. 17 shows a synthesis scheme for the compound of general formula I-5-1. FIG. 18 shows a synthesis scheme for the compound of general formula I-5-2. FIG. 19 shows a synthesis scheme for the compound of general formula I-5-3. FIG. 20 shows a synthesis scheme for the compound of general formula I-5-4. In FIGS. 17 to 20, aa$_3$ may be S (Ser), V (Val), or F (Phe), as described above. When the compound of general formula I-5-1, I-5-2, I-5-3 or I-5-4 is prepared, 1,3-dioxo-2-[(4'-oxyacetyl-Glu-OMe)phenyl]-4,4,5,5-tetramethylimidazoline may be prepared first, and then the N terminal of the oligopeptide comprising an RGD sequence is attached to one carboxyl group on the Glu linking arm; and finally, the N terminal of the oligopeptide comprising an PAK sequence is attached to another deprotected carboxyl group on the Glu linking arm.

For examples related to the compound of formula I-6, when the compound of general formula I-6-1, I-6-2, I-6-3 or I-6-4 is prepared, the preparation method of the present invention may be carried out according to the synthesis schemes shown in FIGS. 21 to 24. FIG. 21 shows a synthesis scheme for the compound of general formula I-6-1. FIG. 22 shows a synthesis scheme for the compound of general formula I-6-2. FIG. 23 shows a synthesis scheme for the compound of general formula I-6-3. FIG. 24 shows a synthesis scheme for the compound of general formula I-6-4. In FIGS. 21 to 24, $aa_3$ may be S (Ser), V (Val), or F (Phe), as described above. When the compound of general formula I-6-1, I-6-2, I-6-3 or I-6-4 is prepared, 1,3-dioxo-2-[(4'-oxyacetyl-Glu-OMe)phenyl]-4,4,5,5-tetramethylimidazoline may be prepared first, and then the N terminal of the oligopeptide comprising a PAK sequence is attached to one carboxyl group on the Glu linking arm; and finally, the N terminal of the oligopeptide comprising an RGD sequence is attached to another deprotected carboxyl group on the Glu linking arm.

In the preparation method previously described, the oligopeptide comprising a PAK sequence may be ARPAK(Ala-Arg-Pro-Ala-Lys) (SEQ. ID NO. 4), GRPAK(Gly-Arg-Pro-Ala-Lys) (SEQ. ID NO. 5), QRPAK(Gln-Arg-Pro-Ala-Lys) (SEQ. ID NO. 6), RPAK(Arg-Pro-Ala-Lys) (SEQ. ID NO. 3) or PAK(Pro-Ala-Lys), and the oligopeptide comprising an RGD sequence may be RGDS(Arg-Gly-Asp-Ser) (SEQ. ID NO. 11), RGDV(Arg-Gly-Asp-Val) (SEQ. ID NO. 12) or RGDF(Arg-Gly-Asp-Phe) (SEQ. ID NO. 13).

For the compound or pharmaceutical composition according to the present invention, high NO free radical-scavenging activity is demonstrated by in vivo rat models of NO free radical scavenging; superior thrombolysis and anti-thrombus activities are demonstrated by in vivo and in vitro experiments of thrombolysis and anti-thrombus; neuroprotective efficacy and superior anti-stroke activity are demonstrated by in vivo rat stroke models; and efficacy in decreasing cerebral infarction volume is demonstrated by rat stroke models.

DETAILED DESCRIPTION OF EMBODIMENTS

Figure 1:
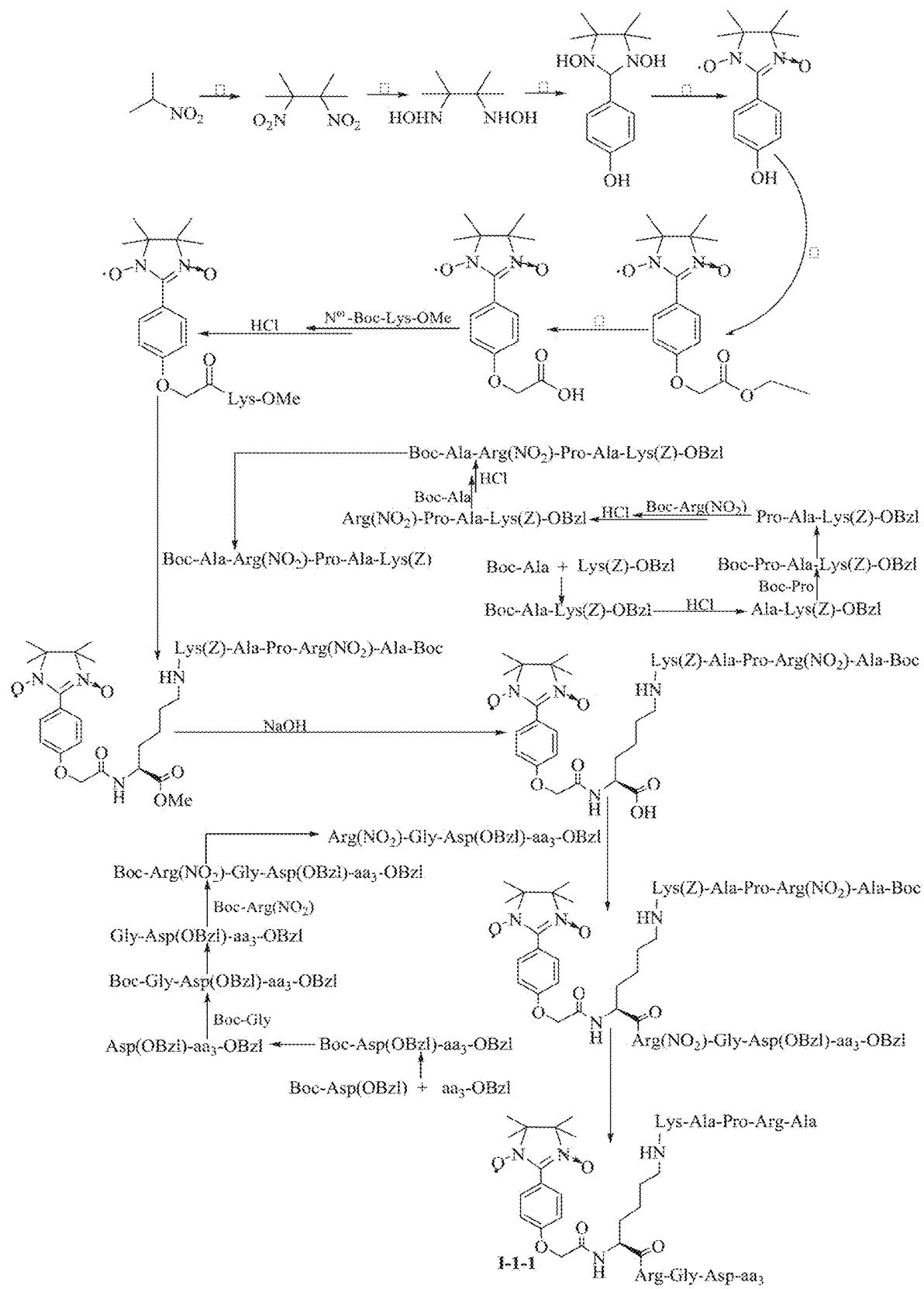
FIG. 1 shows a synthesis scheme for an embodiment of the compound according to the present invention (the compound of general formula I-1-1)
Figure 2:
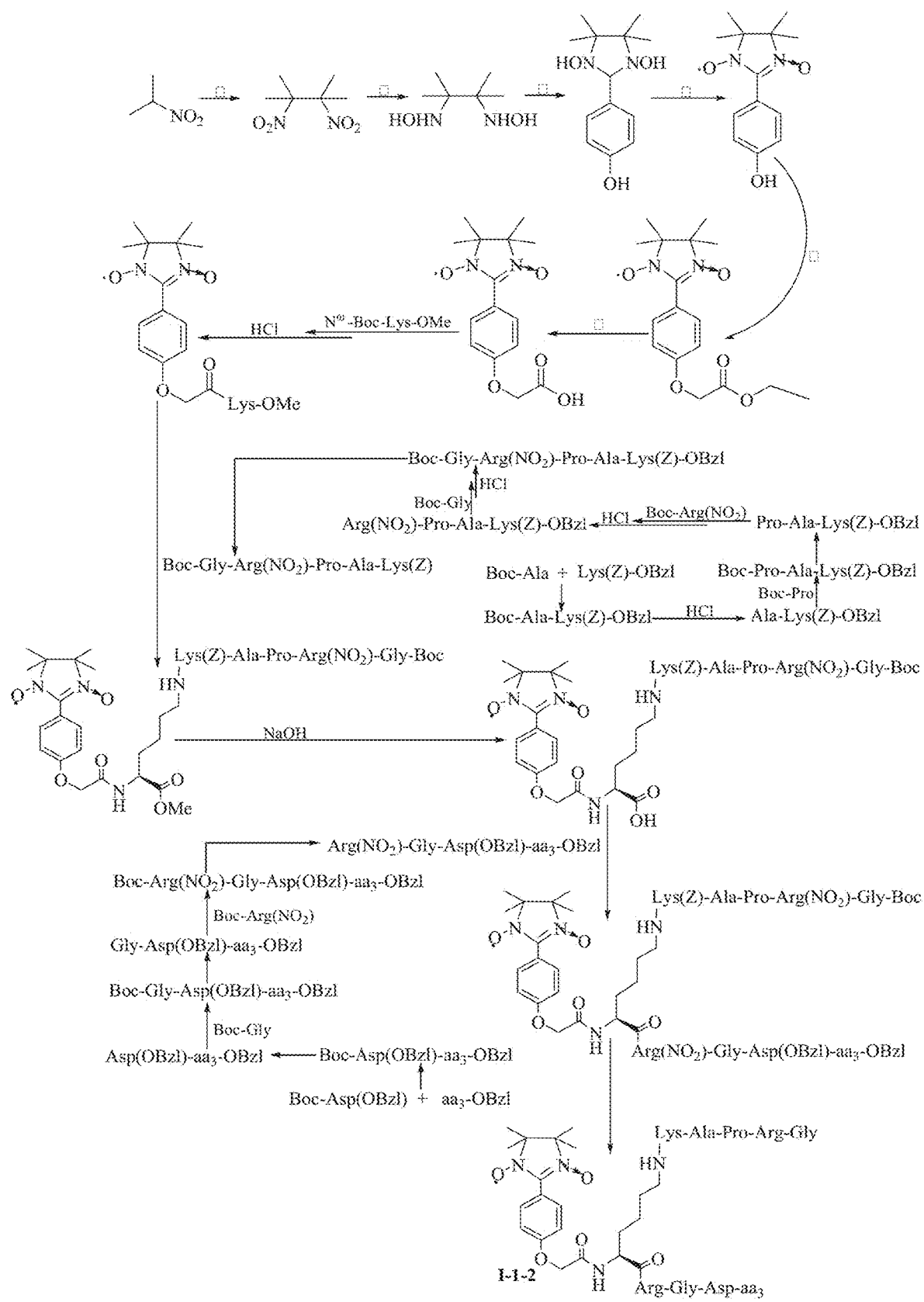
FIG. 2 shows a synthesis scheme for an embodiment of the compound according to the present invention (the compound of general formula I-1-2)
Figure 3:
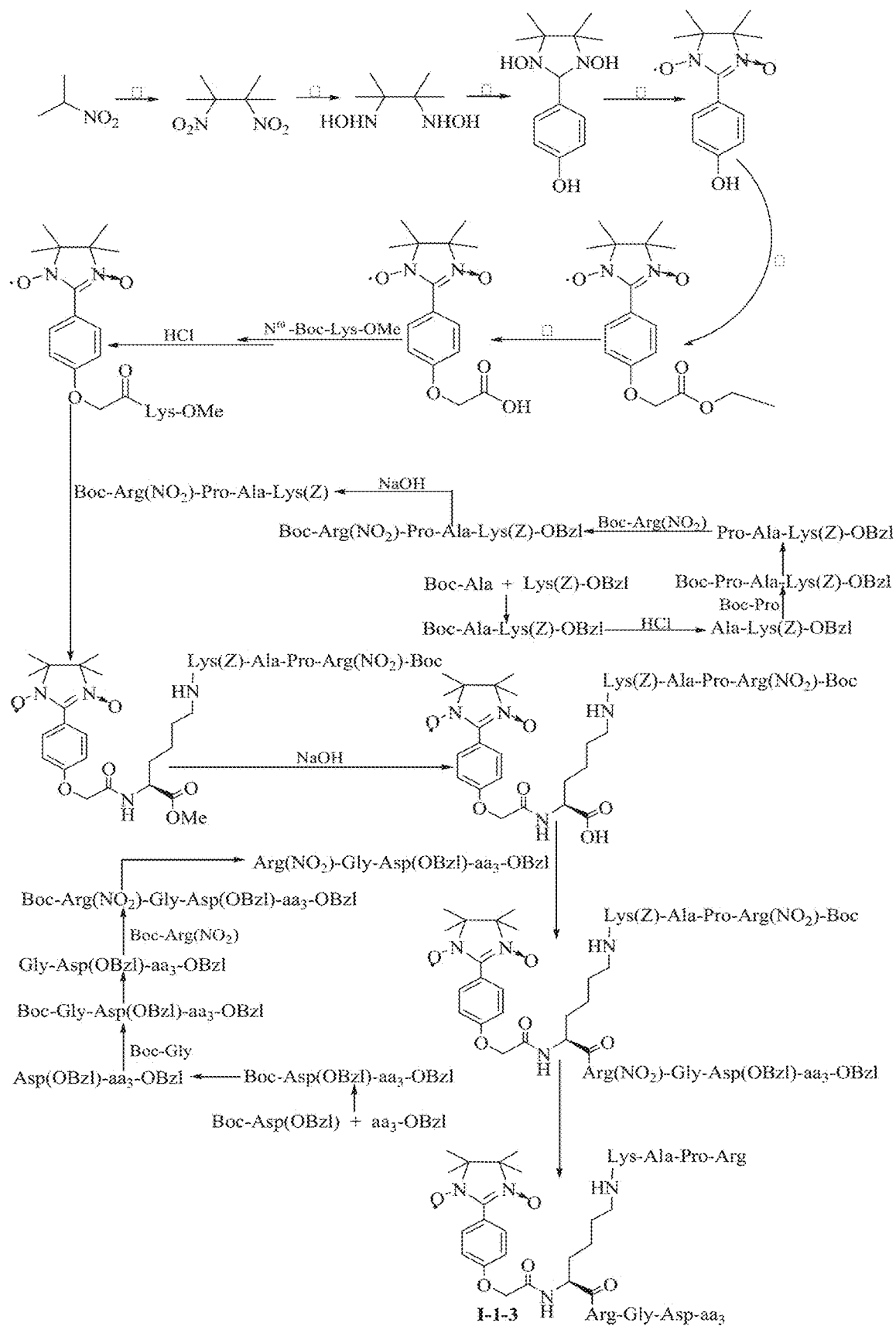
FIG. 3 shows a synthesis scheme for an embodiment of the compound according to the present invention (the compound of general formula I-1-3)
Figure 4:
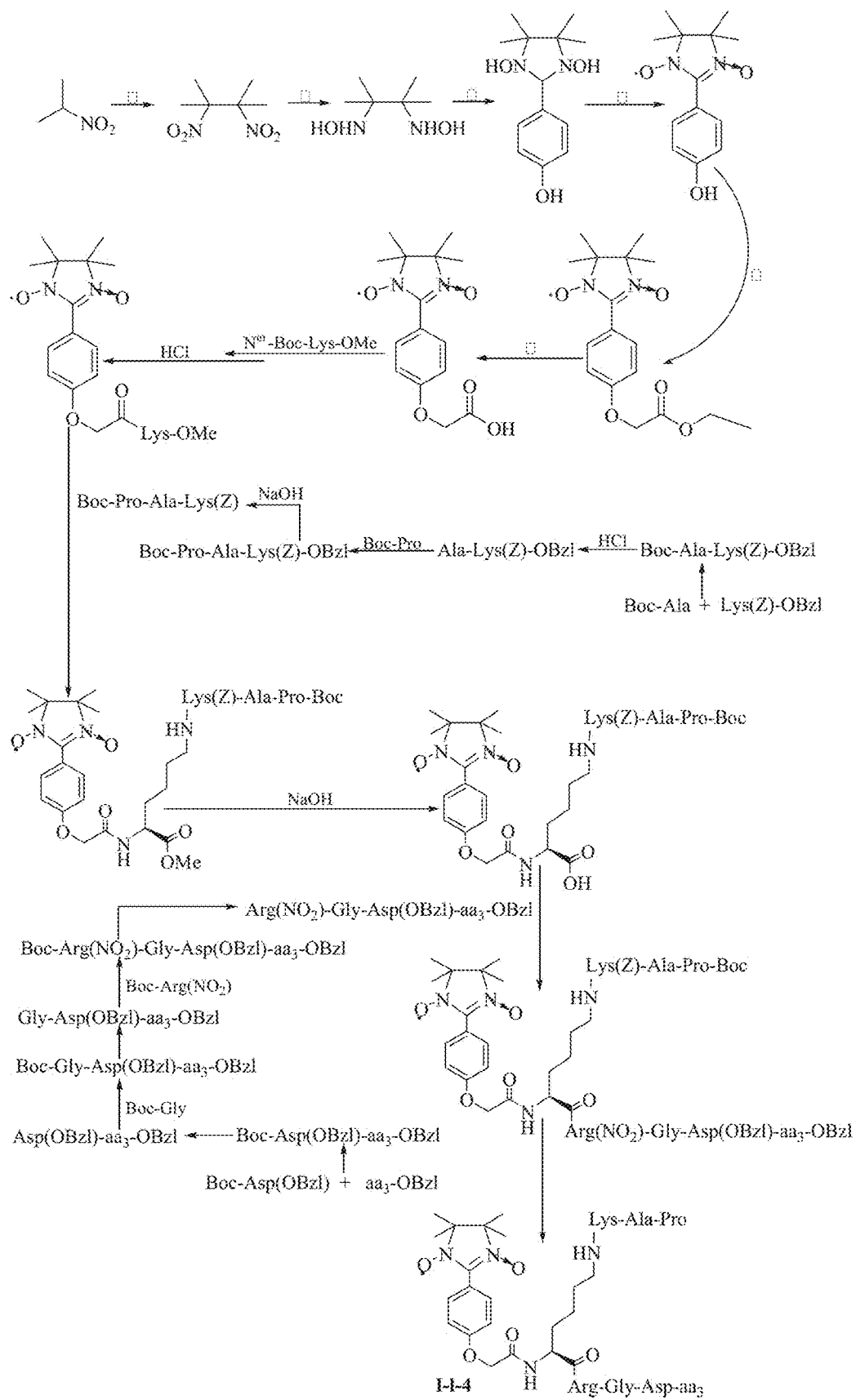
FIG. 4 shows a synthesis scheme for an embodiment of the compound according to the present invention (the compound of general formula I-1-4)
Figure 5:
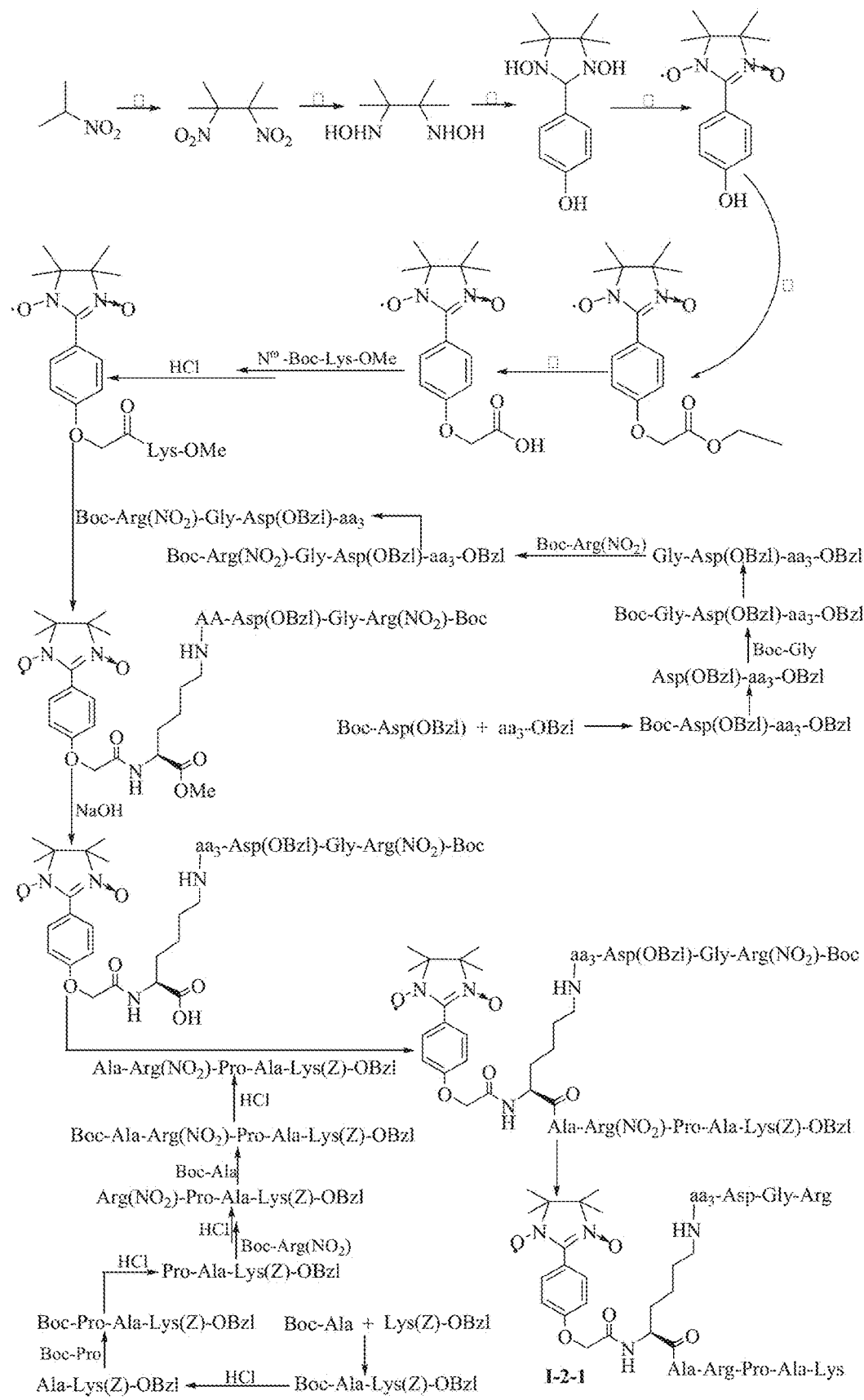
FIG. 5 shows a synthesis scheme for an embodiment of the compound according to the present invention (the compound of general formula I-2-1)
Figure 6:
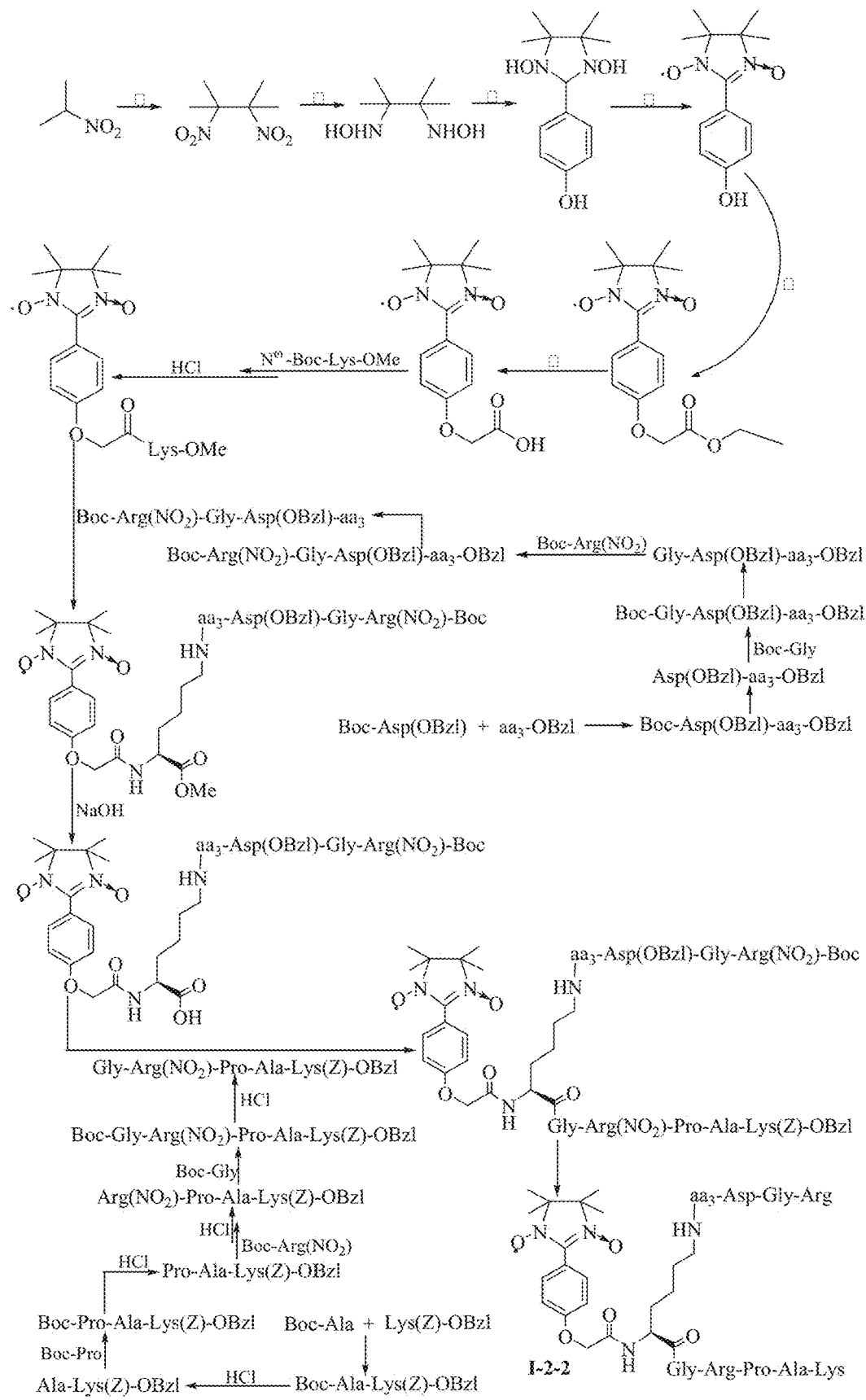
FIG. 6 shows a synthesis scheme for an embodiment of the compound according to the present invention (the compound of general formula I-2-2)
Figure 7:
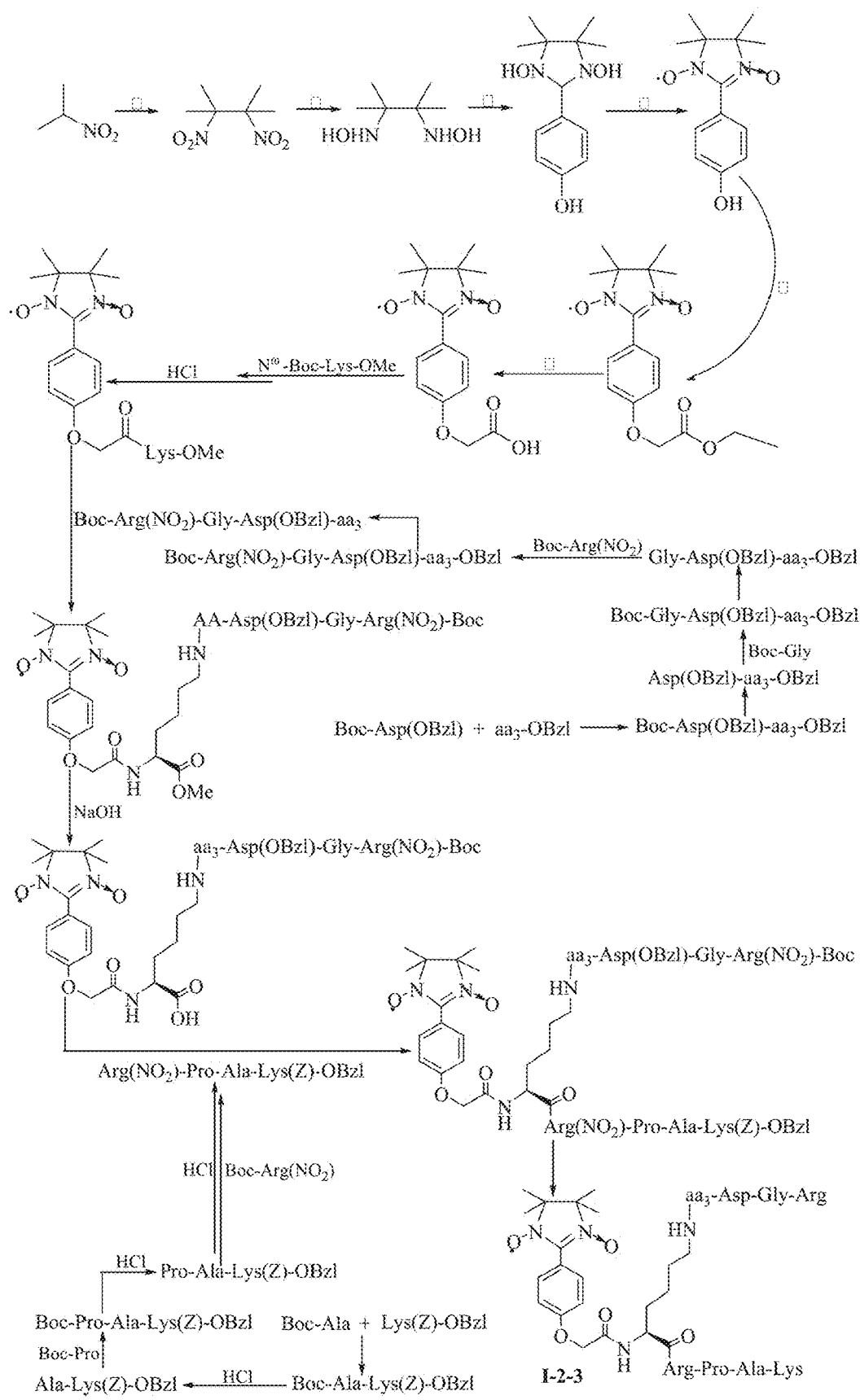
FIG. 7 shows a synthesis scheme for an embodiment of the compound according to the present invention (the compound of general formula I-2-3)
Figure 8:
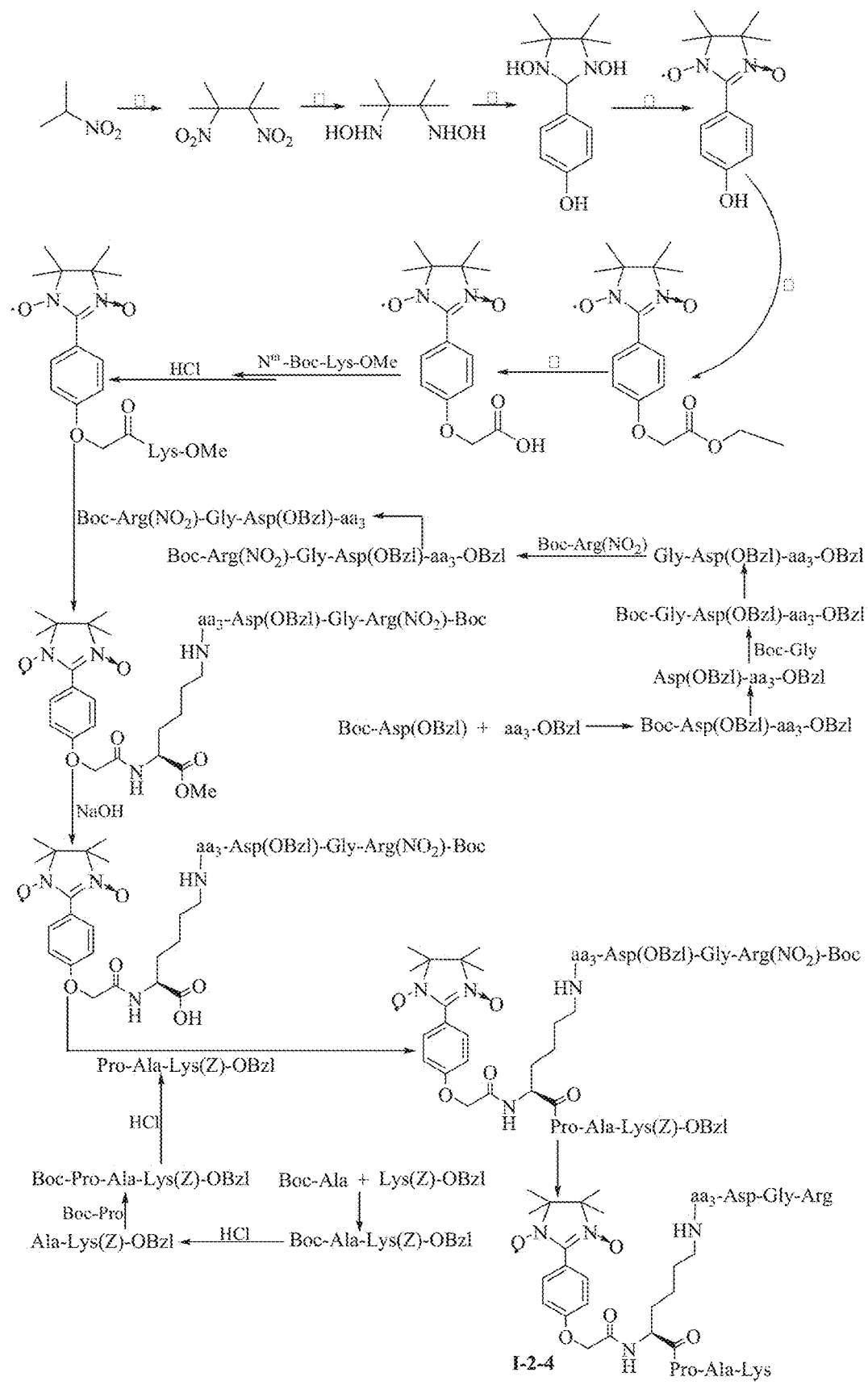
FIG. 8 shows a synthesis scheme for an embodiment of the compound according to the present invention (the compound of general formula I-2-4)
Figure 9:
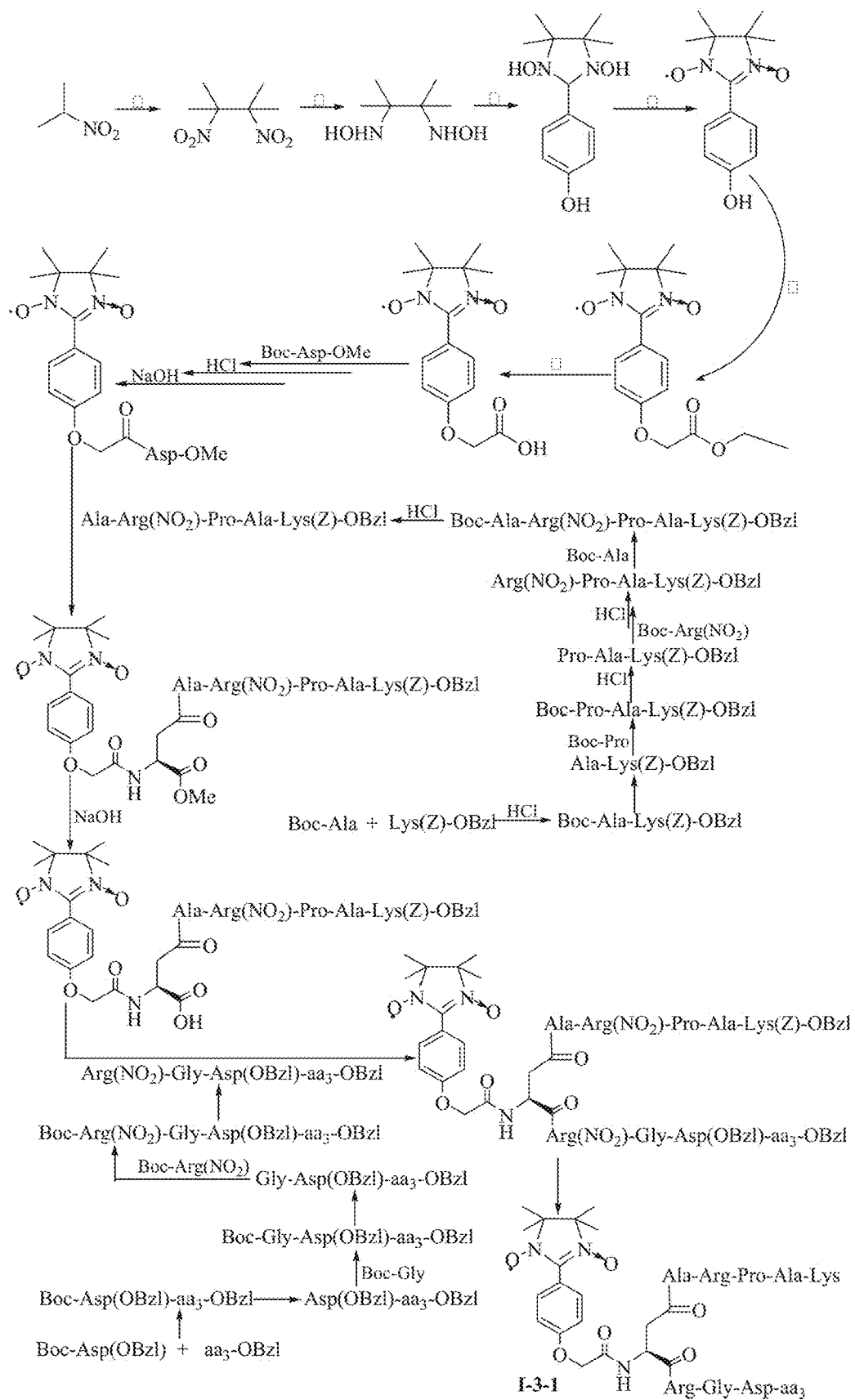
FIG. 9 shows a synthesis scheme for an embodiment of the compound according to the present invention (the compound of general formula I-3-1)
Figure 10:
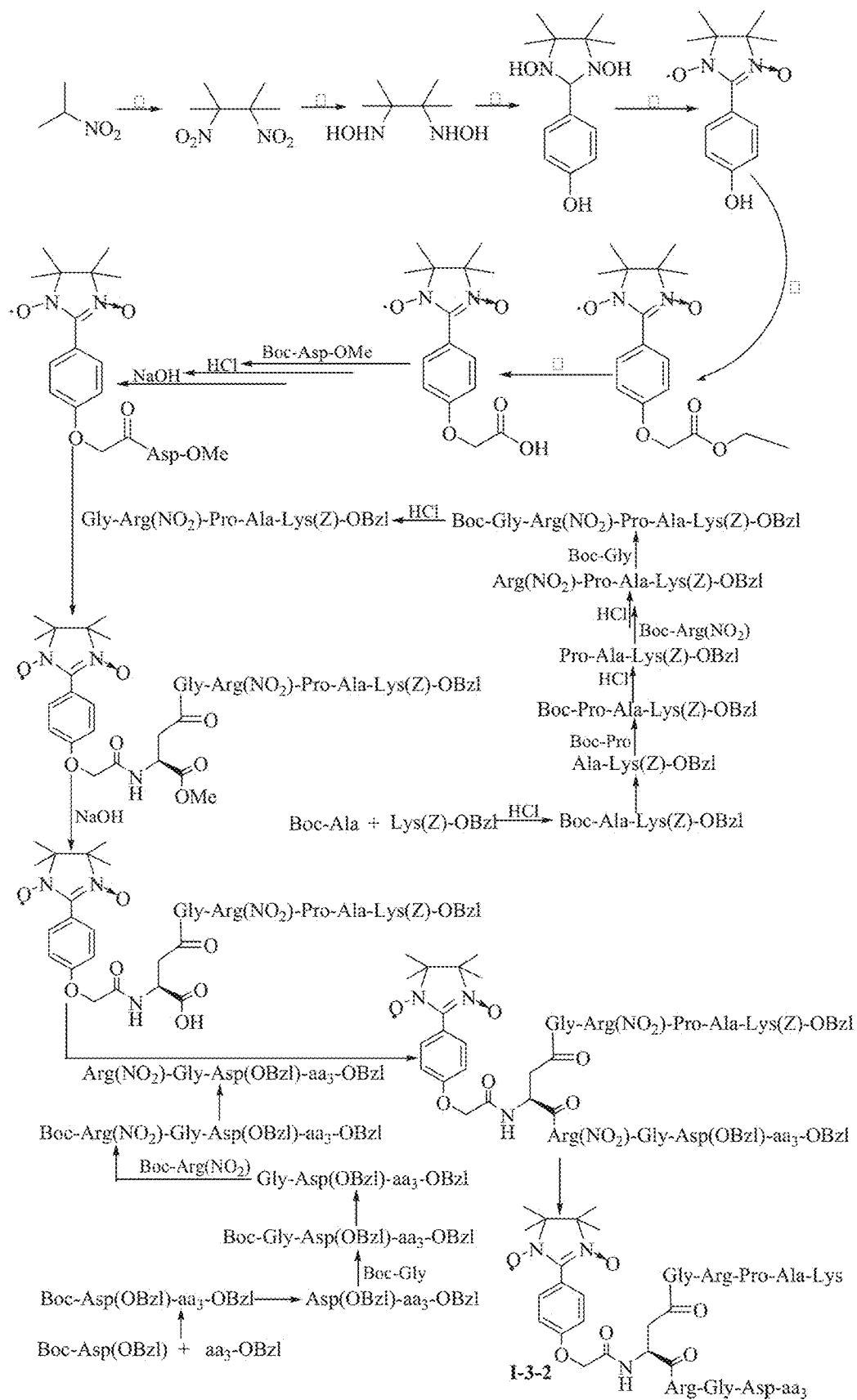
FIG. 10 shows a synthesis scheme for an embodiment of the compound according to the present invention (the compound of general formula I-3-2)
Figure 11:
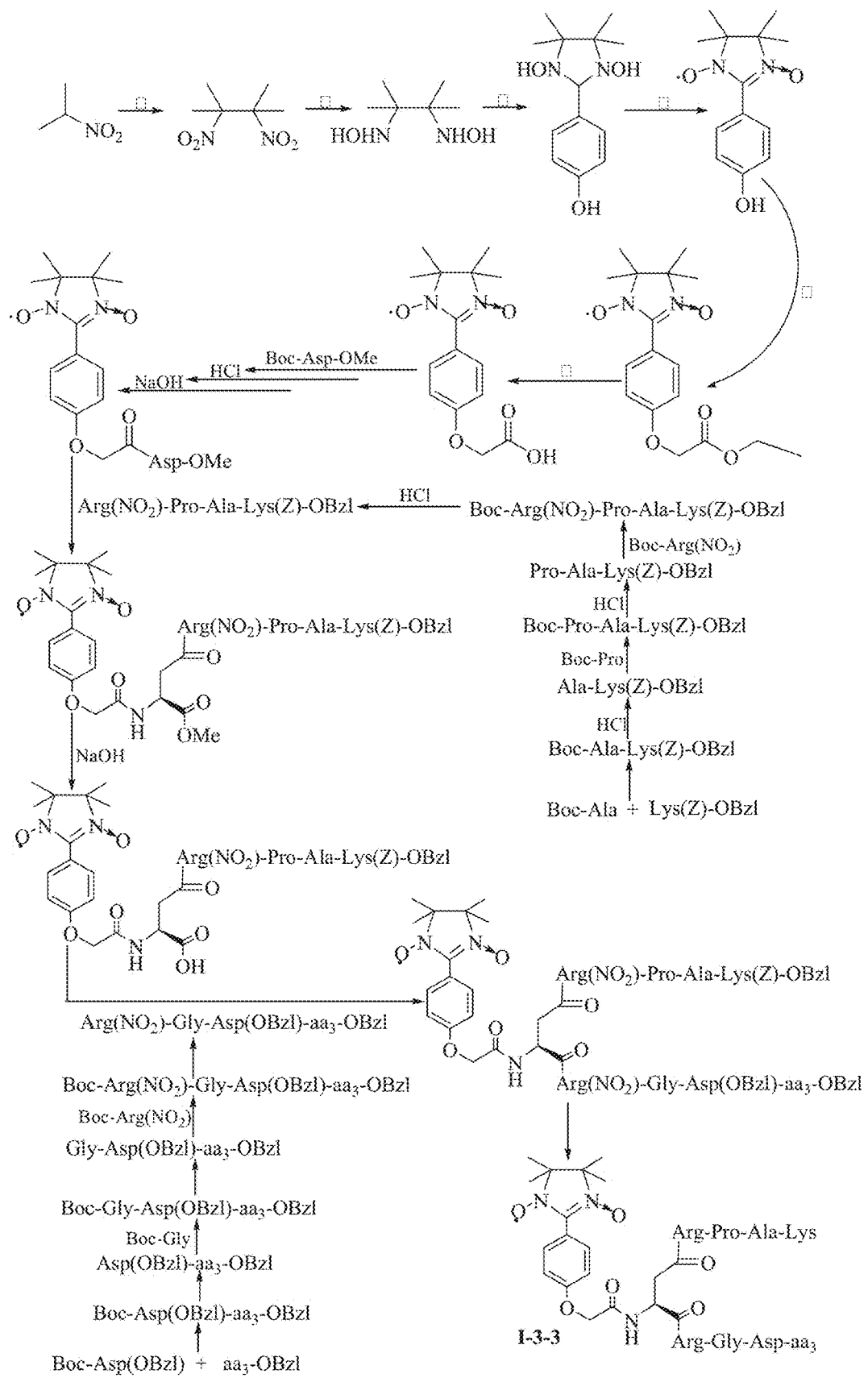
FIG. 11 shows a synthesis scheme for an embodiment of the compound according to the present invention (the compound of general formula I-3-3)
Figure 12:
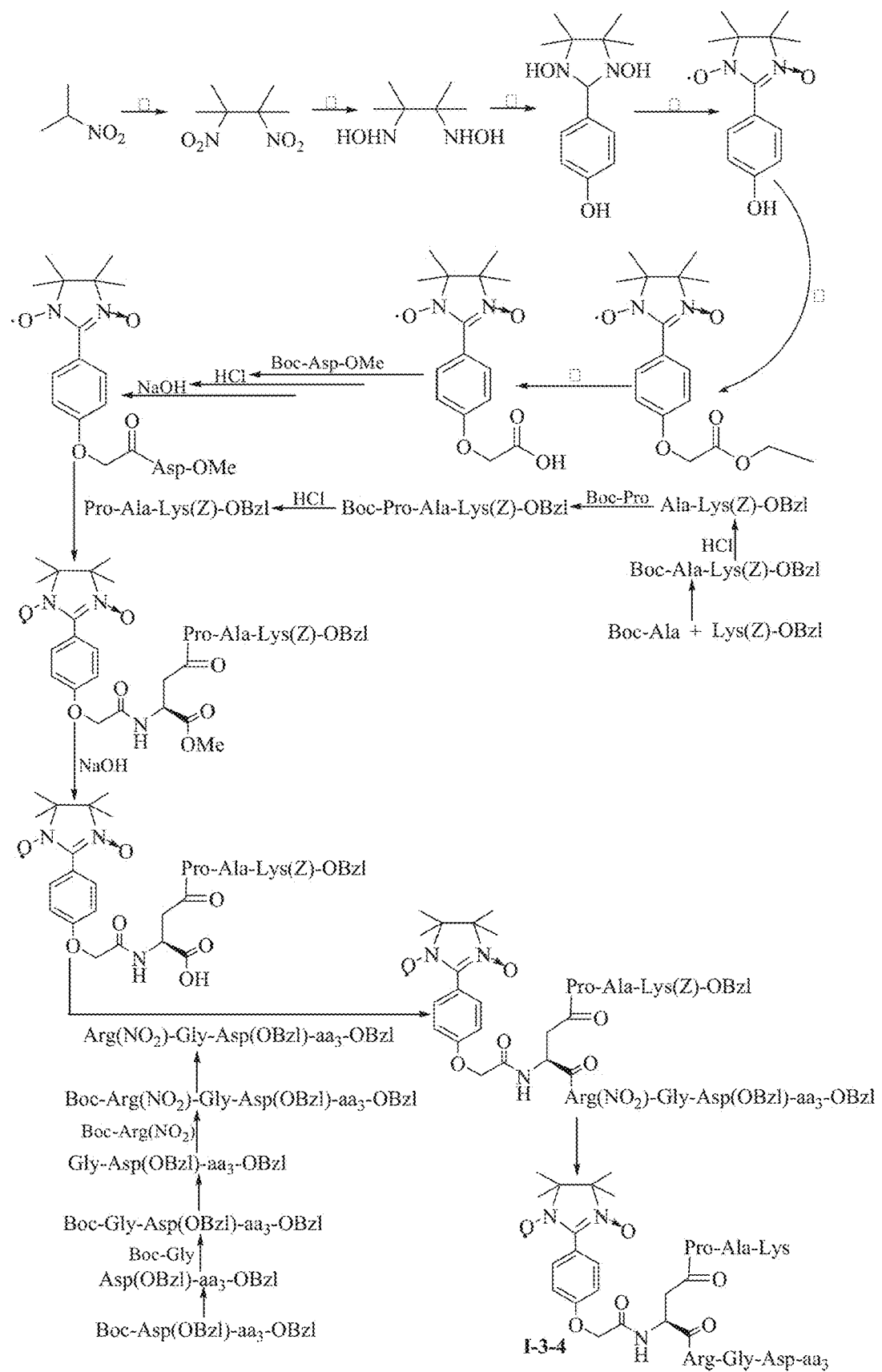
FIG. 12 shows a synthesis scheme for an embodiment of the compound according to the present invention (the compound of general formula I-3-4)
Figure 13:
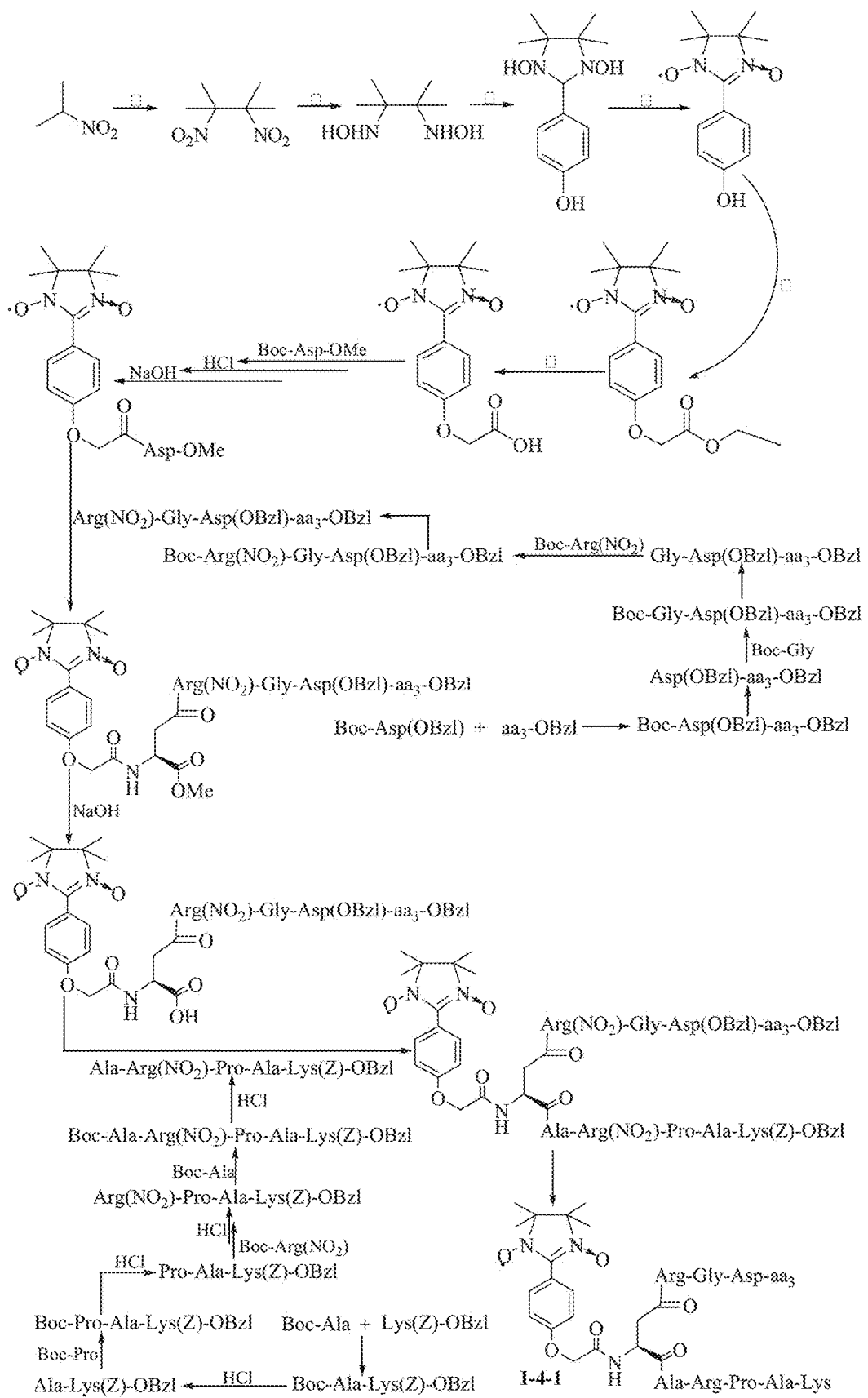
FIG. 13 shows a synthesis scheme for an embodiment of the compound according to the present invention (the compound of general formula I-4-1)
Figure 14:
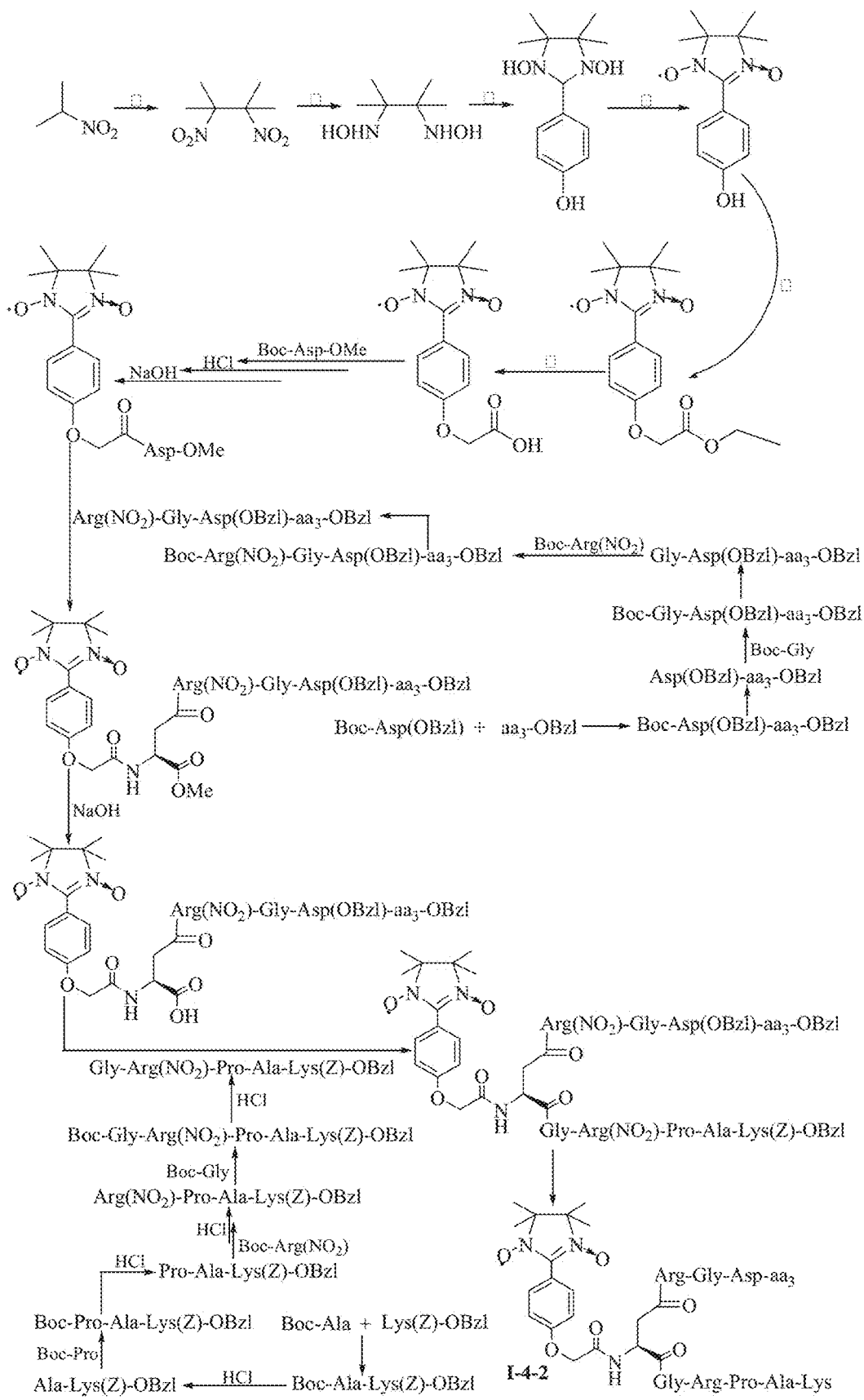
FIG. 14 shows a synthesis scheme for an embodiment of the compound according to the present invention (the compound of general formula I-4-2)
Figure 15:
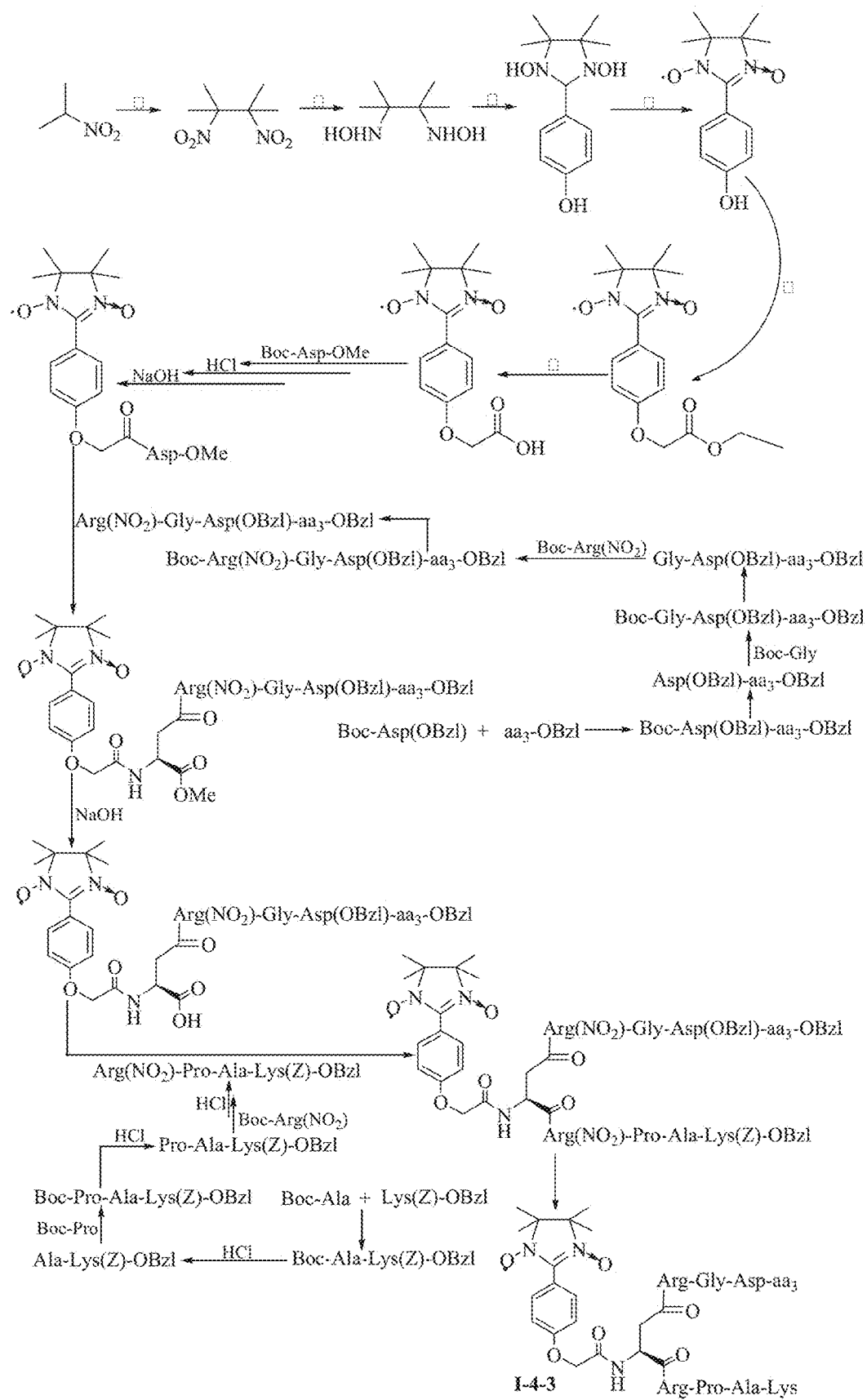
FIG. 15 shows a synthesis scheme for an embodiment of the compound according to the present invention (the compound of general formula I-4-3)
Figure 16:
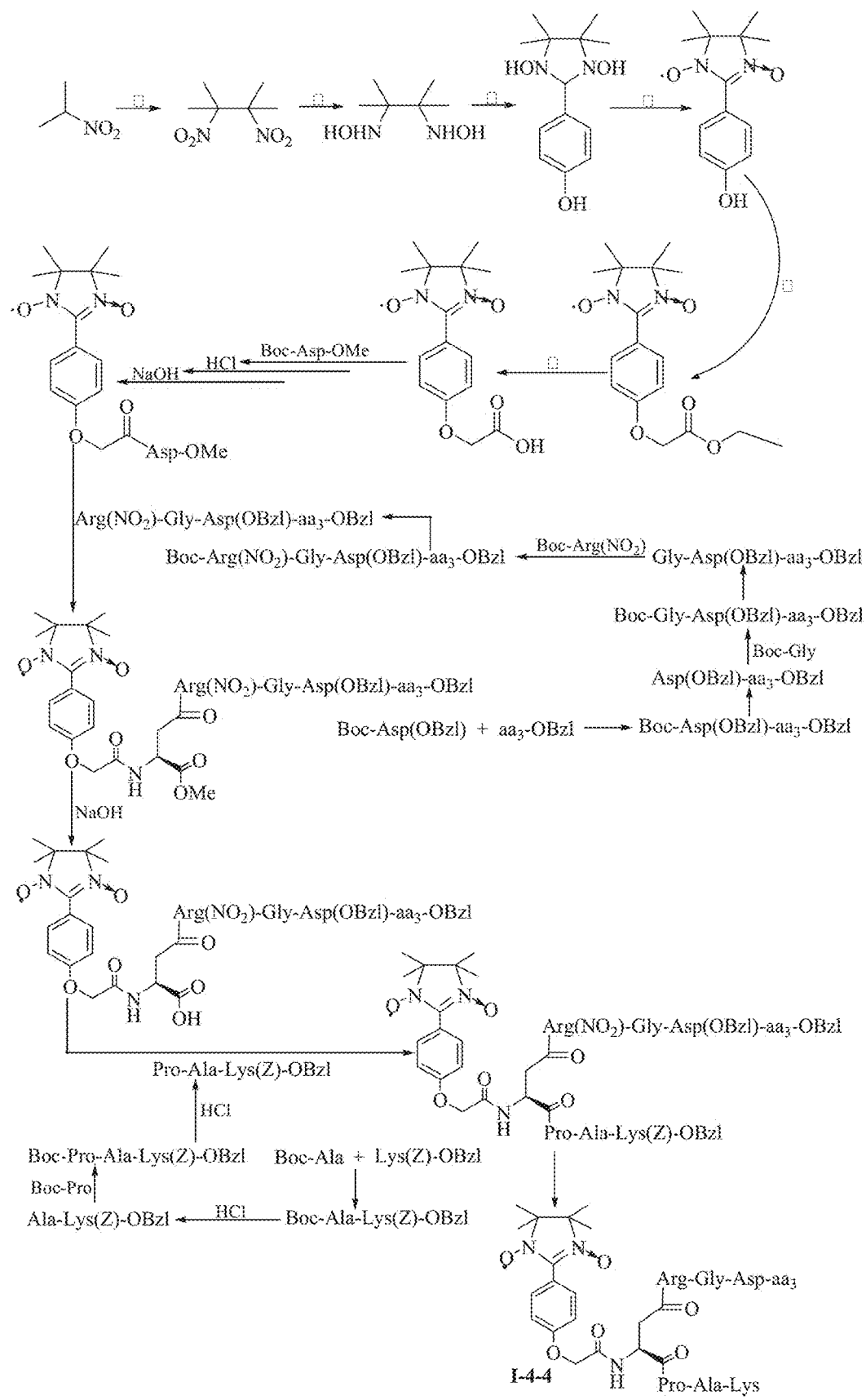
FIG. 16 shows a synthesis scheme for an embodiment of the compound according to the present invention (the compound of general formula I-4-4)
Figure 17:
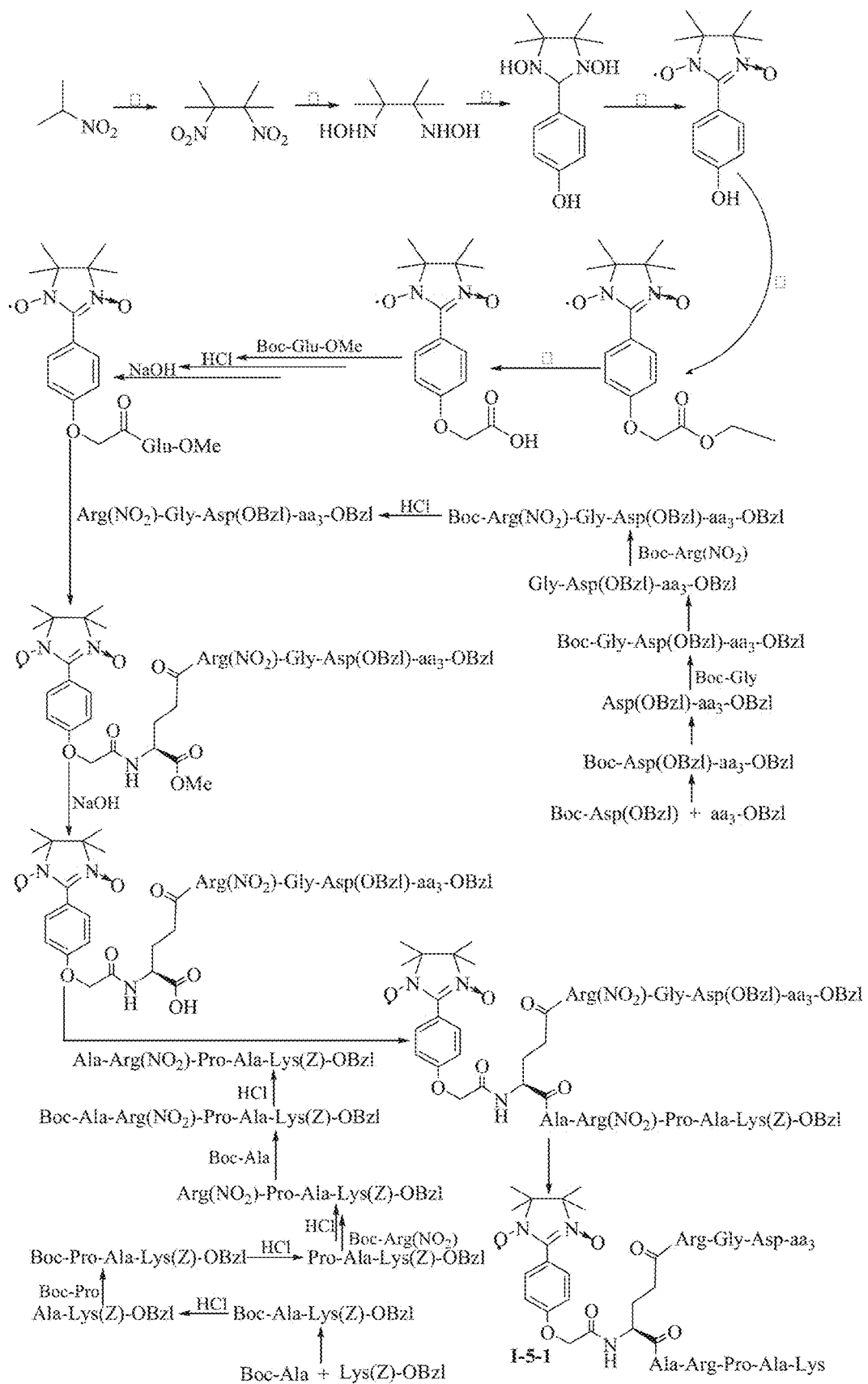
FIG. 17 shows a synthesis scheme for an embodiment of the compound according to the present invention (the compound of general formula I-5-1)
Figure 18:
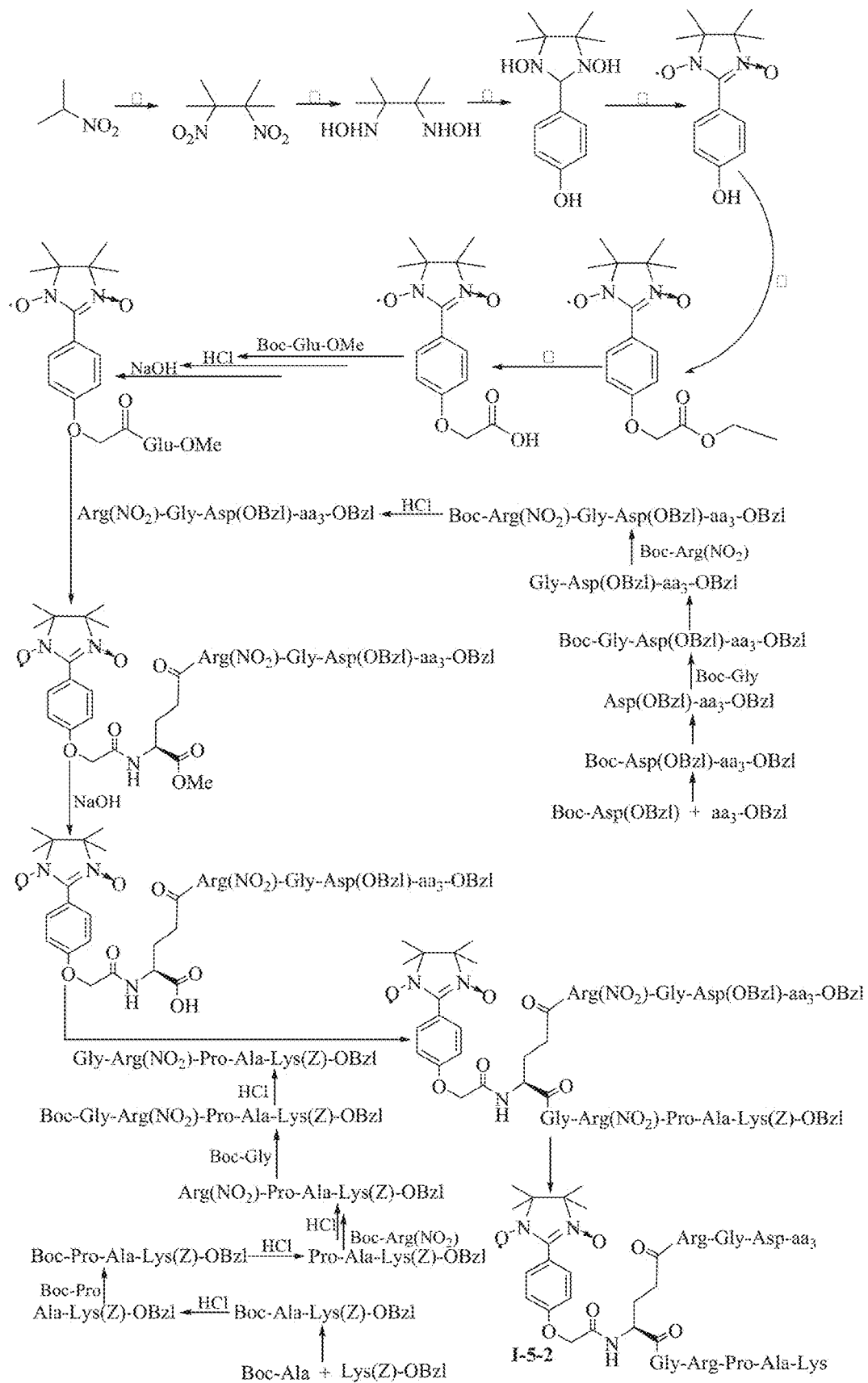
FIG. 18 shows a synthesis scheme for an embodiment of the compound according to the present invention (the compound of general formula I-5-2)
Figure 19:
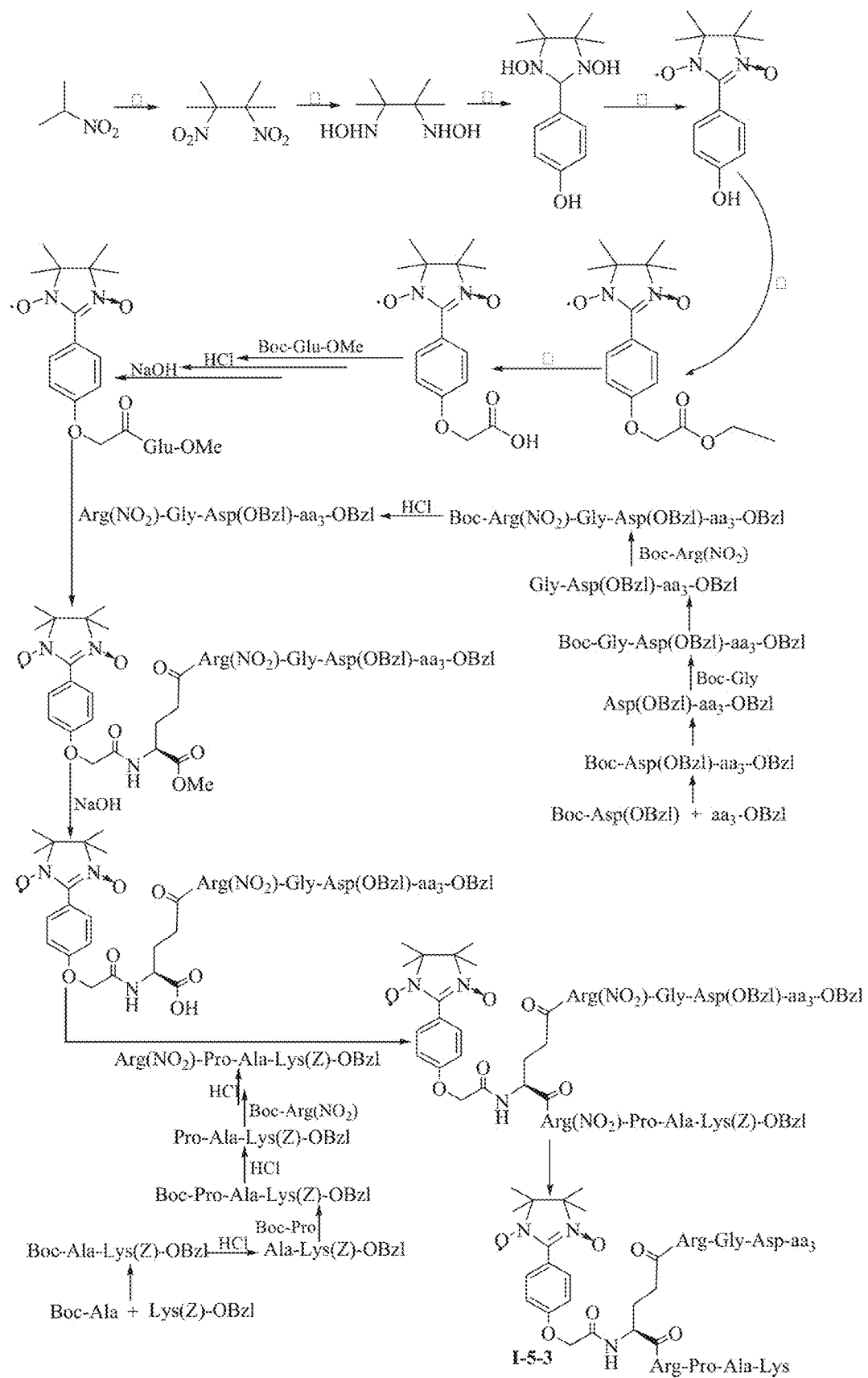
FIG. 19 shows a synthesis scheme for an embodiment of the compound according to the present invention (the compound of general formula I-5-3)
Figure 20:
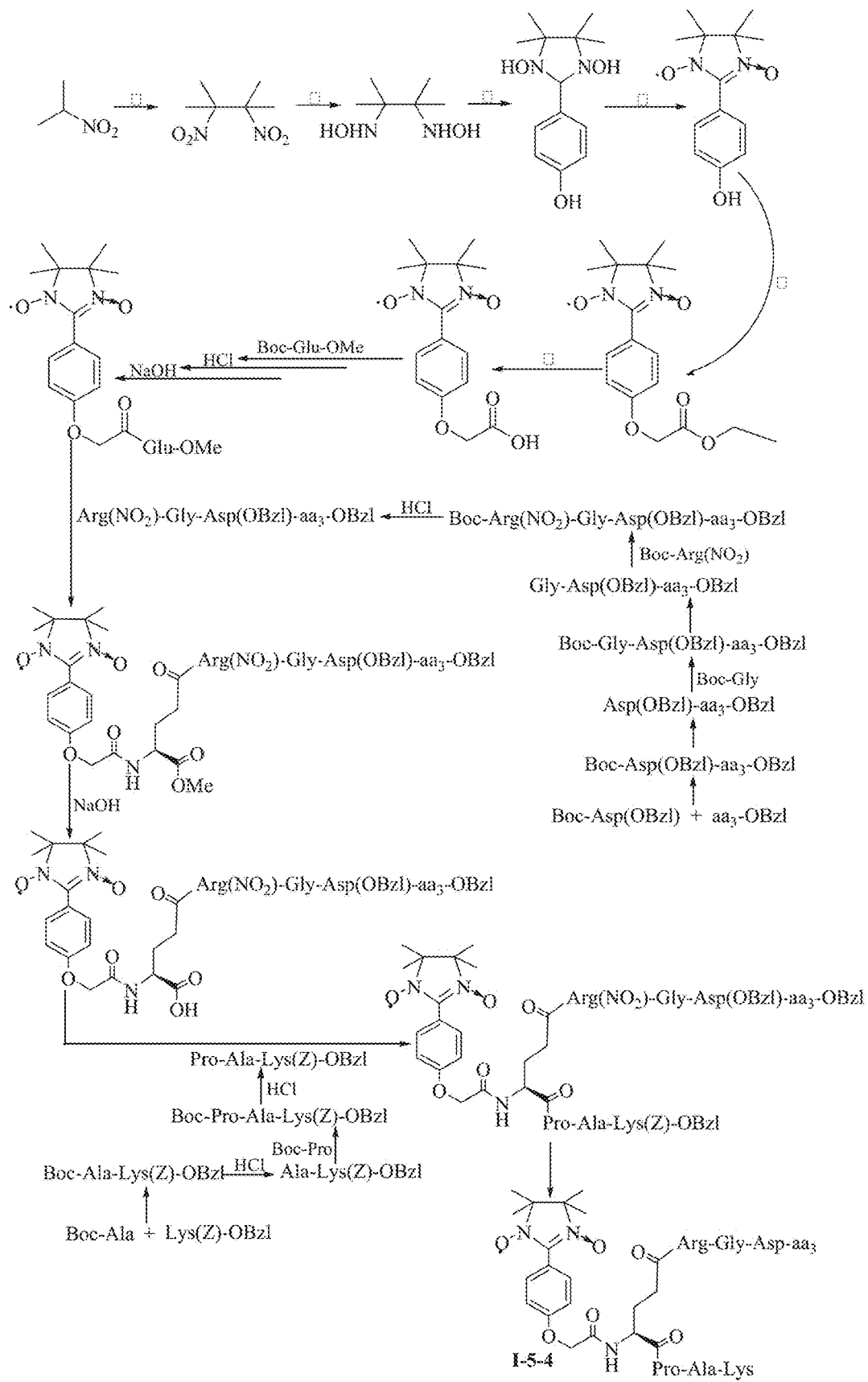
FIG. 20 shows a synthesis scheme for an embodiment of the compound according to the present invention (the compound of general formula I-5-4)
Figure 21:
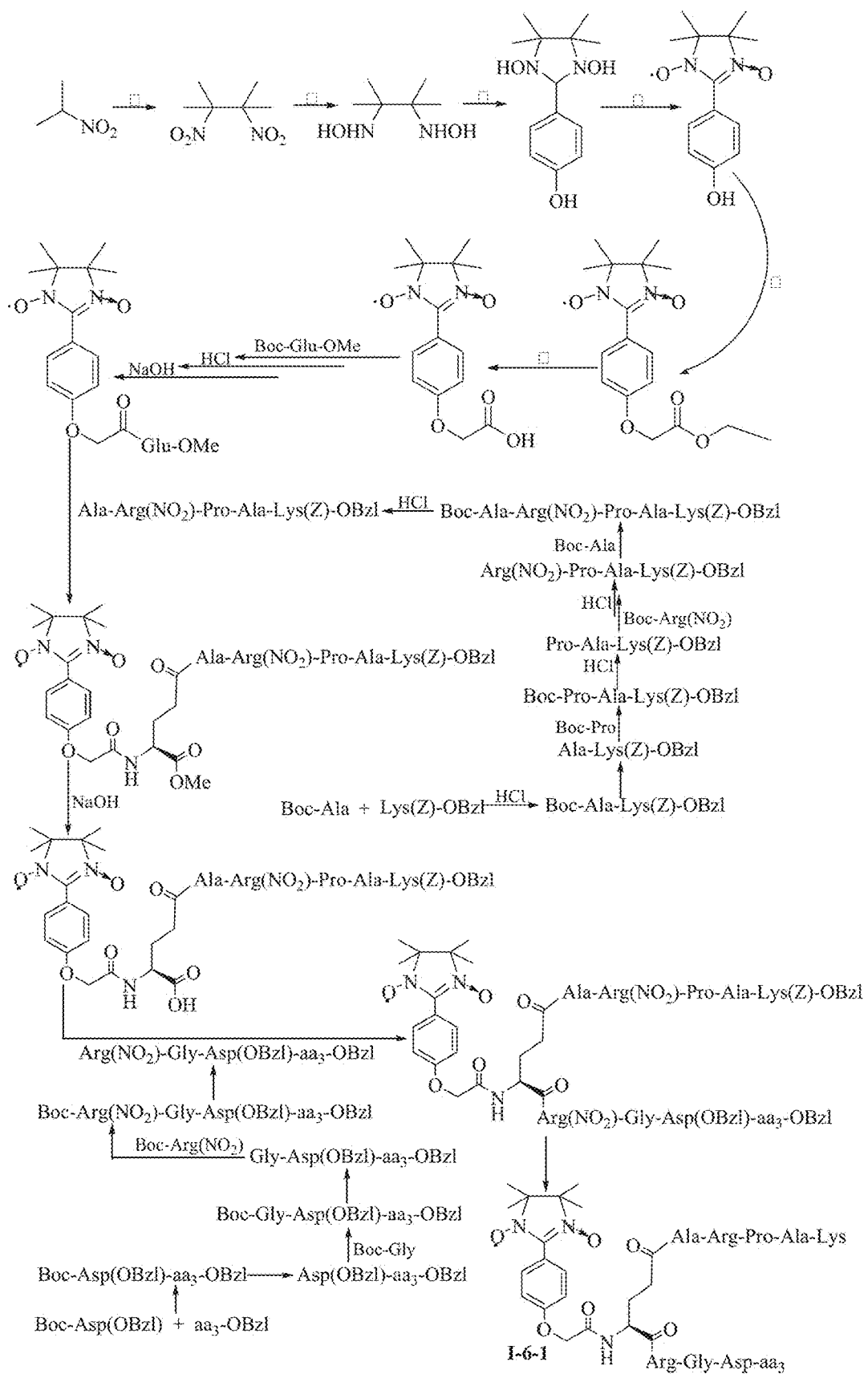
FIG. 21 shows a synthesis scheme for an embodiment of the compound according to the present invention (the compound of general formula I-6-1)
Figure 22:
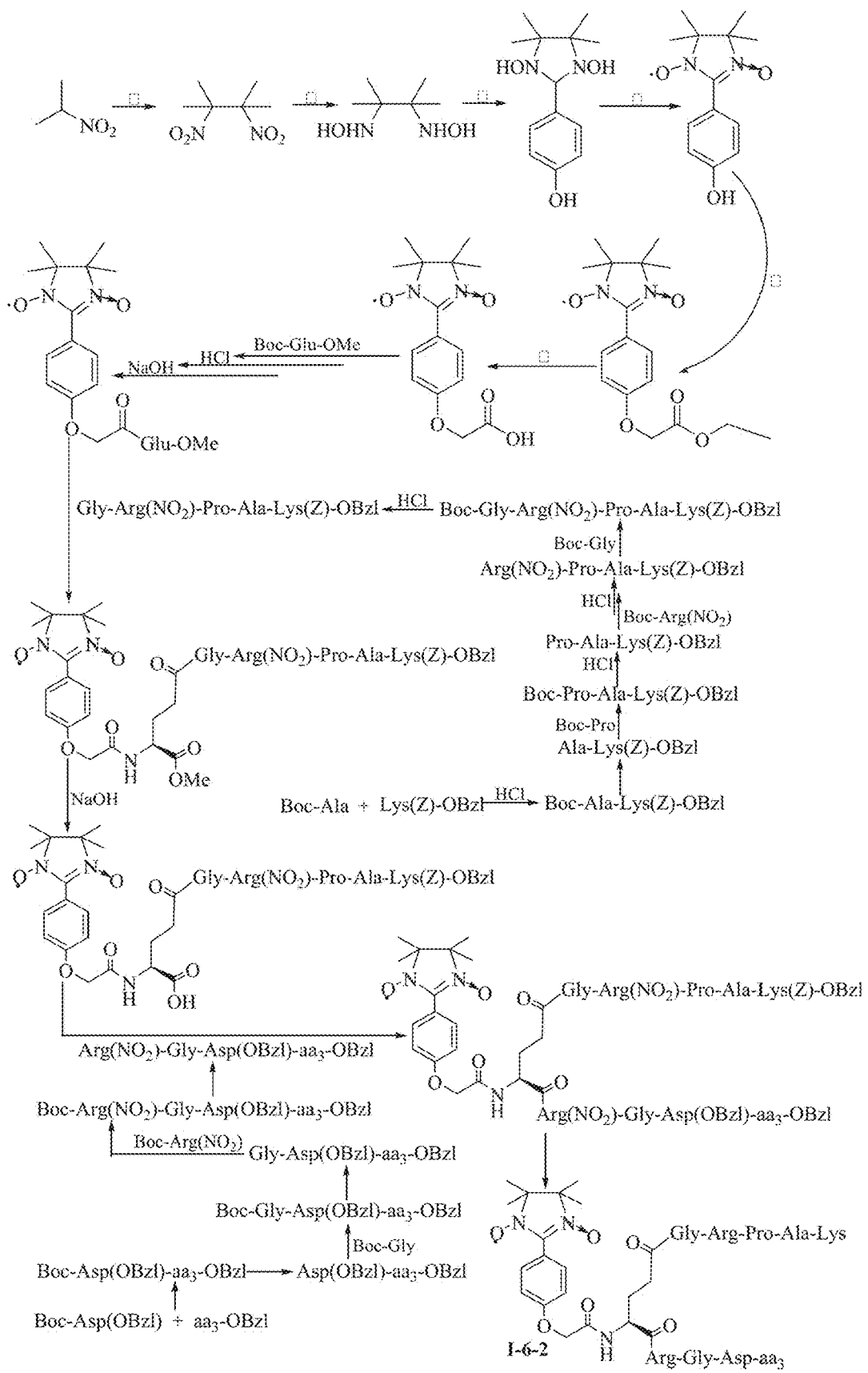
FIG. 22 shows a synthesis scheme for an embodiment of the compound according to the present invention (the compound of general formula I-6-2)
Figure 23:
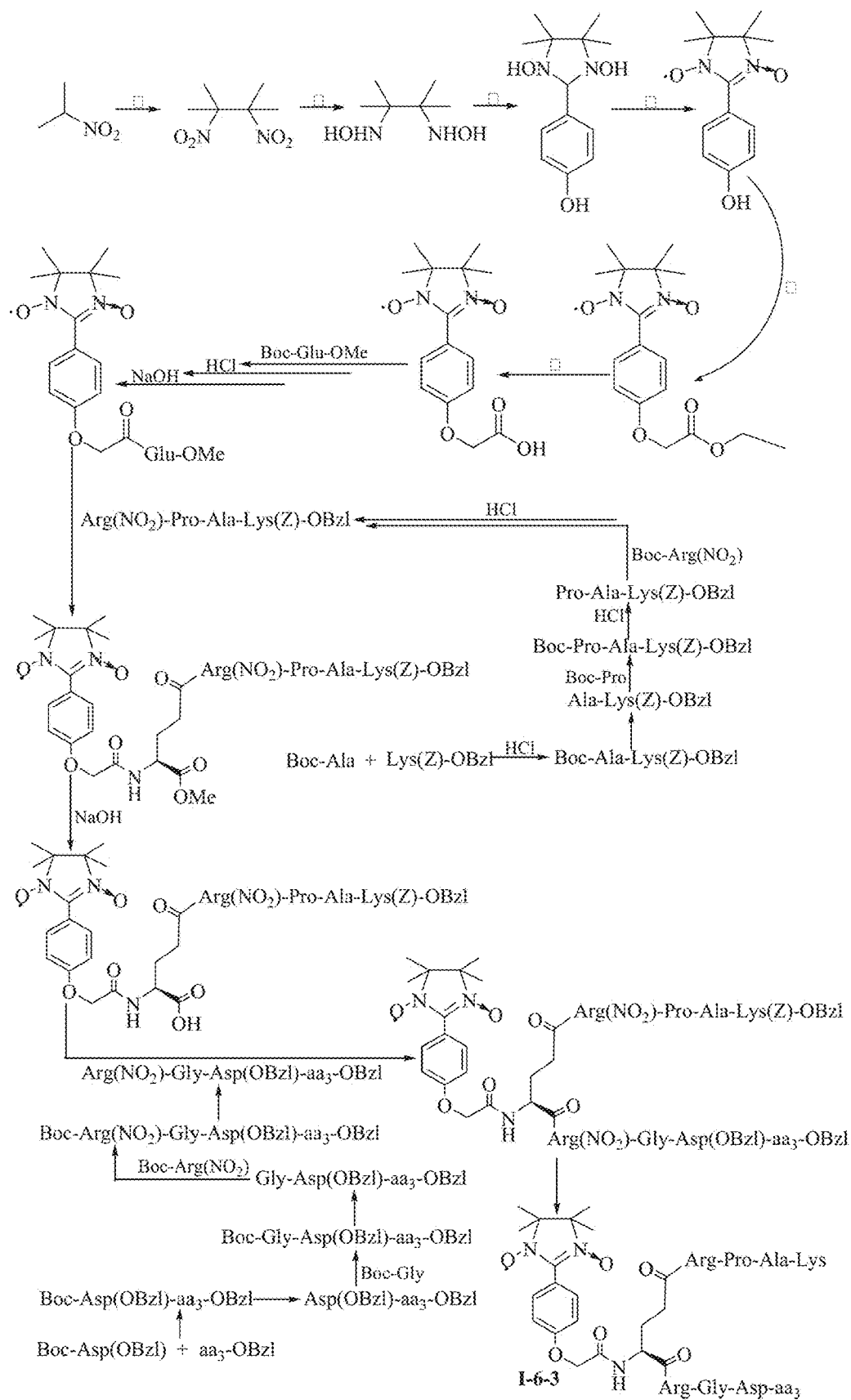
FIG. 23 shows a synthesis scheme for an embodiment of the compound according to the present invention (the compound of general formula I-6-3)
Figure 24:
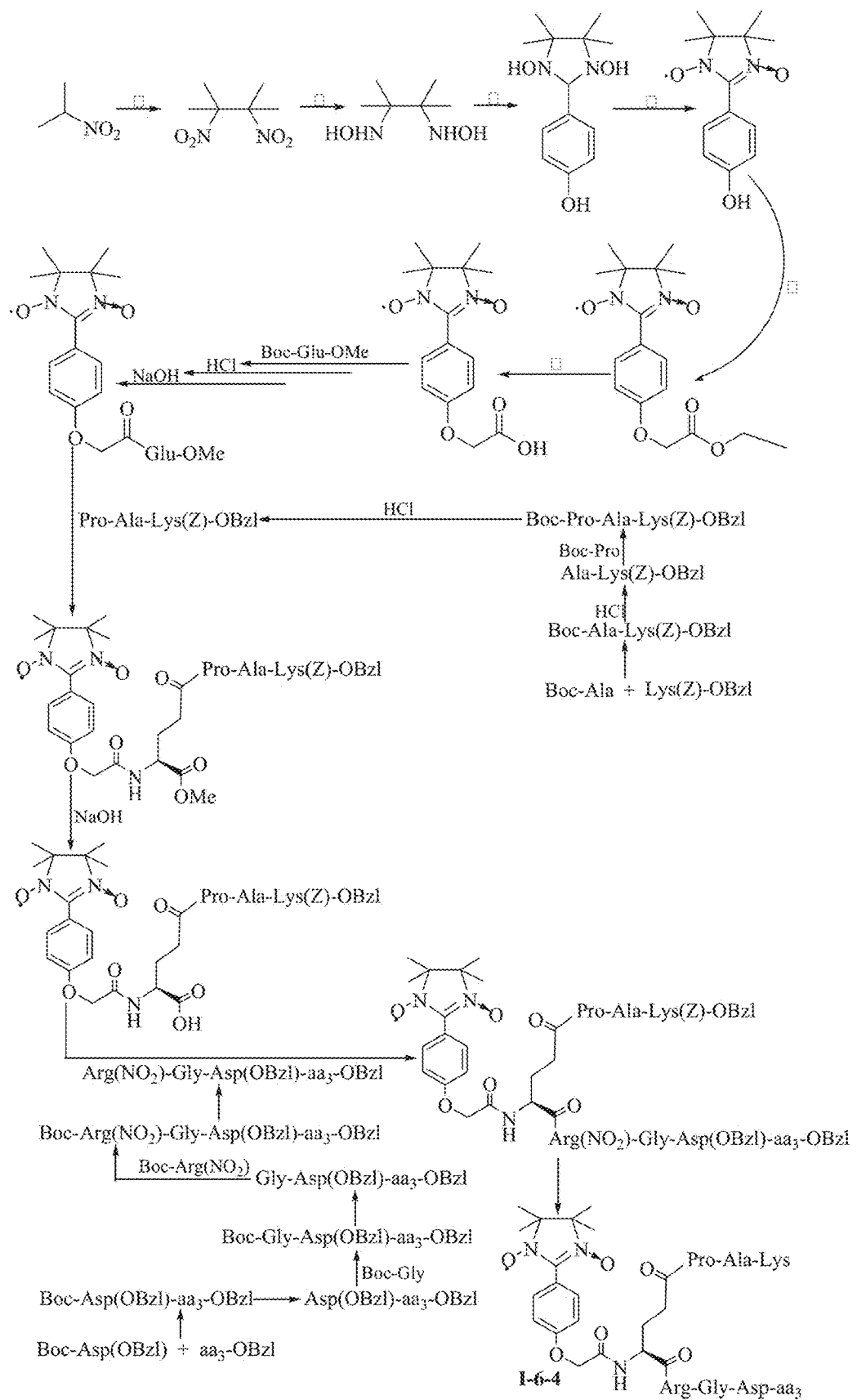
FIG. 24 shows a synthesis scheme for an embodiment of the compound according to the present invention (the compound of general formula I-6-4)

The present invention will now be described in connection with the following specific examples, and the advantages and features thereof will become apparent in view of the description. These examples are merely illustrative and in no way limit the scope of the present invention. A person skilled in the art can understand that modification or substitution may be made in details and formality of the technical solutions of the present invention without deviating from the spirit and scope of the present invention, and these modifications or substitutions are intended to be within the scope of protection of the present invention.

Preparation of Imidazolines Having NO Free Radical Scavenging Activity: 1,3-Dioxo-2-[(4-Oxyacetoxy)Phenyl]-4,4,5,5-Tetramethylimidazoline

Example 1. Preparation of 2,3-dimethyl-2,3-dinitrobutane 69 g (0.78 mol) 2-nitropropane was added to a 130 ml aqueous solution of NaOH (6N). 20 ml (0.38 mol) $Br_2$ was added dropwise under stirring on an ice salt bath within 1 h. After completion of $Br_2$ addition, 240 mL ethanol was added thereto and refluxed at 90° C. for 3 h. The reaction solution, while still hot, was instantly poured into 800 ml ice water, and then filtered to afford 55 g of the title compound (81%) as a colorless flaky crystal, Mp 110-112° C.

Example 2. Preparation of 2,3-dimethyl-2,3-dihydroxyaminobutane 7 g (40 mmol) 2,3-dimethyl-2,3-dinitrobutane and 4 g $NH_4Cl$ were mixed and suspended in a 80 mL aqueous solution of ethanol (50%) and stirred on ice bath, into which 16 g zinc powder was added within 3 h. After the addition of zinc powder was completed, the ice bath was removed, and the reaction continued for 3 h at room temperature (RT) under stirring, and then the reaction mixture was vacuum filtered. The filter cake was washed repeatedly with ethanol aqueous solution (50%). The filtrate and the washing liquid were combined, adjusted to pH=2 with conc. HCl, and then distilled under reduced pressure into a slurry. After addition of an appropriate amount of potassium carbonate, the slurry was evenly mixed and extracted for 6 h by using a Soxhlet extractor with chloroform as the extractant. The extract was concentrated under reduced pressure into a small amount, into which petroleum ether was added to precipitate 2.60 g of the title compound (44%) as a colorless crystal, Mp 157-159° C.

Example 3. Preparation of 1,3-dihydroxy-2-(4'-hydroxyphenyl)-4,4,5,5-tetramethylimidizolidine 1.22 g (10 mmol) p-hydroxy benzaldehyde and 1.48 g (10 mmol) 2,3-dimethyl-2,3-dihydroxyaminobutane were dissolved in 10 mL methanol and stirred at RT for 8 h until the starting material spot disappeared as shown by TLC. Upon vacuum filtration, 1.29 g (51%) title compound was obtained as a colorless crystal. EI-MS (m/z) 252 $[M]^+$. $^1$H-NMR (DMSO-$d_6$) δ (ppm)=1.03 (s, 6H), 1.05 (s, 6H), 4.39 (s, 1H), 6.70 (d, J=6.9 Hz, 2H), 7.23 (d, J=6.9 Hz, 2H), 7.63 (s, 1H), 7.85 (s, 2H).

Example 4. Preparation of 1,3-dihydroxy-2-(4'-hydroxyphenyl)-4,4,5,5-tetramethylimidazoline 504 mg (2 mmol) 1,3-dihydroxy-2-(4'-hydroxyphenyl)-4,4,5,5-imidizolidine were dissolved in 30 mL methanol followed by addition of 3 g $PbO_2$, and stirred at RT for 40 min until the starting material spot disappeared as shown by TLC. After removal of solids by vacuum filtration, the filtrate was distilled until dry under reduced pressure at RT, and the residue was purified by column chromatography (with chloroform as the eluent) to afford 260 mg (52%) of the title compound as blue solid. Mp 134-135° C., EI-MS (m/z) 249 $[M]^+$. IR (KBr) 3250, 1610, 1500, 1490, 840.

Example 5. Preparation of 1,3-dioxo-2-(4'-(oxyacetate ethyl ester)-phenyl)-4,4,5,5-tetramethylimidazoline 250 mg (1 mmol) 1,3-dihydroxy-2-(4'-hydroxyphenyl)-4,4,5,5-tetramethylimidazoline, 0.32 mL ethyl bromoacetate and 32 mg NaH were dissolved in 5 mL anhydrous THF. The mixture was stirred at 60° C. for 5 h until the starting material spot disappeared as shown by TLC. After filtration under reduced pressure at RT, the filtrate was concentrated under reduced pressure till dry, and the residue was purified by column chromatography (ethyl acetate:petroleum ether=1:5) to give 300 mg (90%) of the target compound, MP 107-109° C.

Example 6. Preparation of 1,3-dioxo-2-(4'-oxyacetoxy-phenyl)-4,4,5,5-tetramethylimidazoline (TMMZ)

7 drops of a NaOH (2N) aqueous solution was added into a solution of 33 mg (0.1 mmol) 1,3-dioxo-2-(4'-(oxyacetate ethyl ester)-phenyl)-4,4,5,5-tetramethylimidazoline in 3 mL methanol, followed by stirring at RT for 30 min until the starting material spot disappeared as shown by TLC. The reaction mixture was concentrated under reduced pressure, and the residue was diluted by addition of 2 mL saturated saline, adjusted to pH 6 with 2N HCl, and then extrated 3 times with ethyl acetate (3 ml×3). The layers of ethyl acetate phase were combined and dried over anhydrous sodium sulfate and then filtered. The filtrate was concentrated under reduced pressure at RT till dry to afford 30 mg (99%) of the title compound as blue crystal. Mp 155-157° C. EI-MS (m/z) 307 [M]⁺.

Coupling the Imidazolines Having NO Free Radical Scavenging Activity with a Linking Arm: 1,3-Dioxo-2-[(4'-Oxyacetyl-Lys-OMe)Phenyl]-4,4,5,5-Tetramethylimidazoline

Example 7. Preparation of 1,3-dioxo-2-[(4'-oxyacetyl-NO-Boc-Lys-OMe)phenyl]-4,4,5,5-tetramethylimidazoline A solution of 307 mg (1 mmol) 1,3-dioxo-2-(4'-oxyacetyl-phenyl)-4,4,5,5-tetramethylimidazoline in 30 ml anhydrous THF was stirred on an ice bath, into which 250 mg (1.2 mmol) DCC and 135 mg (1 mmol) HOBt were added and stirred on an ice bath for 10 min. Then a solution prepared with 300 mg (1 mmol) HCl·Lys(Boc)-Ome, 122 mg (1 mmol) N-methylmorpholine and 6 mL anhydrous THF was added thereto, and the reaction mixture was reacted at RT for 24 h. TLC (ethyl acetate:petroleum ether=2:1) showed disappearance of HCl·Lys(Boc)-Ome. The reaction mixture was concentrated under reduced pressure till dry, the residue was dissolved in ethyl acetate and insoluble material was removed by filtration. The filtrate was sequentially washed with a saturated aqueous solution of sodium bicarbonate and with a saturated aqueous solution of NaCl, the separated ethyl acetate phase was dried over anhydrous sodium sulfate and filtered, and the filtrate was then concentrated under reduce pressure at 37° C. (these operations were hereinafter referred to as a generic "routine procedure"). The residue was purified by column chromatography (ethyl acetate:petroleum ether=2:1) to give 433 mg (65%) of the title compound as blue solid. ESI-MS(m/z) 550 [M+H]⁺.

Example 8. Preparation of 1,3-dioxo-2-[(4'-oxyacetyl-Lys-OMe)phenyl]-4,4,5,5-tetramethylimidazoline 625 mg (1 mmol) 1,3-dioxo-2-[(4'-oxyacetyl-NO-Boc-Lys-OMe)phenyl]-4,4,5,5-tetramethylimidazoline was dissolved in 15 mL anhydrous hydrogen chloride-ethyl acetate (4N) and stirred at RT for 3 h until the starting material spot disappeared as shown by TLC ($CHCl_3$:MeOH, 20:1). The reaction mixture was then subjected to the routine procedure. The residue was crystallized in anhydrous ethyl ether to afford the title compound.

Preparation of the Peptide Having Thrombolytic Activity: Properly Protected ARPAK (SEQ. ID NO. 4)

Example 9. Preparation of Boc-Ala-Lys(Z)-OBzl 473 mg (2.5 mmol) Boc-Ala was dissolved in 10 ml anhydrous THF. A solution prepared with 338 mg (2.5 mmol) HOBt, 619 mg (3 mmol) DCC and 10 mL anhydrous THF was added thereto on an ice bath. The reaction mixture was stirred on the ice bath for 20 min before a solution prepared with 936 mg (2.3 mmol) HCl·Lys(Z)-Obzl, 232 mg (2.3 mmol) N-methyl morpholine and 6 mL anhydrous THF was added thereto. The resultant reaction mixture reacted at RT for 24 h until HCl·Lys(Z)-Obzl disappeared as shown by TLC ($CHCl_3$:MeOH=30:1). The reaction mixture was subjected to the routine procedure to give 1.204 g (97%) of the title compound as colorless solid. Mp 88-90° C. $[\alpha]_D^{20}$=−29.2 (c=0.1, MeOH). ESI-MS(m/z) 565 [M+Na]⁺.

Example 10. Preparation of HCl·Ala-Lys(Z)-OBzl 1.354 g (2.5 mmol) Boc-Ala-Lys(Z)-Obzl was dissolved in approximately 10 ml solution of anhydrous hydrogen chloride in ethyl acetate (4N) and stirred at RT for 3 h until the starting material spot disappeared as shown by TLC ($CHCl_3$:MeOH, 30:1). The reaction mixture solution was concentrated under reduced pressure at RT, and the residue was dissolved in ethyl acetate and then concentrated at RT; the above process was repeated for several times until all free hydrogen chloride was removed (these operations are hereinafter referred to as a "routine procedure"). The residue was crystallized in anhydrous ethyl ether to afford the title compound which was directly used in the reaction of the next step.

Example 11. Preparation of Boc-Pro-Ala-Lys(Z)-OBzl 538 mg (2.5 mmol) Boc-Pro was dissolved in an appropriate amount of anhydrous THF followed by addition of 338 mg (2.5 mmol) HOBt and 619 mg (3 mmol) DCC in anhydrous THF on an ice bath, and then reacted for 20 min. To this solution, a solution prepared with 1.099 g (2.3 mmol) HCl·Ala-Lys(Z)-Obzl and 232 mg (2.3 mmol) N-methyl morpholine in 10 mL anhydrous THF was added, and the reaction was carried out at RT for 24 h. TLC ($CHCl_3$:MeOH, 20:1) showed disappearance of the starting material spot. The reaction compounds were subjected to the routine procedure to afford 2.847 g (98%) title compound, Mp 82-83° C. $[\alpha]_D^{20}$=−46.4 (c=0.11, MeOH). ESI-MS(m/z) 661 [M+Na]⁺.

Example 12. Preparation of HCl·Pro-Ala-Lys(Z)-OBzl 1.596 g (2.5 mmol) Boc-Pro-Ala-Lys(Z)-Obzl was dissolved in a 15 mL solution of anhydrous hydrogen chloride in ethyl acetate (4N) and stirred at RT for 3 h until the starting material spot disappeared as shown by TLC ($CHCl_3$:MeOH, 20:1). The reaction mixture was subjected to the routine procedure, and the residue was crystallized in anhydrous ethyl ether to give the title compound which was directly used in the reaction of the next step.

Example 13. Preparation of Boc-Arg(NO₂)-Pro-Ala-Lys(Z)-OBzl

On an ice bath, a solution of 798 mg (2.5 mmol) Boc-Arg(NO₂), 338 mg (2.5 mmol) HOBt, 619 mg (3 mmol) DCC in 10 mL anhydrous THF was stirred for 20 min, into which a solution prepared with 1.322 g (2.3 mmol) HCl·Pro-Ala-Lys(Z)-Obzl and 232 mg (2.3 mmol) N-methylmorpholine in 5 mL anhydrous THF was added and the reaction was carried out at RT for 24 hours until the starting material spot disappeared as shown by TLC ($CHCl_3$:MeOH, 20:1). The routine procedure was carried out to give 1.642 g (85%) of the title compound. Mp 84-85° C. $[\alpha]_D^{20}$=−65.0 (c=0.13, MeOH). ESI-MS (m/z) 864 [M+Na]⁺.

Example 14. Preparation of HCl·Arg(NO₂)-Pro-Ala-Lys(Z)-OBzl 2.099 g (2.5 mmol) Boc-Arg(NO₂)-Pro-Ala-Lys(Z)-OBzl was dissolved in a 20 mL solution of anhydrous hydrogen chloride in ethyl acetate (4N) and stirred at RT for 3 h until the starting material spot disappeared as shown by TLC ($CHCl_3$:MeOH, 20:1). The reaction mixture was subjected to the routine procedure, and the residue was crystallized in anhydrous ethyl ether to give the title compound which was directly used in the reaction of the next step.

Example 15. Preparation of Boc-Ala-Arg(NO$_2$)-Pro-Ala-Lys(Z)-OBzl

On an ice bath, a solution of 473 mg (2.5 mmol) Boc-Ala, 338 mg (2.5 mmol) HOBt, 619 mg (3 mmol) DCC in 10 mL anhydrous THF was stirred for 20 min, into which a solution prepared with 1.785 g (2.3 mmol) HCl·Arg(NO$_2$)-Pro-Ala-Lys(Z)-Obzl, 232 mg (2.3 mmol) N-methylmorpholine in 5 mL anhydrous THF was added and the reaction was carried out for 24 hours to give 1.802 g (86%) of the title compound. Mp 87-89° C. $[\alpha]_D^{20}$=−63.9 (c=0.12, MeOH). ESI-MS (m/e) 934 [M+Na]$^+$.

Example 16. Preparation of Boc-Ala-Arg(NO$_2$)-Pro-Ala-Lys(Z)

921 mg (1 mmol) Boc-Ala-Arg(NO$_2$)-Pro-Ala-Lys(Z)-OBzl was dissolved in 3 mL methanol, into which a NaOH aqueous solution (2N) was added on an ice bath and stirred at RT for 30 min. With pH maintained at 12, the reaction was stirred on the ice bath for 10 min until the starting material spot disappeared as shown by TLC. pH was adjusted to 7 with 2N HCl, and the reaction liquid was concentrated under reduced pressure. The residue was diluted with 2 mL saturated saline and adjusted to pH 2 with 2N HCl, and then extracted 3 times with ethyl acetate (5 mL×3). The layers of ethyl acetate phase were combined and dried over anhydrous sodium sulfate, and concentrated under reduced pressure at RT to afford 767 mg (80%) of title compound as colorless solid. EI-MS (m/z) 830 [M–H]$^-$.
Preparation of Thrombus Targeting/Anti-Thrombus Peptide: Properly Protected RGDS (SEQ. ID NO. 11), RGDV (SEQ. ID NO. 12), RGDF (SEQ. ID NO. 13)

Example 17. Preparation of Boc-Asp(OBzl)-Ser(Bzl)-OBzl

On an ice bath, a solution of 808 mg (2.5 mmol) Boc-Asp(OBzl), 338 mg (2.5 mmol) HOBt, 619 mg (3 mmol) DCC in 10 mL anhydrous THF was stirred and reacted for 20 min, and then a solution prepared with 740 mg (2.3 mmol) HCl·Ser(Bzl)-Obzl, 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction compounds were subjected to the routine procedure to afford 1.29 g (95%) of the title compound as colorless oily matter. ESI-MS(m/z) 591 [M+H]$^+$.

Example 18. Preparation of HCl·Asp(OBzl)-Ser(Bzl)-OBzl 1.477 g (2.5 mmol) Boc-Asp(OBzl)-Ser(Bzl)-Obzl was dissolved in a 15 mL solution of anhydrous hydrogen chloride in ethyl acetate (4N) and stirred at RT for 3 h until the starting material disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 19. Preparation of Boc-Gly-Asp(OBzl)-Ser(Bzl)-OBzl

On an ice bath, a solution of 438 mg (2.5 mmol) Boc-Gly, 338 mg (2.5 mmol) HOBt, 619 mg (3 mmol) DCC in 10 mL anhydrous THF was stirred for 20 min, and then a solution prepared with 1.212 g (2.3 mmol) HCl·Asp(OBzl)-Ser(Bzl)-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.461 g (98%) of the title compound as colorless solid. Mp 53-55° C. $[\alpha]_D^{20}$=−23.7 (c=0.13, MeOH). ESI-MS (m/z) 649 [M+H]$^+$.

Example 20. Preparation of HCl·Gly-Asp(OBzl)-Ser(Bzl)-OBzl 1.619 g (2.5 mmol) Boc-Gly-Asp(OBzl)-Ser(Bzl)-Obzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 21. Preparation of Boc-Arg(NO$_2$)-Gly-Asp(OBzl)-Ser(Bzl)-OBzl

On an ice bath, a solution of 798 mg (2.5 mmol) Boc-Arg(NO$_2$), 338 mg (2.5 mmol) HOBt, 619 mg (3 mmol) DCC in 10 mL anhydrous THF was stirred for 20 min, and then a solution prepared with 1.343 g (2.3 mmol) HCl·Gly-Asp(OBzl)-Ser(Bzl)-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). After the routine procedure, 1.66 g (85%) of the title compound was obtained as colorless solid. Mp 74-75° C. $[\alpha]_D^{20}$=−26.2 (c=0.12, MeOH). ESI-MS(m/z) 872 [M+Na]$^+$.

Example 22. Preparation of HCl·Arg(NO$_2$)-Gly-Asp(OBzl)-Ser(Bzl)-OBzl

A mixture of 2.122 g (2.5 mmol) Boc-Arg(NO$_2$)-Gly-Asp(OBzl)-Ser(Bzl)-Obzl and a 20 mL solution of hydrogen chloride in ethyl acetate (4N) was stirred at RT for 3 h until the starting material spot disappeared as shown by TLC (CHCl$_3$: MeOH, 20:1). The reaction mixture was subjected to the routine procedure, the residue was crystallized in anhydrous ethyl ether to afford the title compound.

Example 23. Preparation of Boc-Asp(OBzl)-Val-OBzl

On an ice bath, a solution of 808 mg (2.5 mmol) Boc-Asp(OBzl), 338 mg (2.5 mmol) HOBt, 619 mg (3 mmol) DCC in 10 ml anhydrous THF was stirred for 20 min, and then a solution prepared with 558 mg (2.3 mmol) HCl·Val-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.129 g (96%) of the title compound as colorless oily liquid. ESI-MS(m/z) 512 [M+H]$^+$.

Example 24. Preparation of HCl·Asp(OBzl)-Val-OBzl 1.278 g (2.5 mmol) Boc-Asp(OBzl)-Val-OBzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 25. Preparation of Boc-Gly-Asp(OBzl)-Val-OBzl

On an ice bath, a solution of 438 mg (2.5 mmol) Boc-Gly, 338 mg (2.5 mmol) HOBt, 619 mg (3 mmol) DCC in 10 ml anhydrous THF was stirred for 20 min, and then a solution prepared with 1.03 g (2.3 mmol) HCl·Asp(OBzl)-Val-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.242 g (95%) of the title compound as colorless solid. Mp 66-68° C. $[\alpha]_D^{20}=-43.8$ (c=0.11, MeOH). ESI-MS(m/z) 592 [M+Na]$^+$.

Example 26. Preparation of HCl·Gly-Asp(OBzl)-Val-OBzl 1.421 g (2.5 mmol) Boc-Gly-Asp(OBzl)-Val-OBzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 27. Preparation of Boc-Arg(NO$_2$)-Gly-Asp(OBzl)-Val-OBzl

On an ice bath, a solution of 798 mg (2.5 mmol) Boc-Arg(NO$_2$), 338 mg (2.5 mmol) HOBt, 619 mg (3 mmol) DCC in 10 ml anhydrous THF was stirred for 20 min, and then a solution prepared with 1.162 g (2.3 mmol) HCl·Gly-Asp(OBzl)-Val-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.523 g (86%) of the title compound as colorless solid. Mp 107-109° C. $[\alpha]_D^{20}=-38.0$ (c=0.12, MeOH). ESI-MS(m/z) 793 [M+Na]$^+$.

Example 28. Preparation of HCl·Gly-Asp(OBzl)-Val-OBzl 1.925 g (2.5 mmol) Boc-Arg(NO$_2$)-Gly-Asp(OBzl)-Val-OBzl was dissolved in a 20 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound.

Example 29. Preparation of Boc-Asp(OBzl)-Phe-OBzl

On an ice bath, a solution of 808 mg (2.5 mmol) Boc-Asp(OBzl), 338 mg (2.5 mmol) HOBt, 619 mg (3 mmol) DCC in 10 ml anhydrous THF was stirred for 20 min, and then a solution prepared with 668 mg (2.3 mmol) HCl.Phe-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). After the routine procedure, 1.222 g (95%) of the title compound was obtained as colorless solid. Mp 79-80° C. $[\alpha]_D^{20}=-24.2$ (c=0.13, MeOH), ESI-MS(m/z) 561 [M+H]$^+$.

Example 30. Preparation of HCl·Asp(OBzl)-Phe-OBzl 1.398 g (2.5 mmol) Boc-Asp(OBzl)-Phe-OBzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 31. Preparation of Boc-Gly-Asp(OBzl)-Phe-OBzl

On an ice bath, a solution of 438 mg (2.5 mmol) Boc-Gly, 338 mg (2.5 mmol) HOBt, 619 mg (3 mmol) DCC in anhydrous THF was stirred for 20 min, and then a solution prepared with 1.141 g (2.3 mmol) HCl·Asp(OBzl)-Phe-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.29 g (91%) of the title compound as colorless solid. Mp 70-71° C. $[\alpha]_D^{20}=-22.5$ (c=0.14, MeOH). ESI-MS(m/z) 640 [M+Na]$^+$.

Example 32. Preparation of HCl·Gly-Asp(OBzl)-Phe-OBzl 1.541 g (2.5 mmol) Boc-Gly-Asp(OBzl)-Phe-OBzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound which was directly used in the reaction of the next step.

Example 33. Boc-Arg(NO$_2$)-Gly-Asp(OBzl)-Phe-OBzl

On an ice bath, a solution of 798 mg (2.5 mmol) Boc-Arg(NO$_2$), 338 mg (2.5 mmol) HOBt, 619 mg (3 mmol) DCC in 10 ml anhydrous THF was stirred for 20 min, and then a solution prepared with 1.272 g (2.3 mmol) HCl·Gly-Asp(OBzl)-Phe-Obzl and 232 mg (2.3 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 1.637 g (87%) of the title compound as colorless solid. Mp 77-79° C. $[\alpha]_D^{20}=-22.6$ (c=0.09, MeOH). ESI-MS(m/z) 841 [M+Na]$^+$.

Example 34. Preparation of HCl·Arg(NO$_2$)-Gly-Asp(OBzl)-Phe-OBzl 2.045 g (2.5 mmol) Boc-Arg(NO$_2$)-Gly-Asp(OBzl)-Phe-OBzl was dissolved in a 15 mL solution of anhydrous hydrogen chloride in ethyl acetate (4N) and stirred at RT for 3 h until the starting material spot disappeared as shown by TLC (CHCl$_3$:MeOH, 20:1). The reaction mixture was subjected to the routine procedure, and the residue was crystallized in anhydrous ethyl ether to give the title compound. Preparation of Ternary Conjugates of ARPAK (SEQ. ID NO. 4)/Imidazoline/RGD (Compounds of General Formula I-1-1): Ia, Ib, Ic Example 35. Preparation of 1,3-dioxo-2-{4'-oxy-acetyl-{N$^\omega$-[Boc-Ala-Arg(NO$_2$)-Pro-Ala-Lys(Z)]-Lys-OMe}phenyl}-4,4,5,5-tetramethylimidazoline On an ice bath, a solution of 821 mg (1 mmol) Boc-Ala-Arg(NO$_2$)-Pro-Ala-Lys(Z), 135 mg (1 mmol) HOBt and 250 mg (1 mmol) DCC in 10 mL anhydrous THF was stirred for 20 min, and then a solution prepared with 480 mg (1 mmol) 1,3-dioxo-2-[(4'-oxyacetyl-Lys-OMe)phenyl]-4,4,5,5-tetramethylimidazoline and 100 mg (1 mmol) N-methylmorpholine in 5 mL anhydrous THF was added thereto and reacted at RT for 24 h until the starting material disappeared as shown by TLC (CHCl$_3$:MeOH, 40:1). The reaction mixture was subjected to the routine procedure to afford 925 mg (83%) of the title compound as blue solid. Mp 179-182° C. $[\alpha]_D^{20}$ =−34.3 (c=0.14, MeOH), ESI-MS(m/z) 1275 [M+Na]$^+$. IR (KBr) 3319, 2935, 1658, 1531, 1448, 1363, 1254, 1168, 1053, 835, 749, 540 cm$^{-1}$.

Example 36. Preparation of 1,3-dioxo-2-{4'-oxy-acetyl-{N$^\omega$-[Boc-Ala-Arg(NO$_2$)-Pro-Ala-Lys(Z)]-Lys}phenyl}-4,4,5,5-tetramethylimidazoline On an ice bath, 1260 mg (1 mmol) 1,3-dioxo-2-{4'-oxyacetyl-{N$^\omega$-[Boc-Ala-Arg(NO$_2$)-Pro-Ala-Lys(Z)]-Lys-OMe}phenyl}-4,4,5,5-tetramethylimidazoline was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate and filtered, and the filtrate was concentrated under reduced pressure at RT to afford 945 mg (82%) of the title compound as blue solid. EI-MS (m/z) 1238 [M−H]$^-$.

Example 37. Preparation of 1,3-dioxo-2-{4'-oxy-acetyl-{N$^\omega$-[Boc-Ala-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethyl-imidazoline On an ice bath, a solution of 618 mg (0.5 mmol) 1,3-dioxo-2-{4'-oxyacetyl-{N$^\omega$-[Boc-Ala-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 442 mg (0.5 mmol) HCl·Arg(NO$_2$)-Gly-Asp(OBzl)-Ser(Bzl)-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 300 mg (31%) of the title compound as blue solid. Mp 138-140° C. $[\alpha]_D^{20}$=−39.4 (c=0.13, MeOH). ESI-MS(m/z) 1991 [M+H]$^+$. IR(KBr) 3309, 2936, 1656, 1531, 1449, 1363, 1256, 836, 743, 697, 601 cm$^{-1}$.

Example 38. Preparation of 1,3-dioxo-2-{4'-oxy-acetyl-{N$^\omega$-[Boc-Ala-Arg(NO$_2$)-Pro-Ala-Lys(Z)]-Lys-Arg-(NO$_2$)-Gly-Asp(OBzl)-Val-OBzl}phenyl}-4,4,5,5-tetramethylimidazoline On an ice bath, a solution of 618 mg (0.5 mmol) 1,3-dioxo-2-{4'-oxyacetyl-{N$^\omega$-[Boc-Ala-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 421 mg (0.5 mmol) HCl·Arg(NO$_2$)-Gly-Asp(OBzl)-Val-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 389 mg (36%) of the title compound as blue solid. Mp117-120° C. $[\alpha]_D^{20}$=−14.8 (c=0.01, MeOH). ESI-MS(m/z) 1913 [M+H]$^+$. IR(KBr) 3312, 2937, 1655, 1530, 1448, 1362, 1257, 835, 744, 697, 592 cm$^{-1}$.

Example 39. Preparation of 1,3-dioxo-2-{4'-oxy-acetyl-{N$^\omega$-[Boc-Ala-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline On an ice bath, a solution of 618 mg (0.5 mmol) 1,3-dioxo-2-{4'-oxyacetyl-{N$^\omega$-[Boc-Ala-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 445 mg (0.5 mmol) HCl·Arg(NO$_2$)-Gly-Asp(OBzl)-Phe-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 320 mg (36%) of the title compound as blue solid. Mp115-118° C. $[\alpha]_D^{20}$=−21.5 (c=0.16, MeOH). ESI-MS (m/z) 1961 [M+H]$^+$. IR(KBr) 3316, 2936, 1654, 1529, 1448, 1362, 1256, 1169, 742, 698, 593 cm$^{-1}$.

Example 40. Preparation of 1,3-dioxo-2-{4'-oxy-acetyl-[N$^\omega$-(Ala-Arg-Pro-Ala-Lys)-Lys-Arg-Gly-Asp-Ser]phenyl}-4,4,5,5-tetramethylimidazoline (Ia)

On an ice bath, 199 mg (0.1 mmol) 1,3-dioxo-2-{4'-oxyacetyl-{N$^\omega$-[Boc-Ala-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethyl-imidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH=8 with 25% ammonia water, desalted with Sephadex G10, and then purified on a C18 column. The collected fractions were lyophilized to afford 109 mg (85%) of the title compound as blue solid. Mp 134-135° C. $[\alpha]_D^{20}$=−39.7 (c=0.12, MeOH). FT-MS(m/z) 1374.7290 [M+H]$^+$, 2748.4580 [2M+H]$^+$, 4122.1870 [3M+

H]⁺, 5495.9160 [4M+H]⁺. g=2.00779. IR(KBr) 3346, 3180, 2920, 1665, 1537, 1449, 1252, 1179, 1030, 837, 801, 720, 639, 518 cm$^{-1}$.

Example 41. Preparation of 1,3-dioxo-2-{4'-oxy-acetyl-[N$^ω$-(Ala-Arg-Pro-Ala-Lys)-Lys-Arg-Gly-Asp-Val]phenyl}-4,4,5,5-tetramethylimidazoline (Ib)

On an ice bath, 190 mg (0.1 mmol) 1,3-dioxo-2-{4'-oxyacetyl-{N$^ω$-[Boc-Ala-Arg(NO$_2$)-Pro-Ala-Lys(Z)]-Lys-Arg-(NO$_2$)-Gly-Asp(OBzl)-Val-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 96 mg (82%) of the title compound as blue solid. Mp 143-144° C. $[\alpha]_D^{20}$=−31.8 (c=0.01, MeOH). FT-MS(m/z) 1386.7654 [M+H]⁺, 2772.5308, [2M+H]⁺, 4158.2962 [3M+H]⁺, 5544.0616 [4M+H]⁺. g=2.00779. IR(KBr) 3349, 2942, 1659, 1539, 1394, 1250, 1030, 639 cm$^{-1}$.

Example 42. Preparation of 1,3-dioxo-2-{4'-oxy-acetyl-[N$^ω$-(Ala-Arg-Pro-Ala-Lys)-Lys-Arg-Gly-Asp-Phe]phenyl}-4,4,5,5-tetramethylimidazoline (Ic)

On an ice bath, 194 mg (0.1 mmol) 1,3-dioxo-2-{4'-oxyacetyl-{N$^ω$-[Boc-Ala-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 106 mg (81%) of the title compound as blue solid. Mp 96-97° C. $[\alpha]_D^{20}$=−44.4 (c=0.15, MeOH). FT-MS (m/z) ESI-MS (m/z) 1444.7654 [M+H]⁺, ESI-MS(m/z) 2888.5308 [2M+H]⁺, 4332.2962 [3M+H]⁺, 5776.0616 [4M+H]⁺. g=2.00789. IR(KBr) 3363, 1665, 1538, 1448, 1256, 1173, 1031, 640, 577, 518 cm$^{-1}$.

Preparation of the Peptide Having Thrombolytic Activity: Properly Protected GRPAK (SEQ. ID NO. 5)

Example 43. Preparation of Boc-Gly-Arg(NO$_2$)-Pro-Ala-Lys(Z)-OBzl

On an ice bath, a solution of 438 mg (2.5 mmol) Boc-Gly, 338 mg (2.5 mmol) HOBt, 619 mg (3 mmol) DCC in 10 ml anhydrous THF was stirred for 20 min, and then a solution prepared with 1.785 g (2.3 mmol) HCl·Arg(NO$_2$)-Pro-Lys(Z)-Obzl and 232 mg (2.3 mmol) N-methylmorpholine in 5 mL anhydrous THF was added thereto and reacted at RT for 24 h to give 1.857 g (90%) of the title compound. Mp 85-87° C. $[\alpha]_D^{20}$=−38.5 (c=0.11, MeOH). ESI-MS (m/e) 920 [M+Na]⁺.

Example 44. Preparation of Boc-Gly-Arg(NO$_2$)-Pro-Ala-Lys(Z)

907 mg (1 mmol) Boc-Gly-Arg(NO$_2$)-Pro-Ala-Lys(Z)-OBzl was dissolved in 3 ml methanol followed by addition of a NaOH aqueous solution (2N) on an ice bath, and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate, and then concentrated under reduced pressure at RT to afford 785 mg (82%) of the title compound as colorless solid. EI-MS (m/z) 816 [M−H]⁻.

Preparation of Ternary Conjugates of GRPAK (SEQ. ID NO. 5)/Imidazoline/RGD (Compounds of General Formula I-1-2): Id, Ie, If Example 45. Preparation of 1,3-dioxo-2-{4'-oxy-acetyl-{N$^ω$-[Boc-Gly-Arg(NO$_2$)-Pro-Ala-Lys(Z)]-Lys-OMe}phenyl}-4,4,5,5-tetramethylimidazoline On an ice bath, a solution of 817 mg (1 mmol) Boc-Gly-Arg(NO$_2$)-Pro-Ala-Lys(Z), 135 mg (1 mmol) HOBt and 250 mg (1 mmol) DCC in 10 mL anhydrous THF was stirred for 20 min, and then a solution prepared with 480 mg (1 mmol) 1,3-dioxo-2-[(4'-oxyacetyl-Lys-OMe)phenyl]-4,4,5,5-tetramethylimidazoline and 100 mg (1 mmol) N-methylmorpholine in 5 mL anhydrous THF was added thereto and reacted at RT for 24 h until the starting material disappeared as shown by TLC (CHCl$_3$:MeOH, 40:1). The reaction mixture was subjected to the routine procedure to afford 680 mg (52%) of the title compound as blue solid. Mp 79-82° C. $[\alpha]_D^{20}$=−12.3 (c=0.14, MeOH), ESI-MS(m/z) 1261 [M+Na]⁺. IR (KBr) 3319, 2935, 1658, 1531, 1448, 1363, 1254, 1168, 1053, 835, 749, 540 cm$^{-1}$.

Example 46. Preparation of 1,3-dioxo-2-{4'-oxy-acetyl-{N$^ω$-[Boc-Gly-Arg(NO$_2$)-Pro-Ala-Lys(Z)]-Lys}phenyl}-4,4,5,5-tetramethylimidazoline On an ice bath, 1260 mg (1 mmol) 1,3-dioxo-2-{4'-oxyacetyl-{N$^ω$-[Boc-Gly-Arg(NO$_2$)-Pro-Ala-Lys(Z)]-Lys-OMe}phenyl}-4,4,5,5-tetramethylimidazoline was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate and filtered, and the filtrate was concentrated under reduced pressure at RT to afford 945 mg (82%) of the title compound as colorless solid. EI-MS (m/z) 1223 [M−H]⁻.

Example 47. Preparation of 1,3-dioxo-2-{4'-oxy-acetyl-{N$^ω$-[Boc-Gly-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethyl-imidazoline On an ice bath, a solution of 611 mg (0.5 mmol) 1,3-dioxo-2-{4'-oxyacetyl-{N$^ω$-[Boc-Gly-Arg(NO$_2$)-Pro-Ala- Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 442 mg (0.5 mmol) HCl·Arg(NO$_2$)-Gly-Asp(OBzl)-Ser(Bzl)-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 500 mg (48%) of the title compound as blue solid. Mp 127-129° C. $[\alpha]_D^{20}$=−49.4 (c=0.13, MeOH). ESI-MS(m/z) 1956 [M+H]$^+$. IR(KBr) 3306, 2936, 1652, 1531, 1449, 1362, 1255, 1166, 742, 697, 592 cm$^{-1}$.

Example 48. Preparation of 1,3-dioxo-2-{4'-oxyacetyl-{N$^\omega$-[Boc-Gly-Arg(NO$_2$)-Pro-Ala-Lys(Z)]-Lys-Arg-(NO$_2$)-Gly-Asp(OBzl)-Val-OBzl}phenyl}-4,4,5,5-tetramethylimidazoline On an ice bath, a solution of 611 mg (0.5 mmol) 1,3-dioxo-2-{4'-oxyacetyl-{N$^\omega$-[Boc-Gly-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 421 mg (0.5 mmol) HCl·Arg(NO$_2$)-Gly-Asp(OBzl)-Val-Obzl, 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 392 mg (35%) of the title compound as blue solid. Mp 147-150° C. $[\alpha]_D^{20}$=−34.6 (c=0.16, MeOH). ESI-MS(m/z) 1899 [M+Na]$^+$. IR(KBr) 3311, 3068, 2937, 1661, 1531, 1451, 1395, 1254, 1163, 839, 743, 697, 596 cm$^{-1}$.

Example 49. Preparation of 1,3-dioxo-2-{4'-oxyacetyl-{N-[Boc-Gly-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline On an ice bath, a solution of 611 mg (0.5 mmol) 1,3-dioxo-2-{4'-oxyacetyl-{N$^\omega$-[Boc-Gly-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 445 mg (0.5 mmol) HCl·Arg(NO$_2$)-Gly-Asp(OBzl)-Phe-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 336 mg (31%) of the title compound as blue solid. Mp 125-128° C. $[\alpha]_D^{20}$=−31.3 (c=0.18, MeOH). ESI-MS (m/z) 1925 [M+H]$^+$. IR(KBr) 3315, 2935, 1657, 1529, 1448, 1361, 1257, 1173, 834, 742, 698, 541 cm$^{-1}$.

Example 50. Preparation of 1,3-dioxo-2-{4'-oxyacetyl-[N$^\omega$-(Gly-Arg-Pro-Ala-Lys)-Lys-Arg-Gly-Asp-Ser]phenyl}-4,4,5,5-tetramethylimidazoline (Id)

On an ice bath, 195 mg (0.1 mmol) 1,3-dioxo-2-{4'-oxyacetyl-{N$^\omega$-[Boc-Gly-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 102 mg (82%) of the title compound as blue solid. Mp 142-145° C. $[\alpha]_D^{20}$=−29.7 (c=0.14, MeOH). FT-MS(m/z) 1360.7133 [M+H]$^+$, 2720.4266 [2M+H]$^+$, 4080.1399 [3M+H]$^+$, 5439.8532 [4M+H]$^+$. g=2.00779. IR(KBr) 3348, 3180, 2940, 1670, 1539, 1447, 1199, 1134, 1034, 836, 801, 721, 638 cm$^{-1}$.

Example 51. Preparation of 1,3-dioxo-2-{4'-oxyacetyl-[N$^\omega$-(Gly-Arg-Pro-Ala-Lys)-Lys-Arg-Gly-Asp-Val]phenyl}-4,4,5,5-tetramethylimidazoline (Ie)

On an ice bath, 190 mg (0.1 mmol) 1,3-dioxo-2-{4'-oxyacetyl-{N$^\omega$-[Boc-Gly-Arg(NO$_2$)-Pro-Ala-Lys(Z)]-Lys-Arg-(NO$_2$)-Gly-Asp(OBzl)-Val-OBzl}phenyl}-4,4,5,5-tetramethyl-imidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 99 mg (84%) of the title compound as blue solid. Mp 147-149° C. $[\alpha]_D^{20}$=−31.1 (c=0.17, MeOH). FT-MS(m/z) 1372.7497 [M+H]$^+$, 2744.4994 [2M+H]$^+$, 4116.2491 [3M+H]$^+$, 5487.9988 [4M+H]$^+$. g=2.00779. IR(KBr) 3338, 2960, 1662, 1539, 1451, 1392, 1251, 1170, 1030, 639, 519 cm$^{-1}$.

Example 52. Preparation of 1,3-dioxo-2-{4'-oxyacetyl-[N$^\omega$-(Gly-Arg-Pro-Ala-Lys)-Lys-Arg-Gly-Asp-Phe]phenyl}-4,4,5,5-tetramethylimidazoline (If)

On an ice bath, 192 mg (0.1 mmol) 1,3-dioxo-2-{4'-oxyacetyl-{N$^\omega$-[Boc-Gly-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 106 mg (81%) of the title compound as blue solid. Mp 84-85° C. $[\alpha]_D^{20}$=−54.1 (c=0.15, MeOH). FT-MS (m/z) 1420.7497 [M+H]$^+$, 2840.4994 [2M+H]$^+$, ESI-MS FT-MS(m/z) 1420.7497 [M+H]$^+$, 2840.4994 [2M+H]$^+$, 4260.2491 [3M+H]$^+$, 5679.9976 [4M+H]$^+$. g=2.00789. IR(KBr) 3344, 3080, 2930, 1666, 1535, 1392, 1250, 1181, 1030, 835, 800, 719, 638 cm$^{-1}$.

Preparation of the Peptide Having Thrombolytic Activity: Properly Protected RPAK (SEQ. ID NO. 3)

Example 53. Preparation of Boc-Arg(NO$_2$)-Pro-Ala-Lys(Z)

On an ice bath, 850 mg (1 mmol) Boc-Arg(NO$_2$)-Pro-Ala-Lys(Z)-OBzl was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate, and filtered, then the filtrate is concentrated under reduced pressure at RT to afford 742 mg (92%) of the title compound as colorless solid. EI-MS (m/z) 849 [M−H]⁻. Preparation of Ternary Conjugates of RPAK (SEQ. ID NO. 3)/Imidazoline/RGD (Compounds of General Formula I-1-3): Ig, Ih, Ii Example 54. Preparation of 1,3-dioxo-2-{4'-oxyacetyl-{N$^\omega$-[Boc-Arg(NO$_2$)-Pro-Ala-Lys(Z)]-Lys-OMe}phenyl}-4,4,5,5-tetramethylimidazoline On an ice bath, a solution of 760 mg (1 mmol) Boc-Arg(NO$_2$)-Pro-Ala-Lys(Z), 135 mg (1 mmol) HOBt and 250 mg (1 mmol) DCC in 10 mL anhydrous THF was stirred for 20 min, and then a solution prepared with 480 mg (1 mmol) 1,3-dioxo-2-[(4'-oxyacetyl-Lys-OMe)phenyl]-4,4,5,5-tetramethylimidazoline and 100 mg (1 mmol) N-methylmorpholine in 5 mL anhydrous THF was added thereto and reacted at RT for 24 h until the starting material disappeared as shown by TLC (CHCl$_3$:MeOH, 40:1). The reaction mixture was subjected to the routine procedure to afford 920 mg (83%) of the title compound as blue solid. Mp 72-76° C. $[\alpha]_D^{20}$=−32.7 (c=0.13, MeOH), ESI-MS(m/z) 1204 [M+Na]⁺. IR (KBr) 3317, 2937, 1658, 1531, 1447, 1362, 1254, 1168, 1055, 835, 746, 697, 541, 460 cm⁻¹.

Example 55. Preparation of 1,3-dioxo-2-{4'-oxyacetyl-{N$^\omega$-[Boc-Arg(NO$_2$)-Pro-Ala-Lys(Z)]-Lys}phenyl}-4,4,5,5-tetramethylimidazoline On an ice bath, 1200 mg (1 mmol) 1,3-dioxo-2-{4'-oxyacetyl-{N$^\omega$-[Boc-Arg(NO$_2$)-Pro-Ala-Lys(Z)]-Lys-OMe}phenyl}-4,4,5,5-tetramethylimidazoline was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate and filtered, and the filtrate was concentrated under reduced pressure at RT to afford 899 mg (80%) of the title compound as blue solid. EI-MS (m/z) 1116 [M−H]⁻.

Example 56. Preparation of 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethyl-imidazoline On an ice bath, a solution of 583 mg (0.5 mmol) 1,3-dioxo-2-{4'-oxyacetyl-{N$^\omega$-[Boc-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 442 mg (0.5 mmol) HCl·Arg(NO$_2$)-Gly-Asp(OBzl)-Ser(Bzl)-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 421 mg (40%) of the title compound as blue solid. Mp 77-79° C. $[\alpha]_D^{20}$=−45.4 (c=0.15, MeOH). ESI-MS(m/z) 1897 [M+H]⁺. IR(KBr) 3319, 2934, 1658, 1530, 1449, 1361, 1256, 834, 741, 698, 542 cm⁻¹.

Example 57. Preparation of 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Val-OBzl}phenyl}-4,4,5,5-tetramethylimidazoline On an ice bath, a solution of 583 mg (0.5 mmol) 1,3-dioxo-2-{4'-oxyacetyl-{N$^\omega$-[Boc-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 421 mg (0.5 mmol) HCl·Arg(NO$_2$)-Gly-Asp(OBzl)-Val-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 472 mg (42%) of the title compound as blue solid. Mp 107-109° C. $[\alpha]_D^{20}$=−28.8 (c=0.11, MeOH). ESI-MS(m/z) 1820 [M+H]⁺. IR(KBr) 3314, 2938, 1658, 1531, 1448, 1362, 1258, 742, 698, 594 cm⁻¹.

Example 58. Preparation of 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline On an ice bath, a solution of 583 mg (0.5 mmol) 1,3-dioxo-2-{4'-oxyacetyl-{N$^\omega$-[Boc-Arg(NO$_2$)-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 445 mg (0.5 mmol) HCl·Arg(NO$_2$)-Gly-Asp(OBzl)-Phe-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 420 mg (47%) of the title compound as blue solid. Mp 141-144° C. $[\alpha]_D^{20}$=−35.7 (c=0.12, MeOH). ESI-MS(m/z) 1867 [M+H]⁺. IR(KBr) 3319, 2936, 1656, 1529, 1448, 1362, 1257, 1169, 834, 743, 698, 541 cm⁻¹.

Example 59. Preparation of 1,3-dioxo-2-{4'-oxyacetyl-[N$^\omega$-(Arg-Pro-Ala-Lys)-Lys-Arg-Gly-Asp-Ser]phenyl}-4,4,5,5-tetramethylimidazoline (Ig)

On an ice bath, 170 mg (0.1 mmol) 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Ser(Bzl)-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 102 mg (82%) of the title compound as blue solid. Mp 148-150° C. $[\alpha]_D^{20}$=−22.4 (c=0.14, MeOH). FT-MS(m/z) 1303.6919 $[M+H]^+$, 2606.3838, $[2M+H]^+$, 3909.0757 $[3M+H]^+$, 5211.7676 $[4M+H]^+$. g=2.00779. IR(KBr) 3344, 3080, 2930, 1666, 1535, 1392, 1250, 1181, 1030, 835, 800, 719, 638.

Example 60. Preparation of 1,3-dioxo-2-{4'-oxyacetyl-[N$^\omega$-(Arg-Pro-Ala-Lys)-Lys-Arg-Gly-Asp-Val]phenyl}-4,4,5,5-tetramethylimidazoline (Ih)

On an ice bath, 182 mg (0.1 mmol) 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Val-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 99 mg (84%) of the title compound as blue solid. Mp 137-139° C. $[\alpha]_D^{20}$=−34.3 (c=0.18, MeOH). FT-MS(m/z) ESI-MS(m/z) 1315.7282 $[M+H]^+$, 2630.4564 $[2M+H]^+$, 3945.1846 $[3M+H]^+$, 5259.9128 $[4M+H]^+$. g=2.00779. IR(KBr) 3329, 2953, 1665, 1533, 1391, 1198, 1134, 834, 801, 720, 599 cm$^{-1}$.

Example 61. Preparation of 1,3-dioxo-2-{4'-oxyacetyl-[N$^\omega$-(Arg-Pro-Ala-Lys)-Lys-Arg-Gly-Asp-Phe]phenyl}-4,4,5,5-tetramethylimidazoline (Ii)

On an ice bath, 187 mg (0.1 mmol) 1,3-dioxo-2-{4'-oxyacetyl-{N$^\omega$-[Boc-Arg(NO$_2$)-Pro-Ala-Lys(Z)]-Lys-Arg-(NO$_2$)-Gly-Asp(OBzl)-Phe-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 96 mg (81%) of the title compound as blue solid. Mp 99-100° C. $[\alpha]_D^{20}$=−24.7 (c=0.14, MeOH). FT-MS (m/z) 1363.7282 $[M+H]^+$, 2726.4564 $[2M+H]^+$, 4089.1846 $[3M+H]^+$, 5451.9128 $[4M+H]^+$. g=2.00789. IR(KBr) 3322, 3060, 2928, 1661, 1530, 1391, 1303, 1247, 641 cm$^{-1}$.

Preparation of the Peptide Having Thrombolytic Activity: Properly Protected PAK

Example 62. Preparation of Boc-Pro-Ala-Lys(Z)

On an ice bath, 638 mg (1 mmol) Boc-Pro-Ala-Lys(Z)-OBzl was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate and filtered, and the filtrate was then concentrated under reduced pressure at RT to afford 509 mg (91.6%) of the title compound as colorless solid. EI-MS (m/z) 547 $[M-H]^-$.

Preparation of Ternary Conjugates of PAK/Imidazoline/RGD (Compounds of General Formula I-1-4): Ij, Ik, Il Example 63. Preparation of 1,3-dioxo-2-{4'-oxyacetyl-{N$^\omega$-[Boc-Pro-Ala-Lys(Z)]-Lys-OMe}phenyl}-4,4,5,5-tetramethylimidazoline On an ice bath, a solution of 548 mg (1 mmol) Boc-Pro-Ala-Lys(Z), 135 mg (1 mmol) HOBt and 250 mg (1 mmol) DCC in 10 mL anhydrous THF was stirred for 20 min, and then a solution prepared with 480 mg (1 mmol) 1,3-dioxo-2-[(4'-oxyacetyl-Lys-OMe)phenyl]-4,4,5,5-tetramethylimidazoline and 100 mg (1 mmol) N-methylmorpholine in 5 mL anhydrous THF was added thereto and reacted at RT for 24 h until the starting material disappeared as shown by TLC (CHCl$_3$:MeOH, 40:1). The reaction mixture was subjected to the routine procedure to afford 876 mg (87%) of the title compound as blue solid. Mp 77-80° C. $[\alpha]_D^{20}$=−12.6 (c=0.16, MeOH). ESI-MS(m/z) 1003 $[M+Na]^+$. IR (KBr): 3315, 3069, 2937, 1671, 1531, 1449, 1394, 1364, 1302, 1167, 1132, 1054, 836, 743, 698, 596, 541, 458 cm$^{-1}$.

Example 64. Preparation of 1,3-dioxo-2-{4'-oxyacetyl-{N$^\omega$-[Boc-Pro-Ala-Lys(Z)]-Lys}phenyl}-4,4,5,5-tetramethylimidazoline On an ice bath, 980 mg (1 mmol) 1,3-dioxo-2-{4'-oxyacetyl-{N$^\omega$-[Boc-Pro-Ala-Lys(Z)]-Lys-OMe}phenyl}-4,4,5,5-tetramethylimidazoline was dissolved in 3 ml methanol followed by addition of a NaOH aqueous solution (2N), and then stirred at RT for 30 min. With pH maintained at 12, the reaction was stirred on the ice bath for 10 min until the starting material disappeared as shown by TLC. With pH adjusted to 7 with 2N HCl, the reaction liquid was concentrated under reduced pressure, and the residue was diluted in 2 mL saturated saline, adjusted to pH 2 with 2N HCl, and then extracted 3 times with ethyl acetate (5 mL×3). The combined ethyl acetate phase was dried over anhydrous sodium sulfate and filtered, and the filtrate was concentrated under reduced pressure at RT to afford 867 mg (80%) of the title compound as blue solid. EI-MS (m/z) 965 $[M-H]^-$.

Example 65. Preparation of 1,3-dioxo-2-{4'-oxyacetyl-{N$^\omega$-[Boc-Pro-Ala-Lys(Z)]-Lys-Arg-(NO$_2$)-Gly-Asp(OBzl)-Ser(Bzl)-OBzl}phenyl}-4,4,5,5-tetramethylimidazoline On an ice bath, a solution of 483 mg (0.5 mmol) 1,3-dioxo-2-{4'-oxyacetyl-{N$^\omega$-[Boc-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 442 mg (0.5 mmol) HCl·Arg(NO$_2$)-Gly-Asp(OBzl)-Ser(Bzl)-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 421 mg (42%) of the title compound as blue solid. Mp 97-100° C. $[\alpha]_D^{20}$=−42.5 (c=0.14, MeOH). ESI-MS(m/z) 1697

[M+H]$^+$. IR(KBr) 3298, 3070, 2935, 2869, 1642, 1534, 1450, 1369, 1253, 741, 697, 596 cm$^{-1}$.

Example 66. Preparation of 1,3-dioxo-2-{4'-oxy-acetyl-{N$^\omega$-[Boc-Pro-Ala-Lys(Z)]-Lys-Arg-(NO$_2$)-Gly-Asp(OBzl)-Val-OBzl}phenyl}-4,4,5,5-tetramethylimidazoline On an ice bath, a solution of 483 mg (0.5 mmol) 1,3-dioxo-2-{4'-oxyacetyl-{N$^\omega$-[Boc-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 432 mg (0.5 mmol) HCl·Arg(NO$_2$)-Gly-Asp(OBzl)-Val-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 357 mg (37%) of the title compound as blue solid. Mp 117-120° C. [α]$_D^{20}$=−22.3 (c=0.17, MeOH). ESI-MS(m/z) 1620 [M+H]$^+$. IR(KBr) 3303, 3072, 2935, 1644, 1533, 1451, 1394, 1364, 1255, 1167, 745, 697, 597 cm$^{-1}$.

Example 67. Preparation of 1,3-dioxo-2-{4'-oxy-acetyl-{N$^\omega$-[Boc-Pro-Ala-Lys(Z)]-Lys-Arg-(NO$_2$)-Gly-Asp(OBzl)-Phe-OBzl}phenyl}-4,4,5,5-tetramethylimidazoline On an ice bath, a solution of 483 mg (0.5 mmol) 1,3-dioxo-2-{4'-oxyacetyl-{N$^\omega$-[Boc-Pro-Ala-Lys(Z)]-Lys}phenyl}-4,4,5,5-tetramethylimidazoline, 69 mg (0.5 mmol) HOBt and 126 mg (0.6 mmol) DCC in 20 mL anhydrous THF was stirred for 20 min, and then a solution prepared with 439 mg (0.5 mmol) HCl·Arg(NO$_2$)-Gly-Asp(OBzl)-Phe-Obzl and 50 mg (0.5 mmol) N-methylmorpholine in 5 mL anhydrous THF was added thereto and reacted at RT for 24 h until the starting material disappeared as shown by TLC (CHCl$_3$:MeOH, 20:1). The reaction mixture was subjected to the routine procedure to afford 472 mg (48%) of the title compound as blue solid. Mp 111-114° C. [α]$_D^{20}$=−15.3 (c=0.13, MeOH). ESI-MS(m/z) 1667 [M+H]$^+$. IR(KBr) 3296, 3071, 2935, 1641, 1534, 1394, 1253, 1170, 834, 745, 697, 594 cm$^1$.

Example 68. Preparation of 1,3-dioxo-2-{4'-oxy-acetyl-[N$^\omega$-(Pro-Ala-Lys)-Lys-Arg-Gly-Asp-Ser]phenyl}-4,4,5,5-tetramethylimidazoline (Ij)

On an ice bath, 169 mg (0.1 mmol) 1,3-dioxo-2-{4'-oxyacetyl-{N$^\omega$-[Boc-Pro-Ala-Lys(Z)]-Lys-Arg-(NO$_2$)-Gly-Asp(OBzl)-Ser(Bzl)-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 98 mg (80%) of the title compound as blue solid. Mp 127-128° C. [α]$_D^{20}$=−22.4 (c=0.13, MeOH). FT-MS(m/z) 1147.5907 [M+H]$^+$, 2294.1814 [2M+H]$^+$, 3440.7721 [3M+H]$^+$, 4587.3628 [4M+H]$^+$. g=2.00779. IR(KBr) 3204, 1672, 1543, 1436, 1199, 1133, 837, 801, 722, 598 cm$^{-1}$.

Example 69. Preparation of 1,3-dioxo-2-{4'-oxy-acetyl-[N$^\omega$-(Pro-Ala-Lys)-Lys-Arg-Gly-Asp-Val]phenyl}-4,4,5,5-tetramethylimidazoline (Ik)

On an ice bath, 162 mg (0.1 mmol) 1,3-dioxo-2-{4'-oxyacetyl-{N$^\omega$-[Boc-Pro-Ala-Lys(Z)]-Lys-Arg-(NO$_2$)-Gly-Asp(OBzl)-Val-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 96 mg (81%) of the title compound as blue solid. Mp 123-124° C. [α]$_D^{20}$=−24.6 (c=0.13, MeOH). FT-MS(m/z) 1159.6271 [M+H]$^+$, 2318.2542 [2M+H]$^+$, 3476.8813 [3M+H]$^+$, 4635.5084 [4M+H]$^+$. g=2.00779. IR(KBr) 3388, 2959, 1666, 1540, 1494, 1198, 1134, 835, 801, 720, 598 cm$^{-1}$.

Example 70. Preparation of 1,3-dioxo-2-{4'-oxy-acetyl-[N$^\omega$-(Pro-Ala-Lys)-Lys-Arg-Gly-Asp-Phe]phenyl}-4,4,5,5-tetramethylimidazoline (Il)

On an ice bath, 169 mg (0.1 mmol) 1,3-dioxo-2-{4'-oxyacetyl-{N$^\omega$-[Boc-Pro-Ala-Lys(Z)]-Lys-Arg-(NO$_2$)-Gly-Asp(OBzl)-Phe-OBzl}phenyl}-4,4,5,5-tetramethylimidazoline was mixed with 6 mL trifluoroacetic acid and 1.5 mL trifluoromethanesulfonic acid, and stirred for 1 h until the starting material disappeared as shown by TLC (CHCl$_3$:MeOH, 1:1). The reaction mixture was concentrated under reduced pressure, and the residue was repeatedly washed with anhydrous ethyl ether and concentrated under reduced pressure. The residue was dissolved in water, adjusted to pH 8 with 25% ammonia water, desalted with Sephadex G10, and then purified on a C18 column. The collected fractions were lyophilized to afford 96 mg (81%) of the title compound as blue solid. Mp 153-154° C. [α]$_D^{20}$=−12.6 (c=0.16, MeOH). FT-MS (m/z) 1207.6271 [M+H]$^+$, 2414.2542 [2M+H]$^+$, 3620.8813 [3M+H]$^+$, 4827.5084 [4M+H]$^+$. g=2.00789. IR(KBr) 3385, 2938, 1659, 1541, 1450, 1391, 1251, 1126, 963, 841, 599, 456 cm$^{-1}$.

Experimental Example 1. Experiments on NO Radical Scavenging by Compounds Ia to Il of the Present Invention Male Wistar rats weighing 250 to 300 g were starved for 12 h before operation with free access to drinking water, and sacrificed by cervical dislocation. Thoracotomy was immediately carried out and thoracic aorta was taken out, connective tissues attached thereto were dissected, and vessels were cut into aorta rings with a length of 3 to 5 mm and placed into a perfusion bath. The bath contained 15 ml Krebs-Henseleit solution and was kept at a constant temperature of 37° C., into which 95% O$_2$-5% CO$_2$ gas was charged. The anchor to which the aorta rings were immobilized was connected to a tension transducer, and vasomotion curves were recorded on a dual-trace recorder at a paper speed of 1 mm/min. With the static tension adjusted to 1.0 g and 30 min of equilibration, norepinephrine at a final concentration of 10$^{-8}$ M was dosed to allow the aorta to contract for preexcitation. Norepinephrine was washed off, followed by 30 min of equilibration, and norepinephrine was added into the bath to a final concentration of $10^{-8}$ M. When the contraction tension was steady at a plateau level, 20 μl normal saline (blank), a 20 μl solution of any one of compounds Ia to Il in normal saline (at a final concentration of $5\times10^{-6}$ M), or a 20 μl solution of NO free radical scavenger (1,3-dioxo-2-(4'-oxyacetoxyl-phenyl)-4,4,5,5-tetramethylimidazoline, TMMZ) in normal saline (at a final concentration of $5\times10^{-6}$ M) was added into the bath. When stabilized, a 20 μl acetylcholine in normal saline was added (at a final concentration of $10^{-6}$ M). The NO scavenging ability of the drugs was expressed as a percentage of inhibition of acetylcholine induced vasodilation. The experimental results are shown in Table 1.

As shown in the experimental results, Ia to Il were able to inhibit acetylcholine's vasodilating effect on the vessel pieces by scavenging NO. As such, by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger (1,3-dioxo-2-(4'-oxyacetoxyl-phenyl)-4,4,5,5-tetramethylimidazoline, TMMZ) via Lys, 9 compounds had substantially higher activity in inhibition of acetylcholine-induced vasodilatation than TMMZ, 2 compounds had the same activity in inhibition of acetylcholine-induced vasodilatation as TMMZ, and one compound was less active in inhibition of acetylcholine-induced vasodilatation than TMMZ. Among the 12 compounds under assessment, 4 compounds had a percentage of inhibition higher than 30%, and these 4 compounds were ranked by activity in inhibition of acetylcholine-induced vasodilatation as Ie>Ih>Ib>If. This demonstrated that the activity of the TMMZ moiety in scavenging NO free radicals was generally improved by linking the thrombolytic peptide ARPAK (SEQ. ID NO. 4), GRPAK (SEQ. ID NO. 5), RPAK (SEQ. ID NO. 3) or PAK and the targeting peptide RGDS (SEQ. ID NO. 11), RGDV (SEQ. ID NO. 12) or RGDF (SEQ. ID NO. 13) to the free radical scavenger TMMZ via Lys.

TABLE 1

Percentage of Ia to Il's inhibition of vasodilatation induced by acetylcholine

| Compounds | Percentage of inhibition (Mean ± SD %) |
|---|---|
| TMMZ | 15.47 ± 2.20 |
| Ia | 22.82 ± 3.27 [a] |
| Ib | 35.32 ± 4.74 [a] |
| Ic | 21.78 ± 3.11 [a] |
| Id | 17.60 ± 2.75 [b] |
| Ie | 41.28 ± 3.27 [a] |
| If | 32.55 ± 2.55 [a] |
| Ig | 24.40 ± 3.60 [a] |
| Ih | 37.54 ± 1.84 [a] |
| Ii | 13.75 ± 2.07 [b] |
| Ij | 27.22 ± 2.68 [a] |
| Ik | 11.13 ± 2.92 [c] |
| Il | 22.62 ± 3.60 [a] | n = 6;
[a] $p < 0.01$ vs. TMMZ;
[b] $p > 0.05$ vs. TMMZ;
[c] $p < 0.05$ vs. TMMZ

Experimental Example 2. Experiments on Euglobulin Clot Lysis by Compounds Ia to Il of the Present Invention Pig blood was taken and mixed with 3.8% sodium citrate in a volume ratio of 9:1, immediately centrifuged at 3000 r/min for 10 min, and platelet-poor plasma was separated. 2 mL platelet-poor pig plasma and 36 mL ultrapure water were added into a 50 mL centrifuge tube. In each tube, 0.4 mL acetic acid (1%) was added and thoroughly mixed, and the tube was placed in a 4° C. refrigerator for 10 min and then centrifuged at 3000 r/min for 10 min. The centrifuge tubes were inverted, and then the inner wall of the tubes was dried using a filter paper after the liquid was drained. The euglobuin pellets resulting from centrifugation was freeze-dried for about 40 min and scratched out. About 35 mg euglobuin was taken and dissolved in 7 ml borax buffer (pH 9.28). The euglobuin were mostly dissolved after 1 h, into which 0.7 mL $CaCl_2$ solution (25 mM) was added, and immediately plated on a 10×10 cm glass plate with a thickness of about 1 mm. After clot formation, 10 μL normal saline, or 10 μL of a solution of one of compounds Ia to Il in normal saline (1 mM) or 10 μL of a urokinase solution in normal saline (0.8 mg/mL) was pipetted and spotted onto the clot plate, with an interval between every two drops more than 1.5 cm, and each sample was spotted 3 times. The diameter of the clot lysis circle was measured after 4 h, and the readings are listed in Table 2.

As shown in the experimental results, by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, all compounds exhibited substantial euglobulin clot lysis activity.

TABLE 2

The diameter of euglobulin clot lysis after 4 h of Ia-Il treatment

| Compounds | Diameter (Mean ± SD mm) |
|---|---|
| Normal saline | 2.9 ± 0.6 [a] |
| urokinase | 10.7 ± 0.4 [a] |
| Ia | 4.0 ± 0.0 |
| Ib | 5.2 ± 0.3 |
| Ic | 3.8 ± 0.3 |
| Id | 5.2 ± 0.3 |
| Ie | 5.5 ± 0.3 |
| If | 4.5 ± 0.5 |
| Ig | 5.2 ± 0.3 |
| Ih | 4.2 ± 0.3 |
| Ii | 4.0 ± 0.0 |
| Ij | 4.0 ± 0.0 |
| Ik | 4.5 ± 0.5 |
| Il | 4.2 ± 0.3 | n = 3;
[a] $p < 0.01$, vs. Ia-l

Experimental Example 3. In Vitro Thrombolysis Experiments for Compounds Ia to Il of the Present Invention SD rats (male, 350 to 400 g) were anaesthetized by intraperitoneal injection of a urethane solution at a dosage of 1200 mg/kg. The anaesthetized rats were fixed in a supine position, and the right common carotid artery was dissected, clamped at the proximal end with an arterial clip, and penetrated with a suture at the proximal and distal ends, respectively. The suture at the distal end is clipped tightly by a hemostatic clamp at the fur. Cannulation was performed at the distal end, the artery clamp was removed, and the total arterial blood was discharged into a 50 ml container previously treated with silicone oil. 0.8 ml rat arterial blood was injected into a vertically fixed glass tube (20 mm in length, with an inner diameter of 4 mm and an outer diameter of 5 mm, sealed with a rubber stopper at the bottom), into which was immediately inserted a thrombus immobilization screw made of stainless steel. The thrombus immobilization screw, formed by coiling of a stainless steel wire having a diameter of 0.2 mm, had a spiral part of 18 mm in length, 15 coils each having a diameter of 1.8 mm, and a stem of 7.0 mm in length which was connected to the spiral part and had a question-mark-like shape. 40 min after the blood was coagulated, the rubber stopper at the bottom of the glass tube was removed, the stem of the thrombus immobilization screw was nipped by forceps, and the thrombus-wrapped thrombus immobilization screw was carefully taken out from the glass tube. The screw was then suspended and dipped in triple-distilled water to remove excessive blood, and accurately weighed after 1 h. The thrombus was suspended in 8 mL of normal saline, or a solution of compounds Ia-Il in normal saline (at a concentration of 100 nM), or a solution of ARPAK (SEQ. ID NO. 4), GRPAK (SEQ. ID NO. 5), RPAK (SEQ. ID NO. 3) or PAK in normal saline (at a concentration of 100 nM), or a solution of urokinase in normal saline (100 IU/mL), then shaken at 37° C. in a thermostatic shaker (63 r/min), and removed after 2 h and accurately weighed to determine the weight of the thrombus. The difference in thrombus mass before and after the administration was calculated, and the results are listed in Table 3.

As shown in the experimental results, by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, all compounds exhibited substantial in vitro thrombolytic activity. Since the activity of Ia to Ic was comparable to that of ARPAK (SEQ. ID NO. 4), the activity of Id to If was comparable to that of GRPAK (SEQ. ID NO. 5), the activity of Ig to Ii was comparable to that of RPAK (SEQ. ID NO. 3), and the activity of Ij to Ii was comparable to that of PAK, on one hand the in vitro thrombolytic activity of Ia to Il could be attributed to the activity of the thrombolytic peptide, and on the other hand the linking of the thrombolytic peptide ARPAK (SEQ. ID NO. 4), GRPAK (SEQ. ID NO. 5), RPAK (SEQ. ID NO. 3) or PAK and the targeting peptide RGDS (SEQ. ID NO. 11), RGDV (SEQ. ID NO. 12) or RGDF (SEQ. ID NO. 13) to the free radical scavenger TMMZ via Lys did not abate the activity of the thrombolytic peptide.

TABLE 3

In vitro thrombolytic activity by 2 h treatment of Ia-Il

| Compounds | Weight reduction in thrombus (Mean ± SD mg) |
| --- | --- |
| Normal saline | 16.67 ± 1.86 [a] |
| urokinase | 58.33 ± 4.08[a] |
| ARPAK (SEQ. ID NO. 4) | 26.35 ± 3.10 |
| Ia | 28.50 ± 2.59 |
| Ib | 28.17 ± 2.31 |
| Ic | 27.33 ± 2.07 |
| GRPAK (SEQ. ID NO. 5) | 15.47 ± 2.61 |
| Id | 14.17 ± 3.55 |
| Ie | 14.00 ± 1.41 |
| If | 15.29 ± 3.36 |
| RPAK (SEQ. ID NO. 3) | 26.01 ± 3.11 |
| Ig | 27.83 ± 2.56 |
| Ih | 29.33 ± 3.01 |
| Ii | 24.83 ± 1.17 |
| PAK | 26.67 ± 3.20 |
| Ij | 26.16 ± 3.15 |
| Ik | 25.00 ± 1.54 |
| Il | 25.83 ± 2.31 | n = 6; [a]) p <0.01, vs. Ia-Il

Experimental Example 4. In Vivo Thrombolysis Experiments for Compounds Ia to Il of the Present Invention SD rats (male, 220 to 230 g) were anaesthetized by intraperitoneal injection of a urethane solution at a dosage of 1200 mg/kg. The anaesthetized rats were fixed in a supine position, and the right common carotid artery was dissected, clamped at the proximal end with an arterial clip, and penetrated with a suture at the proximal and distal ends, respectively. The suture at the distal end is clipped tightly by a hemostatic clamp at the fur. Cannulation was performed at the distal end, the arterial clamp was removed, and about 1 ml arterial blood was discharged into a 1 ml eppendorf. 0.1 ml rat arterial blood was injected into a vertically fixed glass tube (15 mm in length, with an inner diameter of 2.5 mm and an outer diameter of 5.0 mm, sealed with a rubber stopper at the bottom), into which was immediately inserted a thrombus immobilization screw made of stainless steel. The thrombus immobilization screw, formed by coiling of a stainless steel wire having a diameter of 0.2 mm, had a spiral part of 12 mm in length, 15 coils each having a diameter of 1.8 mm, and a stem of 1.0 mm in length which was connected to the spiral part and had a question-mark-like shape. 15 min after the blood was coagulated, the rubber stopper at the bottom of the glass tube was removed, the stem of the thrombus immobilization screw was nipped by forceps, and the thrombus-wrapped thrombus immobilization screw was carefully taken out of the glass tube and then accurately weighed.

A bypass cannula was composed of 3 segments. The middle segment was a polyethylene tubing having a length of 60.0 mm and an inner diameter of 3.5 mm. The segments on both ends were similar polyethylene tubes having a length of 100.0 mm, an inner diameter of 1.0 mm and an outer diameter of 2.0 mm, one end of which was pulled to form a tip, with an outer diameter of 1.0 mm, that could be inserted into the rat carotid artery or vein, and the other end of which was sheathed by a polyethylene tube having a length of 7.0 mm and an outer diameter of 3.5 mm (thickened in order to be inserted into the polyethylene tubing of the middle segment). The inner wall of the 3-segment cannula was entirely silylated (with 1% silicone oil in ethyl ether). The thrombus-wrapped thrombus immobilization screw was placed into the polyethylene tubing of the middle segment, and both ends of the tubing sheathed the thickened ends of the two polyethylene tubes. The cannula was filled with a heparin solution in normal saline (50 IU/kg) through the tip end by using an injector and was ready for use. The trachea of the anaesthetized rat was then dissected and tracheal cannulation was performed. The left external carotid vein of the rat was dissected, and penetrated with a suture at the proximal and distal ends, respectively. An uneven open incision was careful made on the exposed left external carotid vein, and the tip of the bypass cannula prepared as described above was inserted into the proximal end of the open incision in the left external carotid vein, away from the stem of the thrombus immobilization screw in the middle segment of the bypass cannula (which accommodated the accurately weighed thrombus immobilization screw). A precise amount of heparin in saline (50 IU/kg) was injected through the tip at the other end by using an injector. At this moment, without removing the injector from the ethylene tube, the tubing between the injector and the polyethylene tube was clamped with forceps. The blood flow was stopped by clamping the proximal end of the right common carotid artery with an arterial clip, and an uneven open incision was cut carefully across the common carotid artery near the clip. The injector was pulled out of the tip of the polyethylene tube, and the tip of the polyethylene tube was then inserted into the proximal end of the artery open incision. Both ends of the bypass cannula were fixed to the artery or vein with #4 sutures.

Normal saline (3 mL/kg), or a urokinase solution in normal saline (at a dose of 20000 IU/kg), or a solution of one of compounds Ia-Il in normal saline (at a dose of 0.1 μmol/kg), or a solution ARPAK (SEQ. ID NO. 4), GRPAK (SEQ. ID NO. 5), RPAK (SEQ. ID NO. 3) or PAK in normal saline (at a dose of 1 μmol/kg), was connected to a position close to the vein away from the thrombus immobilization screw by using a scalp needle to puncture the middle segment of the bypass cannula (which accommodated the accurately weighed thrombus immobilization screw). The artery clip was then removed to allow blood to flow from the artery to the vein through the bypass cannula. A rat arteriovenous bypass thrombolysis model was thus established. The solution in the injector was slowly injected into blood, enabling normal saline (blank control), urokinase (positive control), ARPAK (SEQ. ID NO. 4), GRPAK (SEQ. ID NO. 5), RPAK (SEQ. ID NO. 3) or PAK (component control), or Ia-Il to act on the thrombus through blood circulation in the order of vein-heart-artery. The process was timed at the beginning of injection, and the thrombus immobilization screw was removed from the bypass cannula after 1 h and accurately weighed. The difference in the mass of the thrombus immobilization screw in the rat bypass cannula before and after the administration was determined, and the experimental results are shown in Table 4.

As shown in the experimental results, not only did compounds Ia-Ic, obtained by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, exhibit thrombolytic activity at a dosage of 0.1 μmol/kg, the potency of their activity was also comparable to that of the corresponding thrombolytic peptide ARPAK (SEQ. ID NO. 4), GRPAK (SEQ. ID NO. 5), RPAK (SEQ. ID NO. 3) or PAK at a dosage of 1 μmol/kg. As such, by linking the thrombolytic peptide ARPAK (SEQ. ID NO. 4), GRPAK (SEQ. ID NO. 5), RPAK (SEQ. ID NO. 3) or PAK and the targeting peptide RGDS (SEQ. ID NO. 11), RGDV (SEQ. ID NO. 12) or RGDF (SEQ. ID NO. 13) to the free radical scavenger TMMZ via Lys, the effective dosage could be decreased by 10 folds.

TABLE 4

In vivo thrombolytic activity of Ia-Il

| Compounds | Weight reduction in thrombus (Mean ± SD mg) |
|---|---|
| Normal saline | 11.05 ± 1.51 [a] |
| urokinase | 18.02 ± 2.32[a] |
| ARPAK (SEQ. ID NO. 4) | 15.20 ± 2.55 |
| Ia | 15.39 ± 3.19 |
| Ib | 14.35 ± 2.95 |
| Ic | 15.79 ± 3.07 |
| GRPAK (SEQ. ID NO. 5) | 15.47 ± 2.61 |
| Id | 14.17 ± 3.55 |
| Ie | 14.00 ± 1.41 |
| If | 15.29 ± 3.36 |
| RPAK (SEQ. ID NO. 3) | 15.67 ± 2.61 |
| Ig | 16.35 ± 2.42 |
| Ih | 15.37 ± 1.82 |
| Ii | 15.73 ± 2.95 |
| PAK | 15.00 ± 2.61 |
| Ij | 14.89 ± 1.84 |
| Ik | 15.47 ± 2.61 |
| Il | 16.21 ± 2.84 | n = 10; [a]) p <0.01 vs. Ia-Il

Experimental Example 5. In Vivo Anti-Thrombus Experiments for Compounds Ia to Il of the Present Invention SD rats (male, 220 to 230 g) were randomly divided into groups with 11 rats in each group. The rats were fed at a resting state for 1 day and fasted overnight. The rats were given normal saline (at a dose of 3 mL/kg), a solution of one of compounds Ia-Il in normal saline (at a dose of 0.1 μmol/kg), a solution of the targeting peptide RGDS (SEQ. ID NO. 11), RGDV (SEQ. ID NO. 12) or RGDF (SEQ. ID NO. 13) in normal saline (at a dose of 10 μmol/kg), or aspirin (at a dose of 33 mg/kg) by gavage. After 30 min, the rats were anesthetized with a 20% urethane solution, and the right carotid artery and the left carotid vein were dissected. A cannula was filled with sodium heparin in normal saline, and one end thereof was inserted into the left vein, while the other end was injected with a certain amount of sodium heparin for anticoagulation with an injector and then inserted into the right artery. Blood flew from the right artery to the left vein through the polyethylene tubing, and the thread attached with thrombus was taken out after 15 min and the weight thereof was recorded. The wet thrombus weight was determined by subtracting the thread weight from the total weight. The results are shown in Table 5.

As shown in the experimental results, not only did compounds Ia-Ic, obtained by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, exhibit anti-thrombus activity at an oral dosage of 0.1 μmol/kg, the potency of their activity was also comparable to that of the targeting peptide RGDS (SEQ. ID NO. 11), RGDV (SEQ. ID NO. 12) or RGDF (SEQ. ID NO. 13) at a dosage of 10 μmol/kg. As such, by linking the thrombolytic peptide ARPAK (SEQ. ID NO. 4), GRPAK (SEQ. ID NO. 5), RPAK (SEQ. ID NO. 3) or PAK and the targeting peptide RGDS (SEQ. ID NO. 11), RGDV (SEQ. ID NO. 12) or RGDF (SEQ. ID NO. 13) to the free radical scavenger TMMZ via Lys, the effective dosage could be decreased by 100 folds.

TABLE 5

In vivo anti-thrombus activity of Ia-Il

| Compounds | Wet weight of thrombus (Mean ± SD mg) |
|---|---|
| normal saline | 27.38 ± 2.62 [a] |
| aspirin | 12.85 ± 2.49 [a] |
| RGDS (SEQ. ID NO. 11) | 20.02 ± 2.35 |
| RGDV (SEQ. ID NO. 12) | 21.26 ± 2.07 |
| RGDF (SEQ. ID NO. 13) | 19.55 ± 2.21 |
| Ia | 24.32 ± 2.10 |
| Ib | 20.14 ± 2.45 |
| Ic | 20.50 ± 2.26 |
| Id | 19.46 ± 1.84 |
| Ie | 16.92 ± 1.53 |
| If | 17.99 ± 2.47 |
| Ig | 17.89 ± 2.05 |
| Ih | 18.24 ± 1.89 |
| Ii | 17.79 ± 2.02 |
| Ij | 19.45 ± 1.79 |
| Ik | 22.25 ± 2.25 |
| Il | 19.32 ± 2.56 | n = 11; [a]) p <0.01 vs. Ia-Il

Establishment of Animal Models for Assessment of the Efficacy of the Compounds According to the Present Invention in Treating Stroke Patients (1) The rat experimental protocol described herein was in accordance with the Geneva guidance in animal experiments and approved by the college ethical committee. Clean grade health male SD rats, weighing 280 to 305 g, were purchased from Vital River Laboratories of Experimental Animals. These rats were randomly used for preparation of thrombus or establishment of stroke models.

(2) A 10% chloral hydrate solution was injected intraperitoneally into SD rats at a dosage of 400 mg/kg body weight for anesthesia. The carotid artery was dissected, 15 mL fresh arterial blood was drawn, and aliquots of 10 μL each were then added into 1.5 mL EP vials. The thrombus formed was kept at RT for 2 h and then in a −20° C. refrigerator for 22 h. When used, 0.5 mL saline was added to the thrombus which was broken up by using a glass rod, so as to prepare a thrombus homogenate suspension solution, with a volume of about 0.1 $mm^3$ for each thrombus pieces.

(3) A 10% chloral hydrate solution was injected intraperitoneally into SD rats at a dosage of 400 mg/kg body weight for anesthesia. The carotid artery was dissected, 15 mL fresh arterial blood was drawn, and aliquots of 10 μL each were then added into 1.5 mL EP vials. The thrombus formed was firstly kept at RT for 24 h. When used, 0.5 mL saline was added to the thrombus which was broken up by using a glass rod, so as to prepare a thrombus homogenate suspension solution, with a volume of about 0.1 $mm^3$ for each thrombus pieces.

(4) A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incisions in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid internal artery was ligated, the arterial clips on the carotid internal artery and the common carotid artery were released, and blood flow was restored. The main jugular external vein was dissected, and normal saline (blank control) or a solution of the compounds of the present invention in normal saline was infused through the jugular external vein. After the wound was stitched up, 20,000 IU penicillin was intramuscularly injected for prevention from infection. The model of immediate treatment after the onset of stroke was thus established.

(5) A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incision in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 4 h, 6 h or 24 h, normal saline (blank control) or a solution of the compounds of the present invention in normal saline was infused through the tail vein. The rat models of 4 h, 6 h, and 24 h post-onset treatment of stroke were thus established.

Establishment of Animal Models for Assessment of the Efficacy of the Compounds According to the Present Invention after 4 h, 6 h, and 24 h from Stroke Onset (1) The efficacy after immediate, 4 h post-onset treatment, and 6 h post-onset treatment of stroke rats with the compounds according to the present invention means the result of scoring of rats' behaviors 24 h after the rats regained consciousness. The behaviors include the walking manner, the degree of drooping of the right eye lid, the degree of tail stiffness, tension of muscles, the degree of head tilting, the support force of limbs, and the death status.

(2) The efficacy in 24 h post-onset treatment of stroke in rats with the compounds according to the present invention means the result of observation of rats' behaviors 24 h after the rats regained consciousness. The behaviors include the walking manner, the degree of drooping of the right eye lid, the degree of tail stiffness, tension of muscles, the degree of head tilting, the support force of limbs, and the death status.

(3) The efficacy in rats with stroke treated once with the compound of the present invention was compared to the efficacy in rats with stroke treated once with saline.

(4) Rats with stroke with continuous treatment were injected with the compounds of the present invention in normal saline every 24 h through the tail vein. On the next day, the videos were recorded, and comparison was made among the recorded results.

Test results of the compounds Ia to Il according to the present invention in the above animal models are as follows:

Experimental Example 6. Experiments on Rats that Received Immediate Treatment after Stroke Onset with Compounds Ia to Il of the Present Invention The in vivo anti-stroke activity of the present invention was represented by neural function scores, with a lower score indicating higher activity. A 10% chloral hydrate solution (400 mg/kg) was injected intraperitoneally into SD male rats (250-300 g) for anesthesia. An open incision of 2 cm in length was longitudinally made slightly on the right to the center of the neck, and the right common carotid artery trunk, carotid external artery and carotid internal artery were dissected along the margin of the inner side of sternocleidomastoid muscles. The open incisions in the carotid internal artery and the proximal end of the common carotid artery were occluded respectively with noninvasive arterial clips. A small open incision was made across the carotid external artery, and the distal end of the carotid external artery was ligated. The arterial clip at the proximal end of the carotid external artery was released, and 10 μl blood was drawn before the proximal end of the common carotid artery was again occluded with the noninvasive arterial clip. The 10 μl blood drawn was placed in a 1 mL EP vial and kept at RT for 30 min for coagulation of blood, and then transferred into a −20° C. refrigerator for 1 h to allow coagulation. After 1 h, the blood clots were taken out, into which 1 mL saline was added, and then broken into uniform microthrombus by using a steel spatula. The microthrombus suspension was then transferred to a 1 mL injector until use. At the same time when the clip on the carotid internal artery of the rat was released, 1 mL thrombus suspension in the injector was slowly injected from the carotid external artery of the rat to its proximal end, and the suspension was injected into the brain of the rat through the carotid internal artery. Subsequently, the proximal end of the carotid external artery was ligated, the arterial clips on the carotid internal artery and the common carotid artery were released, and blood flow was restored. The jugular common vein of the rats was dissected. The vein was immediately ligated, 3 drops of penicillin was dropped at the wound site, the wound was stitched up, and the animals were allowed to come around, as the sham operation group. Or injection of urokinase in normal saline (positive control group, at a dosage of 20000 IU/kg), normal saline (blank control group, at a dosage of 3 ml/kg), TMMZ in normal saline (component control group, at a dosage of 1 μmol/kg), a thrombolytic peptide ARPAK (SEQ. ID NO. 4), GRPAK (SEQ. ID NO. 5), RPAK (SEQ. ID NO. 3) or PAK in normal saline (component control group, at a dosage of 1 μmol/kg), or one of compounds Ia-Il in normal saline (at a dosage of 0.1 μmol/kg) was carried out. 24 h after the rats were awake, the degree of damage in the neural function was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Table 6.

As shown in the experimental results, the compounds Ia-Ic, obtained by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, exhibited anti-stroke activity at a dosage of 0.1 μmol/kg, whereas urokinase did not exhibit anti-stroke activity at a dosage of 20000 IU/kg. Similarly, the thrombolytic peptide ARPAK (SEQ. ID NO. 4), GRPAK (SEQ. ID NO. 5), RPAK (SEQ. ID NO. 3) or PAK did not exhibit anti-stroke activity at a dosage of 1 μmol/kg. As such, by linking the thrombolytic peptide ARPAK (SEQ. ID NO. 4), GRPAK (SEQ. ID NO. 5), RPAK (SEQ. ID NO. 3) or PAK and the targeting peptide RGDS (SEQ. ID NO. 11), RGDV (SEQ. ID NO. 12) or RGDF (SEQ. ID NO. 13) to the free radical scavenger TMMZ via Lys, the compounds were provided with an anti-stroke function. Specially, at the dosage of 1 μmol/kg, 4 compounds had anti-stroke activity comparable to that of urokinase at a dosage of 20000 IU/kg, and 8 compounds had remarkably higher anti-stroke activity than that of urokinase at a dosage of 20000 IU/kg.

TABLE 6

In vivo anti-stroke activity of Ia-Ic

| Compounds | Neural function scores (Mean ± SD) |
| --- | --- |
| normal saline | 3.07 ± 1.04 |
| urokinase | 1.90 ± 1.37 [a] |
| TMMZ | 2.83 ± 0.75 [a] |

TABLE 6-continued

In vivo anti-stroke activity of Ia-Ic

| Compounds | Neural function scores (Mean ± SD) |
|---|---|
| ARPAK (SEQ. ID NO. 4) | 2.21 ± 0.94 [a] |
| Ia | 1.00 ± 1.01 [b] |
| Ib | 0.56 ± 1.01 [c] |
| Ic | 0.89 ± 1.36 [c] |
| GRPAK (SEQ. ID NO. 5) | 2.38 ± 0.92 [a] |
| Id | 1.22 ± 1.32 [b] |
| Ie | 0.44 ± 1.01 [c] |
| If | 0.60 ± 0.84 [c] |
| RPAKI (SEQ. ID NO. 3) | 2.38 ± 0.97 [a] |
| Ig | 1.00 ± 1.19 [b] |
| Ih | 1.33 ± 1.22 [b] |
| Ii | 0.87 ± 1.05 [c] |
| PAK | 2.42 ± 0.95 [a] |
| Ij | 0.90 ± 1.10 [c] |
| Ik | 0.56 ± 0.53 [c] |
| Il | 0.50 ± 0.53 [c] | n = 10; [a] p >0.05 vs. normal saline; [b] p >0.05 vs. urokinase; p <0.01 vs. normal saline; [c] p <0.01 vs. normal saline or urokinase

Experimental Example 7. Experiments on Cerebral Infarction Volume in Rats that Received Immediate Treatment with Compounds Ia to Il of the Present Invention after the Stroke Onset After the rats were awake for 24 h and assessed for their degree of damage in neural function in Experimental example 6, they were anesthetized with urethane followed by immediate decapitation and removal of the brain. Brain tissues were kept in a −20° C. refrigerator for 2 h, and coronal sections of about 2 mm were successively sliced from the prefrontal end for a total of 6 sections, and then placed into a 2% TTC solution to incubate in darkness at 37° C. for 30 min. The color change in brain sections was observed: normal brain tissues were stained red by TTC, while ischemic brain tissues, i.e., brain tissues with infracts, appeared in a white color. Photographs were taken by using a digital camera and processed with SPSS statistics software, and the volume of infarction in brain tissues and the volume of normal brain tissues in the coronal sections were calculated. The experimental results are shown in Table 7.

As shown in the experimental results, not only did compounds Ia-Ic, obtained by linking a thrombolytic peptide ARPAK (SEQ. ID NO. 4), GRPAK (SEQ. ID NO. 5), RPAK (SEQ. ID NO. 3) or PAK and a targeting peptide RGDS (SEQ. ID NO. 11), RGDV (SEQ. ID NO. 12) or RGDF (SEQ. ID NO. 13) to a free radical scavenger TMMZ via Lys, exhibit an effect in reduction of the cerebral infarction volume in rats with stroke at a dosage of 0.1 μmol/kg, such an effect was substantially more potent than that of urokinase at a dosage of 20000 IU/kg.

TABLE 7

Volume of cerebral infarction in stroke rats treated with Ia-Ic

| Compounds | Percentage of infarction volume (Mean ± SD %) |
|---|---|
| normal saline | 22.92 ± 2.74 |
| urokinase | 11.00 ± 2.42 [b] |
| TMMZ | 22.96 ± 2.43 [a] |
| ARPAK (SEQ. ID NO. 4) | 22.00 ± 2.20 [a] |
| Ia | 7.21 ± 0.82 |
| Ib | 7.13 ± 0.83 |
| Ic | 7.40 ± 1.65 |
| GRPAK (SEQ. ID NO. 5) | 21.77 ± 2.46 [a] |
| Id | 8.21 ± 1.91 |
| Ie | 6.44 ± 1.51 |
| If | 7.47 ± 1.31 |
| RPAK (SEQ. ID NO. 3) | 22.11 ± 2.25 [a] |
| Ig | 6.40 ± 0.28 |
| Ih | 7.35 ± 1.14 |
| Ii | 7.06 ± 1.08 |
| PAK | 22.07 ± 2.40 [a] |
| Ij | 6.84 ± 0.82 |
| Ik | 7.86 ± 1.02 |
| Il | 6.56 ± 0.41 | n = 10; [a] p >0.05, vs. normal saline; [b] p <0.01 vs. normal saline and Ia-Ic

Experimental Example 8. Experiments on Rats that Received Immediate Treatment with Different Dosages of Compound Ie of the Present Invention after the Stroke Onset After analysis and comparison of all experimental results in the present invention, compound Ie was used as the representative, in order to demonstrate the dose-dependent therapeutic effect exhibited by compounds Ia to Il in the above experiments. It should be noted that other compounds of Ia to Il could achieve similar dose-dependent therapeutic effect as compound Ie did, since the other compounds of Ia to Il had achieved the same effect as compound Ie in NO free radical scavenging, euglobulin clot lysis, thrombolysis, anti-thrombus action, and treatment of stroke in rats.

A 10% chloral hydrate solution (400 mg/kg) was injected intraperitoneally into male SD rats (250 to 300 g) for anesthesia. An incision of about 2 cm in length was longitudinally made slightly on the right to the center of the neck, and the right carotid common artery, carotid external artery and carotid internal artery were dissected along the margin of the inner side of sternocleidomastoid muscles. The open incision in the carotid internal artery and the proximal end of the common carotid artery were occluded respectively with noninvasive arterial clips. A small incision was made on the carotid external artery, and the distal end of the carotid external artery was ligated. The arterial clip at the proximal end of the carotid external artery was released, and 10 μl blood was drawn before the proximal end of the common carotid artery was again occluded with a noninvasive arterial clip. The 10 μl blood drawn was placed in a 1 mL EP vial and kept at RT for 30 min until coagulation of blood, and then transferred into a −20° C. refrigerator for 1 h to allow solid coagulation. After 1 h, the blood clots were taken out, added into 1 mL saline, and then broken into relatively uniform microthrombus by using a steel spatula. The microthrombus suspension was then transferred into a 1 mL injector until use. At the same time when the clip on the carotid internal artery of the rat was released, the 1 mL thrombus suspension in the injector was slowly injected from the carotid external artery of the rat to its proximal end, and then was injected into the brain of the rat through the carotid internal artery. Subsequently, the proximal end of the carotid external artery was ligated, the arterial clips on the carotid internal artery and the carotid common artery were released, and blood flow was restored. Injection of urokinase in normal saline (positive control group, at a dosage of 20000 IU/kg), tPA in normal saline (positive control group, at a dosage of 3 mg/kg), normal saline (blank control group, at a dosage of 3 mL/kg), or compound Ie in normal saline (at a dosage of 1 μmol/kg, 0.1 μmol/kg or 0.01 μmol/kg) was carried out. 24 h after the rats were awake, the degree of damage in neural function was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Table 8. As shown in the results, in rats receiving immediate treatment after the onset of stroke with 1 μnmol/kg, 0.1 μnmol/kg and 0.01 μnmol/kg compound Ie, the percentage of rats with a neural function score of 0 was 60%, 30%, and 0%, respectively; and the percentage of rats with a neural function score of 1 was 20%, 30%, and 10%, respectively. Thus, it shows that the anti-stroke activity of compound Ie was dose-dependent. Further, in rats with stroke treated with 20000 IU/kg urokinase and 3 mg/kg tPA, the percentage of rats with a neural function score of 0 was 10% and 40%, respectively, and the percentage of rats with a neural function score of 1 was 50% and 10%, respectively; in comparison, the efficacy of 1 μnmol/kg and 0.1 μnmol/kg compound Ie was obviously superior.

Experimental Example 9. Experiments on Rats Receiving 6 Successive Treatments with 1 μmol/Kg Compound Ie of the Present Invention 4 Hours after the Onset of Stroke The efficacy was represented by neural function scores, and a lower score indicates higher efficacy. A 10% chloral hydrate solution was injected intraperitoneally into male SD rats at a dosage of 400 mg/kg body weight for anesthesia. A longitudinal incision was made at the center of the neck, and the right carotid common artery trunk was dissected (about 3 cm in length). Carotid external artery branches were each dissected and ligated at the hyoid level, and the carotid internal artery was dissected at the swollen part of the neck. The open incision in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 4 h, compound Ie in normal saline (at a dosage of 1 μmol/kg, n=1), urokinase in normal saline (at a dosage of 20000 IU/kg, n=6) or tPA in normal saline (at a dosage of 3 mg/kg, n=6) was infused through the tail vein. Infusion of compound Ie in normal saline through rat tail vein was carried out once per day for 6 consecutive days, observed for 7 days. The rats were compared to themselves each day, and evaluated for degree of damage in neural function by the Zealonga method. Alternatively, infusion of urokinase in normal saline through rat tail vein was carried out once per day for two consecutive days, the rats were compared to themselves each day, and evaluated for the degree of damage in neural function by the Zealonga method. Alternatively, infusion of tPA in normal saline through rat tail vein was carried out once per day for two consecutive days, the rats were compared to themselves each day, and evaluated for the degree of damage in neural function by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward

TABLE 8

In vivo anti-stroke activity of compound Ie of the present invention at different dosages

| Compounds | | Daily neural function scores (Mean ± SD) and number of rats scored | | | | | |
|---|---|---|---|---|---|---|---|
| | | Score 0 | Score 1 | Score 2 | Score 3 | Score 4 | Score 5 |
| normal saline | | 0 | 2 | 3 | 5 | 1 | 0 |
| urokinase | | 1 | 5 | 0 | 3 | 1 | 0 |
| tPA | | 4 | 1 | 1 | 3 | 1 | 0 |
| Ie | 1 μnmol/kg | 6 | 2 | 0 | 2 | 0 | 0 |
| | 100 nmol/kg | 3 | 3 | 0 | 3 | 1 | 0 |
| | 10 nmol/kg | 0 | 1 | 6 | 1 | 1 | 0 | n = 10;
a) p < 0.01 vs. normal saline the undamaged side, 4 indicated involuntary walking with disturbance of consciousness, and 5 indicated death. The experimental results are shown in Tables 9-1, 9-2 and 9-3.

The data in Table 9-1 demonstrated that, in rats that received treatment 4 h after the onset of stroke with one dose of 1 µmol/kg compound Ie each day for 6 consecutive days, excluding one that accidentally died on day 2, 8 out of the remaining 10 rats recovered to have no sign of loss in neural function while the rest 2 rats had only the sign of slight loss in neural function. Thus, compound Ie exhibited therapeutic effect at a dosage of 1 µmol/kg in stroke beyond the golden treatment window.

TABLE 9-1

Efficacy in rats receiving treatment with 1 µmol/kg compound Ie of the present invention 4 h after the onset of stroke

| Time of scoring | Daily neural function scores (Mean ± SD) and number of rats scored | | | | | |
|---|---|---|---|---|---|---|
| | Score 0 | Score 1 | Score 2 | Score 3 | Score 4 | Score 5 |
| Day 1 | 1 rat | 4 rats | 4 rats | 1 rat | 1 rat | 0 |
| Day 2 | 3 rats | 5 rats | 1 rat | 1 rat | 0 | 1 rat |
| Day 3 | 5 rats | 5 rats | 0 | 0 | 0 | 0 |
| Day 4 | 7 rats | 3 rats | 0 | 0 | 0 | 0 |
| Day 5 | 8 rats | 2 rats | 0 | 0 | 0 | 0 |
| Day 6 | 8 rats | 2 rats | 0 | 0 | 0 | 0 |
| Day 7 | 8 rats | 2 rats | 0 | 0 | 0 | 0 |

The data in Table 9-2 demonstrated that, in rats that received treatment 4 h after the onset of stroke with one dose of 20000 IU/kg urokinase each day, 2 out of 6 rats died within 48 h. Upon autopsy on the dead rats, both showed hemorrhage in internal organs, particularly severe hemorrhage in lungs. Therefore, the dosage regime was discontinued after two doses. No rats after receiving two doses recovered to have no sign of loss in neural function or to have only the sign of slight loss in neural function.

TABLE 9-2

Efficacy in rats receiving treatment with 20000 IU/kg urokinase 4 h after the onset of stroke

| Time of scoring | Daily neural function scores (Mean ± SD) and number of rats scored | | | | | |
|---|---|---|---|---|---|---|
| | Score 0 | Score 1 | Score 2 | Score 3 | Score 4 | Score 5 |
| Day 1 | | | 2 rats | 3 rats | | 1 rat |
| Day 2 | | | 3 rats | 1 rat | | 1 rat |

The data in Table 9-3 demonstrated that, in rats that received treatment 4 h after the onset of stroke with one dose of 3 mg/kg tPA each day, 1 out of 6 rats died within 24 h. Upon autopsy on the dead rat, it showed hemorrhage in internal organs, particularly severe hemorrhage in lungs. Therefore, the dosage regime was discontinued after two doses. No rats after receiving two doses recovered to have no sign of loss in neural function, and 2 rats recovered to have only the sign of slight loss in neural function.

TABLE 9-3

Efficacy in rats receiving treatment with 3 mg/kg tPA 4 h after the onset of stroke

| Time of scoring | Daily neural function scores (Mean ± SD) and number of rats scored | | | | | |
|---|---|---|---|---|---|---|
| | Score 0 | Score 1 | Score 2 | Score 3 | Score 4 | Score 5 |
| Day 1 | | | 2 rats | 3 rats | | 1 rat |
| Day 2 | | 2 rats | 2 rats | 1 rat | | |

In summary of the data in Table 9-1, 9-2 and 9-3, even for rats that received treatment 4 h after the onset of stroke for two consecutive days, compound Ie at a dosage of 1 µmol/kg showed much higher efficacy than urokinase at a dosage of 20000 IU/kg and tPA at a dosage of 3 mg/kg.

Experimental Example 10. Experiments on Rats Receiving 6 Successive Treatments with 1 µmol/Kg Compound Ie of the Present Invention 6 h after the Onset of Stroke The efficacy was represented by neural function scores, and a lower score indicates higher efficacy. A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incision in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 6 h, compound Ie in normal saline (at a dosage of 1 µmol/kg, n=11), urokinase in normal saline (at a dosage of 20000 IU/kg, n=6) or tPA in normal saline (at a dosage of 3 mg/kg, n=6) was infused through the tail vein. Infusion of compound Ie in normal saline through rat tail vein was carried out once per day for 6 consecutive days, observed for 7 days. The rats were compared to themselves each day, and evaluated for the degree of damage in neural function by the Zealonga method. Alternatively, infusion of urokinase in normal saline through rat tail vein was carried out once per day for two consecutive days, the rats were compared to themselves each day, and evaluated for the degree of damage in neural function by the Zealonga method. Alternatively, infusion of tPA in normal saline through rat tail vein was carried out once per day for two consecutive days, the rats were compared to themselves each day, and evaluated for the degree of damage in neural function by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Tables 10-1, 10-2 and 10-3.

The data in Table 10-1 demonstrated that, in rats that received treatment 6 h after the onset of stroke with one dose of 1 µmol/kg compound Ie each day for 6 consecutive days, excluding two that accidentally died on day 2, 2 out of the remaining 9 rats recovered to have no sign of loss in neural function, one rat recovered to have only the sign of slight loss in neural function, and 6 showed the sign of tail-chasing walking in circles toward the undamaged side. Thus, compound Ie exhibited therapeutic effect at a dosage of 1 µmol/kg in stroke beyond the golden treatment window.

TABLE 10-1

Efficacy in rats receiving treatment with 1 µmol/kg compound Ie of the present invention 6 h after the onset of stroke

| Time of scoring | Daily neural function scores (Mean ± SD) and number of rats scored | | | | | |
| --- | --- | --- | --- | --- | --- | --- |
| | Score 0 | Score 1 | Score 2 | Score 3 | Score 4 | Score 5 |
| Day 1 | 0 | 3 rats | 5 rats | 2 rats | 1 rat | 0 |
| Day 2 | 0 | 2 rats | 2 rats | 4 rats | 1 rat | 2 rats |
| Day 3 | 0 | 2 rats | 4 rats | 2 rats | 1 rat | 0 |
| Day 4 | 1 rat | 1 rat | 2 rats | 4 rats | 0 | 0 |
| Day 5 | 1 rat | 1 rat | 2 rats | 4 rats | 0 | 0 |
| Day 6 | 2 rats | 1 rat | 1 rat | 4 rats | 1 rat | 0 |
| Day 7 | 2 rats | 1 rat | 0 | 6 rats | 0 | 0 |

The data in Table 10-2 demonstrated that, in rats that received treatment 6 h after the onset of stroke with one dose of 20000 IU/kg urokinase each day, 4 out of 6 rats died within 24 h. Upon autopsy on the dead rats, all showed hemorrhage in internal organs, particularly severe hemorrhage in lungs. Therefore, the dosage regime was discontinued after two doses. One rat after receiving two doses recovered to have no sign of loss in neural function, and one rat showed the sign of involuntary walking with disturbance of consciousness.

TABLE 10-2

Efficacy in rats receiving treatment with 20000 IU/kg urokinase 6 h after the onset of stroke

| Time of scoring | Daily neural function scores (Mean ± SD) and number of rats scored | | | | | |
| --- | --- | --- | --- | --- | --- | --- |
| | Score 0 | Score 1 | Score 2 | Score 3 | Score 4 | Score 5 |
| Day 1 | | 1 rat | | | 1 rat | 4 rats |
| Day 2 | 1 rat | | | | 1 rat | |

The data in Table 10-3 demonstrated that, in rats that received treatment 6 h after the onset of stroke with one dose of 3 mg/kg tPA each day, 2 out of 6 rats died within 24 h. Upon autopsy on the dead rats, both showed hemorrhage in internal organs, particularly severe hemorrhage in lungs. Therefore, the dosage regime was discontinued after two doses. No rats after receiving two doses recovered to have no sign of loss in neural function, 2 recovered to have only the sign of slight loss in neural function, one rat showed the sign of tail-chasing walking in circles toward the undamaged side, and one rat showed the sign of involuntary walking with disturbance of consciousness.

TABLE 10-3

Efficacy in rats receiving treatment with 3 mg/kg tPA 6 h after the onset of stroke

| Time of scoring | Daily neural function scores (Mean ± SD) and number of rats scored | | | | | |
| --- | --- | --- | --- | --- | --- | --- |
| | Score 0 | Score 1 | Score 2 | Score 3 | Score 4 | Score 5 |
| Day 1 | | 1 rat | 1 rat | 1 rat | 1 rat | 2 rats |
| Day 2 | | 2 rats | | 1 rat | 1 rat | |

In summary of the data in Table 10-1, 10-2 and 10-3, even for rats that received treatment 6 h after the onset of stroke for two consecutive days, compound Ie at a dosage of 1 µmol/kg showed much higher efficacy than urokinase at a dosage of 20000 IU/kg and tPA at a dosage of 3 mg/kg.

Experimental Example 11. Experiments on Rats Receiving Treatments 6 h after the Onset of Stroke with Compound Ie of the Present Invention at an Initial Dosage of 5 µmol/Kg and 5 Subsequent Dosages of 2 µmol/Kg Each The efficacy was represented by neural function scores, and a lower score indicates higher efficacy. A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incision in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 6 h, compound Ie in normal saline (at an initial dosage of 5 µmol/kg, n=12) was infused through the tail vein. Then, infusion of compound Ie in normal saline (at a dosage of 2 µmol/kg, n=12) through rat tail vein was carried out once per day for 6 consecutive days, observed for 7 days. The rats were compared to themselves each day, and evaluated for the degree of damage in neural function by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Table 11.

The data in Table 11 demonstrated that, efficacy was shown in rats that received treatment 6 h after the onset of stroke with one dose of 5 µmol/kg compound Ie on day 1 and one dose of 2 µmol/kg compound Ie per day for the following 5 days. Among the 12 rats that received the treatment, two were dead, while 6 out of the remaining 10 rats recovered to have no sign of loss in neural function, two had only the sign of slight loss in neural function, one showed the sign of walking toward the undamaged side, and one showed the sign of tail-chasing walking in circles toward the undamaged side. Thus, continuous treatment with compound Ie showed therapeutic effect on stroke beyond the golden treatment window.

TABLE 11

Efficacy in rats receiving treatment with compound Ie of the present invention 6 h after the onset of stroke

| Rat No. | Daily neural function scores (Mean ± SD) | | | | | | |
|---|---|---|---|---|---|---|---|
| | Day 1 | Day 2 | Day 3 | Day 4 | Day 5 | Day 6 | Day 7 |
| 1 | 1 | 1 | 0 | 0 | 0 | 0 | 0 |
| 2 | 1 | 0 | 0 | 0 | 0 | 0 | 0 |
| 3 | 3 | 1 | 5 | | | | |
| 4 | 2 | 1 | 1 | 0 | 0 | 0 | 0 |
| 5 | 0 | 0 | 0 | 0 | 0 | 0 | 0 |
| 6 | 2 | 2 | 1 | 0 | 0 | 0 | 0 |
| 7 | 5 | | | | | | |
| 8 | 2 | 1 | 1 | 1 | 1 | 1 | 1 |
| 9 | 0 | 0 | 0 | 0 | 0 | 0 | 0 |
| 10 | 4 | 3 | 3 | 2 | 2 | 2 | 2 |
| 11 | 3 | 3 | 3 | 2 | 1 | 1 | 1 |
| 12 | 1 | 1 | 4 | 3 | 3 | 3 | 3 |

Experimental Example 12. Experiments on Rats Receiving Treatments 24 h after the Onset of Stroke with Compound Ie of the Present Invention at an Initial Dosage of 5 μmol/Kg and 5 Subsequent Dosages of 2 μmol/Kg Each The efficacy was represented by neural function scores, and a lower score indicates a higher efficacy. A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incisions in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 24 h, compound Ie in normal saline (at an initial dosage of 5 μmol/kg, n=12) was infused through the tail vein. Then, infusion of compound Ie in normal saline (at a dosage of 2 μmol/kg, n=12) through rat tail vein was carried out once per day for 6 consecutive days, observed for 7 days. The rats were compared to themselves each day, and evaluated for the degree of damage in neural function by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Table 12.

The data in Table 12 demonstrated that efficacy was shown in rats that received treatment 24 h after the onset of stroke with one dose of 5 μmol/kg compound Ie on day 1 and one dose of 2 μmol/kg compound Ie per day for the following 5 days. Among the 12 rats that received the treatment, three were dead, while 8 out of the remaining 9 rats recovered to have no sign of loss in neural function, and one had only the sign of slight loss in neural function. Thus, continuous treatment with compound Ie showed therapeutic effect on stroke beyond the golden treatment window.

TABLE 12

Efficacy in rats receiving treatment with compound Ie of the present invention 24 h after the onset of stroke

| Rat No. | Daily neural function scores (Mean ± SD) | | | | | | |
|---|---|---|---|---|---|---|---|
| | Day 1 | Day 2 | Day 3 | Day 4 | Day 5 | Day 6 | Day 7 |
| 1 | 3 | 2 | 2 | 1 | 0 | 0 | 0 |
| 2 | 3 | 2 | 1 | 1 | 1 | 0 | 0 |
| 3 | 2 | 1 | 1 | 0 | 0 | 0 | 0 |
| 4 | 3 | 2 | 2 | 1 | 1 | 0 | 0 |
| 5 | 5 | | | | | | |
| 6 | 2 | 1 | 1 | 1 | 1 | 0 | 0 |
| 7 | 3 | 3 | 3 | 2 | 1 | 1 | 1 |
| 8 | 3 | 4 | 2 | 1 | 1 | 0 | 0 |
| 9 | 5 | | | | | | |
| 10 | 3 | 3 | 1 | 1 | 1 | 1 | 1 |
| 11 | 5 | 0 | 0 | 0 | 0 | 0 | 0 |
| 12 | 2 | 1 | 1 | 1 | 0 | 0 | 0 |

Experimental Example 13. Experiments on Rats Receiving Treatments with 6 Successive Administrations of 2 μmol/Kg Compound Ie of the Present Invention 6 h after the Onset of Stroke The efficacy was represented by neural function scores, and a lower score indicates a higher efficacy. A 10% chloral hydrate solution was injected intraperitoneally into male SD rats at a dosage of 400 mg/kg body weight for anesthesia. A longitudinal open incision was made at the center of the neck, and the right common carotid artery trunk was dissected (about 3 cm in length). Carotid external artery branches were each dissected and ligated at the hyoid level, and the carotid internal artery was dissected at the swollen part of the neck. The open incisions in the carotid internal artery and the proximal end of the common carotid artery were occluded respectively with noninvasive arterial clips, and the distal end of the carotid external artery was ligated. A catheter containing 0.5 mL thrombus suspension in normal saline was inserted in the carotid external artery trunk. At the same time when the clip on the carotid internal artery was released, the 0.5 mL thrombus suspension in normal saline in the catheter slowly flew from the carotid external artery to its proximal end, and then was injected into the arteries in brain through the carotid internal artery. Different from the previous experimental examples, the thrombus clots used in this experimental example was a remarkably solid thrombus suspension in normal saline prepared by using more aged thrombus having been stored at RT for 24 h, instead of the thrombus suspension in normal saline prepared by using thrombus stored at −24° C. Subsequently, the proximal end of the carotid artery was ligated, the arterial clips on the carotid internal artery and the common carotid artery were released, and blood flow was restored. After the wound was stitched up, 20,000 IU penicillin was intramuscularly injected for prevention from infection. After 6 h, compound Ie in normal saline (at an initial dosage of 5 μmol/kg, n=12) was infused through the tail vein. Then, infusion of compound Ie in normal saline (at a dosage of 2 μmol/kg, n=12) through rat tail vein was carried out once per day for 6 consecutive days, observed for 7 days. The rats were compared to themselves each day, and evaluated for the degree of damage in neural function by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The experimental results are shown in Table 13.

TABLE 13

Efficacy in rats receiving treatment with 2 μmol/kg compound Ie of the present invention 6 h after the onset of stroke

| Rat No. | Daily neural function scores (Mean ± SD) | | | | | | |
|---|---|---|---|---|---|---|---|
| | Day 1 | Day 2 | Day 3 | Day 4 | Day 5 | Day 6 | Day 7 |
| 1 | 4 | 3 | 2 | 1 | 1 | 1 | 1 |
| 2 | 3 | 2 | 1 | 1 | 0 | 0 | 0 |
| 3 | 3 | 3 | 3 | 3 | 1 | 1 | 1 |
| 4 | 3 | 3 | 1 | 1 | 1 | 1 | 1 |
| 5 | 5 | | | | | | |
| 6 | 3 | 3 | 1 | 1 | 1 | 1 | 1 |
| 7 | 5 | | | | | | |
| 8 | 3 | 3 | 1 | 1 | 1 | 1 | 1 |
| 9 | 5 | | | | | | |
| 10 | 5 | | | | | | |
| 11 | 5 | | | | | | |
| 12 | 3 | 5 | | | | | |

The data in Table 13 demonstrated that, in rat models 6 h after the onset of stroke induced by aged thrombus, efficacy was shown after 6 successive treatments with one dose of 2 μmol/kg compound Ie per day for 6 consecutive days. Among the 12 rats that received the treatment, six were dead, while 1 out of the remaining 6 rats recovered to have no sign of loss in neural function, and five had only the sign of slight loss in neural function. Thus, continuous treatment with compound Ie showed therapeutic effect on old stroke.

It should be noted that, because compounds Ia to Il except Ie in Experimental examples 1 to 7 achieved the effects in NO free radical scavenging, euglobulin colt lysis, thrombolysis, anti-thrombus action, and treatment in rats with stroke similar to those of compound Ie, the other compounds of Ia to Il may achieve the same therapeutic effects on old stroke as compound Ie did.

Experimental Example 14. Experiments on Nanostructures of Compounds Ia to Il of the Present Invention at a Concentration of $1\times10^{-6}$ M, $1\times10^{-9}$ M and $1\times10^{-12}$ M Compounds Ia to Il according to the present invention were prepared into $1\times10^{-6}$ M, $1\times10^{-9}$ M and $1\times10^{-12}$ M solutions, respectively. 10 μL solution was taken and dropped onto a copper grid with a filter paper placed underneath, air dried, and then observed under a transmission electronic microscope (TEM) (JEOL, JEM-1230). Photographs were taken so as to record the morphology and particle size.

Figure 25:
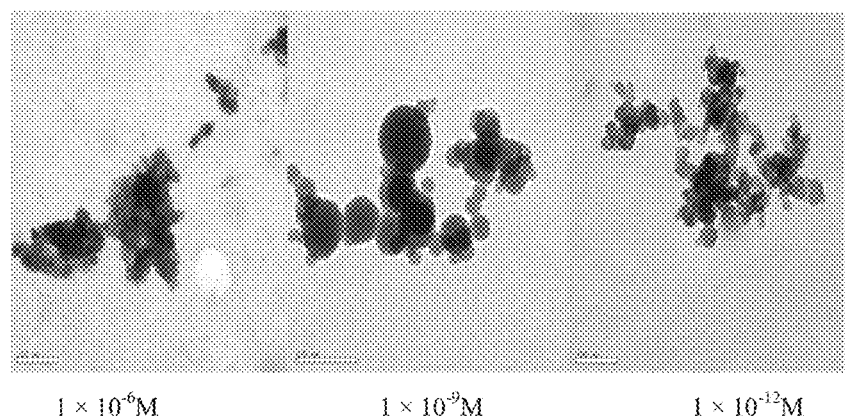
FIG. 25 shows the nanostructures of compound Ia according to the present invention in $1 \times 10^{-6}$ M, $1 \times 10^{-9}$ M and $1 \times 10^{-12}$ M aqueous solutions.
Figure 26:
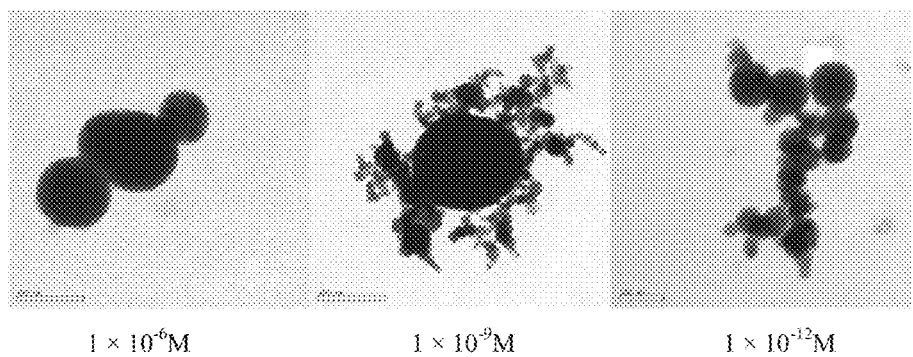
FIG. 26 shows the nanostructures of compound Ib according to the present invention in $1 \times 10^{-6}$ M, $1 \times 10^{-9}$ M and $1 \times 10^{-12}$ M aqueous solutions.
Figure 27:
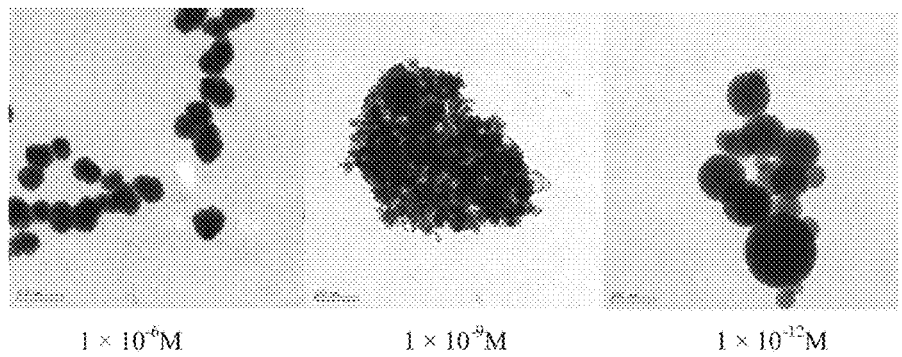
FIG. 27 shows the nanostructures of compound Ic according to the present invention in $1 \times 10^{-6}$ M, $1 \times 10^{-9}$ M and $1 \times 10^{-12}$ M aqueous solutions.
Figure 28:
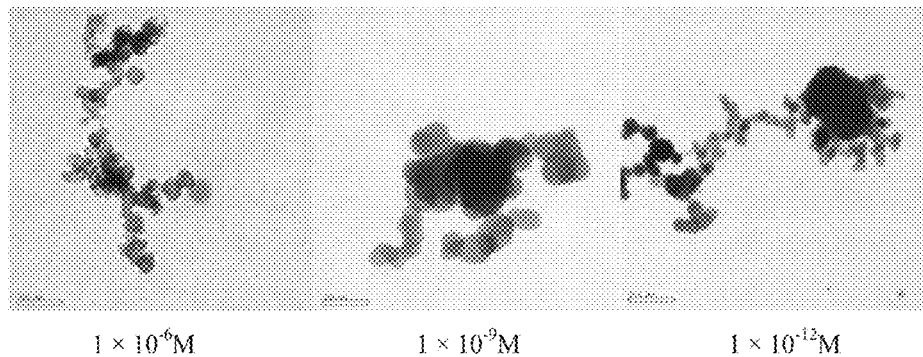
FIG. 28 shows the nanostructures of compound Id according to the present invention in $1 \times 10^{-6}$ M, $1 \times 10^{-9}$ M and $1 \times 10^{-12}$ M aqueous solutions.
Figure 29:
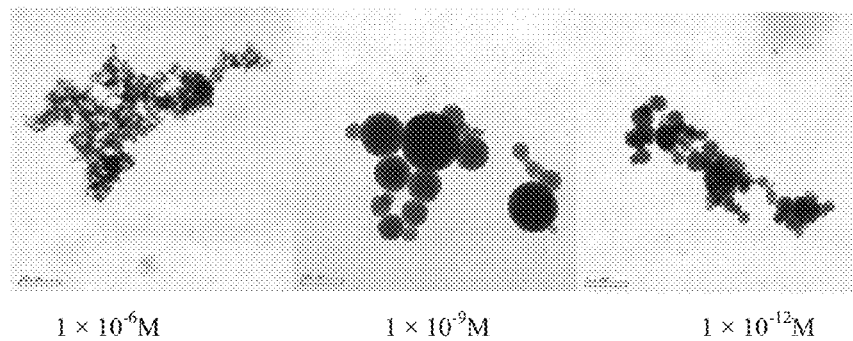
FIG. 29 shows the nanostructures of compound Ie according to the present invention in $1 \times 10^{-6}$ M, $1 \times 10^{-9}$ M and $1 \times 10^{-12}$ M aqueous solutions.
Figure 30:
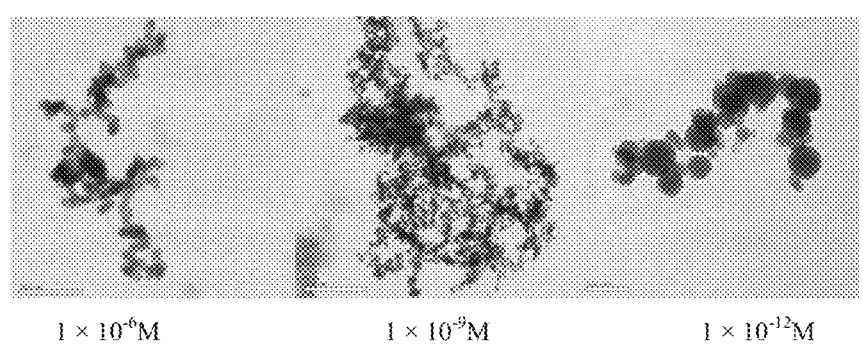
FIG. 30 shows the nanostructures of compound If according to the present invention in $1 \times 10^{-6}$ M, $1 \times 10^{-9}$ M and $1 \times 10^{-12}$ M aqueous solutions.
Figure 31:
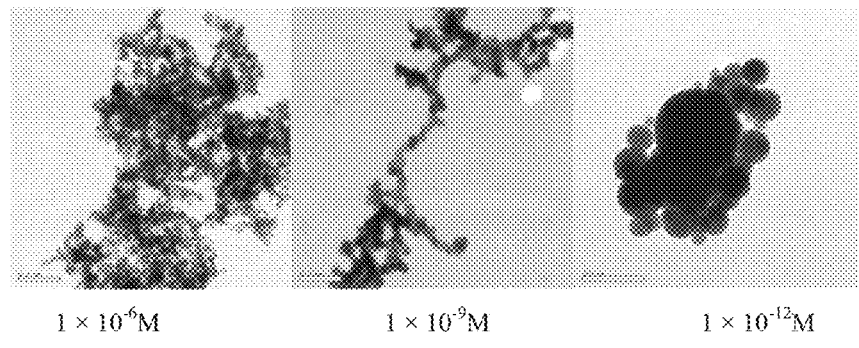
FIG. 31 shows the nanostructures of compound Ig according to the present invention in $1 \times 10^{-6}$ M, $1 \times 10^{-9}$ M and $1 \times 10^{-12}$ M aqueous solutions.
Figure 32:
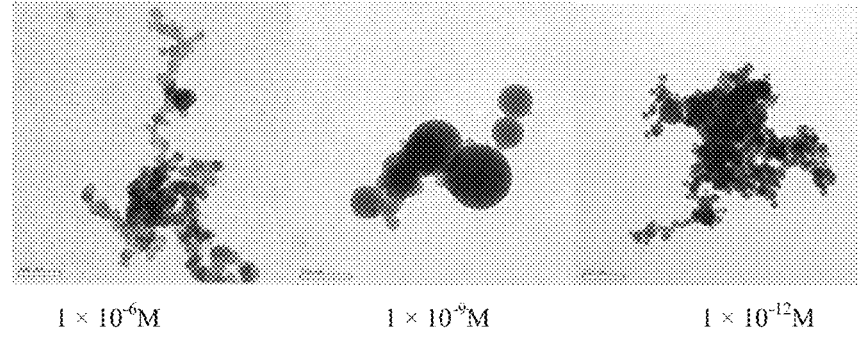
FIG. 32 shows the nanostructures of compound Ih according to the present invention in $1 \times 10^{-6}$ M, $1 \times 10^{-9}$ M and $1 \times 10^{-12}$ M aqueous solutions.
Figure 33:
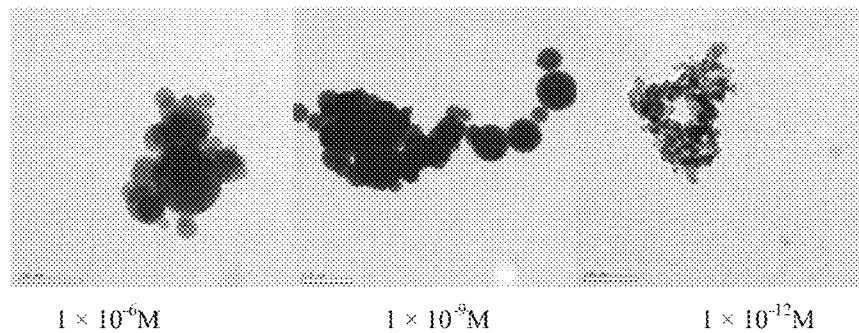
FIG. 33 shows the nanostructures of compound Ii according to the present invention in $1\times10^{-6}$ M, $1\times10^{-9}$ M and $1\times10^{-12}$ M aqueous solutions.
Figure 34:
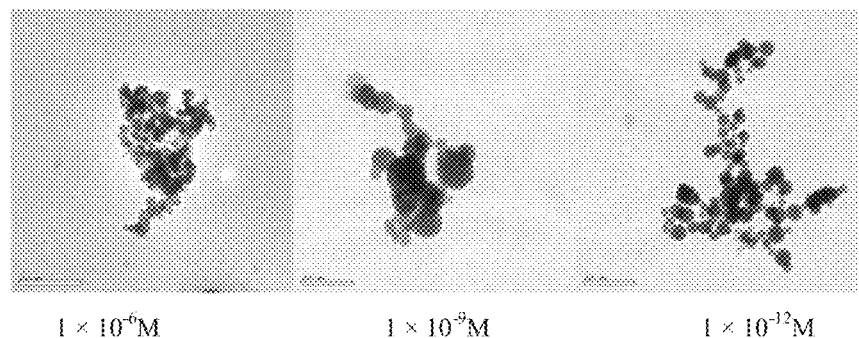
FIG. 34 shows the nanostructures of compound Ij according to the present invention in $1\times10^{-6}$ M, $1\times10^{-9}$ M and $1\times10^{-12}$ M aqueous solutions.
Figure 35:
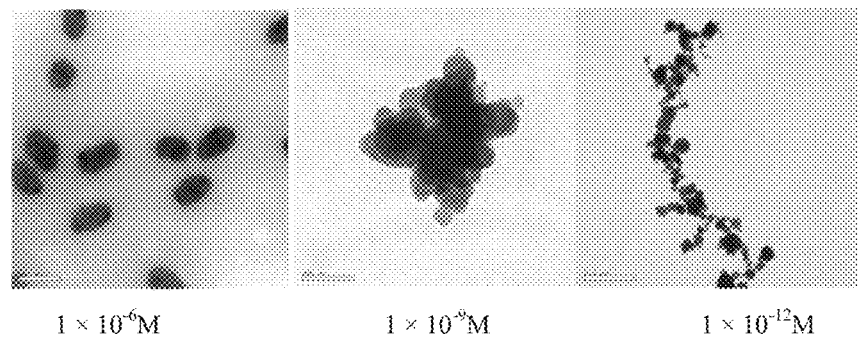
FIG. 35 shows the nanostructures of compound Ik according to the present invention in $1\times10^{-6}$ M, $1\times10^{-9}$ M and $1\times10^{-12}$ M aqueous solutions.
Figure 36:
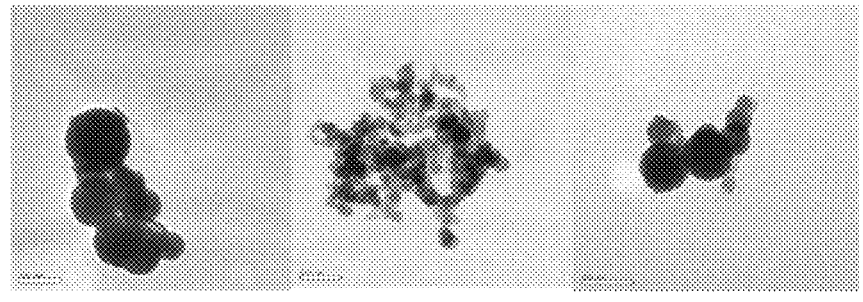
FIG. 36 shows the nanostructures of compound Il according to the present invention in $1\times10^{-6}$ M, $1\times10^{-9}$ M and $1\times10^{-12}$ M aqueous solutions.

1. Test compound: compounds Ia to Il of the present invention
2. Test method: the test compound (Ia to Il) was prepared into $1\times10^{-6}$ M, $1\times10^{-9}$ M and $1\times10^{-12}$ M solutions with triple-distilled water, respectively. A small amount (about 10 μl) was taken and dropped onto the surface of a copper grid with a filter paper placed underneath, air dried, and were then observed under TEM (JEOL, JEM-1230) for the morphology and particle size which were recorded in photographs.
3. Test results: results are shown in FIGS. 25 to 36. FIG. 25 shows the nanostructures of compound Ia according to the present invention in $1\times10^{-6}$ M, $1\times10^{-9}$ M and $1\times10^{-12}$ M aqueous solutions, and the nanostructures of Ia in the aqueous solutions are nanospheres having a diameter of 3.1 to 86.1 nm; FIG. 26 shows the nanostructures of compound Ib according to the present invention in $1\times10^{-6}$ M, $1\times10^{-9}$ M and $1\times10^{-12}$ M aqueous solutions, and the nanostructures of Ib in the aqueous solutions are nanospheres having a diameter of 4.3 to 297.9 nm; FIG. 27 shows the nanostructures of compound Ic according to the present invention in $1\times10^{-6}$ M, $1\times10^{-9}$ M and $1\times10^{-12}$ M aqueous solutions, and the nanostructures of Ic in the aqueous solutions are nanospheres having a diameter of 2.2 to 165.7 nm; FIG. 28 shows the nanostructures of compound Id according to the present invention in $1\times10^{-6}$ M, $1\times10^{-9}$ M and $1\times10^{-12}$ M aqueous solutions, and the nanostructures of Id in the aqueous solutions are nanospheres having a diameter of 16.2 to 201.2 nm; FIG. 29 shows the nanostructures of compound Ie according to the present invention in $1\times10^{-6}$ M, $1\times10^{-9}$ M and $1\times10^{-12}$ M aqueous solutions, and the nanostructures of Ie in the aqueous solutions are nanospheres having a diameter of 3.3 to 138.9 nm; FIG. 30 shows the nanostructures of compound If according to the present invention in $1\times10^{-6}$ M, $1\times10^{-9}$ M and $1\times10^{-12}$ M aqueous solutions, and the nanostructures of If in the aqueous solutions are nanospheres having a diameter of 3.6 to 82.4 nm; FIG. 31 shows the nanostructures of compound Ig according to the present invention in $1\times10^{-6}$ M, $1\times10^{-9}$ M and $1\times10^{-12}$ M aqueous solutions, and the nanostructures of Ig in the aqueous solutions are nanospheres having a diameter of 6.3 to 264.5 nm; FIG. 32 shows the nanostructures of compound Ih according to the present invention in $1\times10^{-6}$ M, $1\times10^{-9}$ M and $1\times10^{-12}$ M aqueous solutions, and the nanostructures of Ih in the aqueous solutions are nanospheres having a diameter of 5.1 to 149.8 nm; FIG. 33 shows the nanostructures of compound Ii according to the present invention in $1\times10^{-6}$ M, $1\times10^{-9}$ M and $1\times10^{-12}$ M aqueous solutions, and the nanostructures of Ii in the aqueous solutions are nanospheres having a diameter of 4.7 to 107.7 nm; FIG. 34 shows the nanostructures of compound Ij according to the present invention in $1\times10^{-6}$ M, $1\times10^{-9}$ M and $1\times10^{-12}$ M aqueous solutions, and the nanostructures of Ij in the aqueous solutions are nanospheres having a diameter of 9.1 to 73.7 nm; FIG. 35 shows the nanostructures of compound Ik according to the present invention in $1\times10^{-6}$ M, $1\times10^{-9}$ M and $1\times10^{-12}$ M aqueous solutions, and the nanostructures of Ik in the aqueous solutions are nanospheres having a diameter of 10.1 to 66.7 nm; FIG. 36 shows the nanostructures of compound Il according to the present invention in $1\times10^{-6}$ M, $1\times10^{-9}$ M and 1×10$^{-12}$ M aqueous solutions, and the nanostructures of Il in the aqueous solutions are nanospheres having a diameter of 6.1 to 153.3 nm.

Experimental Example 15. High Resolution FT-MS Experiments of Compounds Ia to Il of the Present Invention at Concentrations of 1×10$^{-6}$ M, 1×10$^{-9}$ M and 1×10$^{-12}$ M Compounds Ia to Il were prepared into a 12.5 μM solution with triple-distilled water, and a 10 μL sample was loaded onto a solariX FT-ICR mass spectroscopy (Bruker Daltonik). Intermolecular association status was observed and data was acquired. The results are listed in Table 14 to 16.

TABLE 14

High resolution FT-MS data of dimers formed by compounds Ia-Il of the present invention at three different concentrations

| Compounds | Concentration | | |
|---|---|---|---|
| | 1 × 10$^{-6}$M/dimer | 1 × 10$^{-9}$M/dimer | 1 × 10$^{-12}$M/dimer |
| Ia | 2748.4580 | 2748.4580 | 2748.4580 |
| Ib | 2772.5308 | 2772.5308 | 2772.5308 |
| Ic | 2888.5308 | 2888.5308 | 2888.5308 |
| Id | 2720.4266 | 2720.4266 | 2720.4266 |
| Ie | 2744.4994 | 2744.4994 | 2744.4994 |
| If | 2840.4994 | 2840.4994 | 2840.4994 |
| Ig | 2606.3838 | 2606.3838 | 2606.3838 |
| Ih | 2630.4564 | 2630.4564 | 2630.4564 |
| Ii | 2726.4564 | 2726.4564 | 2726.4564 |
| Ij | 2294.1814 | 2294.1814 | 2294.1814 |
| Ik | 2318.2542 | 2318.2542 | 2318.2542 |
| Il | 2414.2542 | 2414.2542 | 2414.2542 |

TABLE 15

High resolution FT-MS data of trimers formed by compounds Ia-Il of the present invention at three different concentrations

| Compounds | Concentration | | |
|---|---|---|---|
| | 1 × 10$^{-6}$M/trimer | 1 × 10$^{-9}$M/trimer | 1 × 10$^{-12}$M/trimer |
| Ia | 4122.1870 | 4122.1870 | 4122.1870 |
| Ib | 4158.2962 | 4158.2962 | 4158.2962 |
| Ic | 4332.2962 | 4332.2962 | 4332.2962 |
| Id | 4080.1399 | 4080.1399 | 4080.1399 |
| Ie | 4116.2491 | 4116.2491 | 4116.2491 |
| If | 4260.2491 | 4260.2491 | 4260.2491 |
| Ig | 3909.0757 | 3909.0757 | 3909.0757 |
| Ih | 3945.1846 | 3945.1846 | 3945.1846 |
| Ii | 4089.1846 | 4089.1846 | 4089.1846 |
| Ij | 3440.7721 | 3440.7721 | 3440.7721 |
| Ik | 3476.8813 | 3476.8813 | 3476.8813 |
| Il | 3620.8813 | 3620.8813 | 3620.8813 |

TABLE 16

High resolution FT-MS data of tetramers formed by compounds Ia-Il of the present invention at three different concentrations

| Compounds | Concentration | | |
|---|---|---|---|
| | 1 ×10$^{-6}$M/ tetramer | 1 × 10$^{-9}$M/ tetramer | 1 × 10$^{-12}$M/ tetramer |
| Ia | 5495.9160 | 5495.9160 | 5495.9160 |
| Ib | 5544.0616 | 5544.0616 | 5544.0616 |
| Ic | 5776.0616 | 5776.0616 | 5776.0616 |
| Id | 5439.8532 | 5439.8532 | 5439.8532 |
| Ie | 5487.9988 | 5487.9988 | 5487.9988 |
| If | 5679.9976 | 5679.9976 | 5679.9976 |
| Ig | 5211.7676 | 5211.7676 | 5211.7676 |
| Ih | 5259.9128 | 5259.9128 | 5259.9128 |
| Ii | 5451.9128 | 5451.9128 | 5451.9128 |
| Ij | 4587.3628 | 4587.3628 | 4587.3628 |
| Ik | 4635.5084 | 4635.5084 | 4635.5084 |
| Il | 4827.5084 | 4827.5084 | 4827.5084 |

Table 14 to 16 show the precise mass numbers measured by FT High resolution MS. These mass numbers indicate that dimers, trimers, and tetramers were all detected at three different concentrations of compounds Ia-Il of the present invention. Therefore, the compounds according to the present invention can form dimers, trimers and tetramers in an aqueous solution at the same time.

Figure 37:
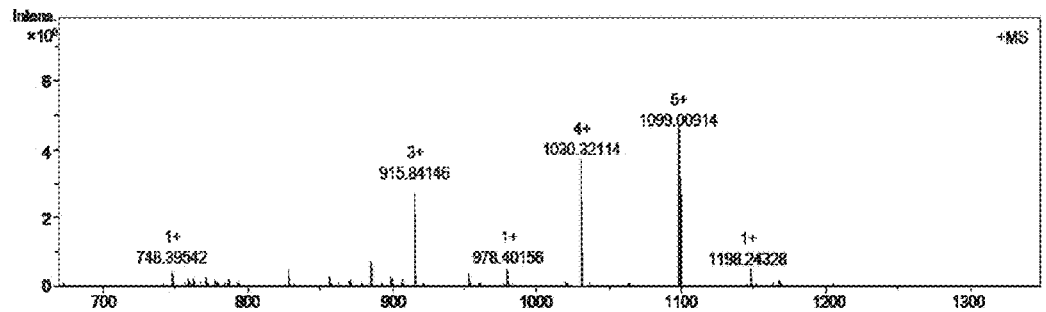
FIG. 37 shows the high-resolution FT-MS spectrum of compound Ie according to the present invention at a concentration of 0.01 μM.
Figure 38:
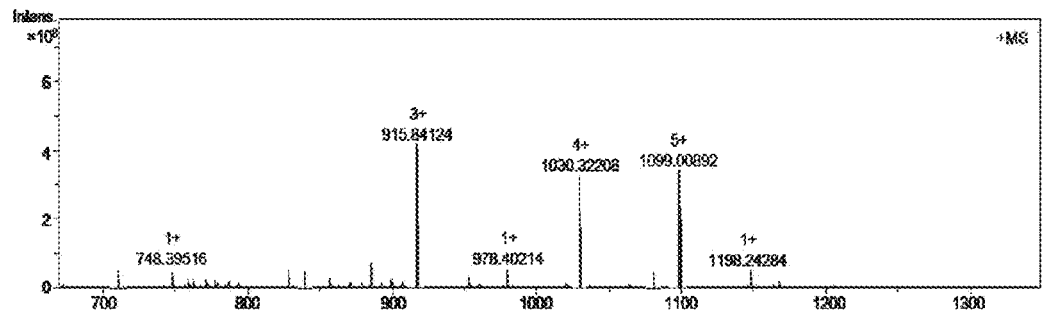
FIG. 38 shows the high-resolution FT-MS spectrum of compound Ie according to the present invention at a concentration of 0.1 μM.
Figure 39:
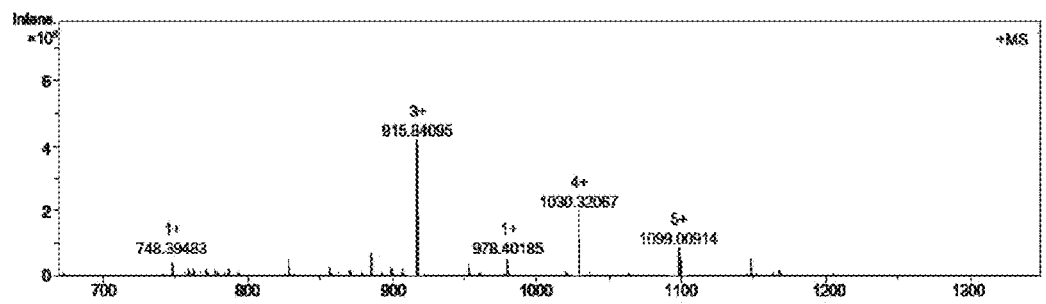
FIG. 39 shows the high-resolution FT-MS spectrum of compound Ie according to the present invention at a concentration of 1 μM.
Figure 40:
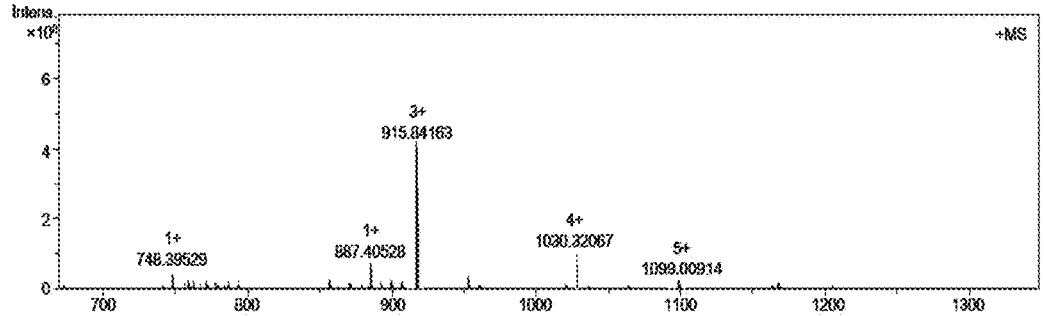
FIG. 40 shows the high-resolution FT-MS spectrum of compound Ie according to the present invention at a concentration of 10 μM.

Experimental Example 16. High Resolution FT-MS Experiments of Compound Ie of the Present Invention at Concentrations of 10.0 μM, 1.0 μM, 0.1 μM and 0.01 μM For MS visualization, Compounds Ie was prepared into 10.0 μM, 1.0 μM, 0.1 μM and 0.01 μM solutions with triple-distilled water, and a 10 μL sample was loaded onto a solariX FT-ICR mass spectroscopy (Bruker Daltonik). Intermolecular association status was observed and data was acquired. The results are shown in FIGS. 37 to 40. FIG. 37 is the high-resolution FT-MS spectrum of compound Ie according to the present invention at a concentration of 0.01 μM: 915.84146 is the triple-charged ion of the dimer, 1030.32114 is the quadruple-charged ion of the trimer, and 1099.00914 is the quintuple-charged ion of the tetramer; FIG. 38 is the high-resolution FT-MS spectrum of compound Ie according to the present invention at a concentration of 0.1 μM: 915.84124 is the triple-charged ion of the dimer, 1030.32208 is the quadruple-charged ion of the trimer, and 1099.00829 is the quintuple-charged ion of the tetramer; FIG. 39 is the high-resolution FT-MS spectrum of compound Ie according to the present invention at a concentration of 1 μM: 915.84095 is the triple-charged ion of the dimer, 1030.32067 is the quadruple-charged ion of the trimer, and 1099.00914 is the quintuple-charged ion of the tetramer; FIG. 40 is the high-resolution FT-MS spectrum of compound Ie according to the present invention at a concentration of 10 μM: 915.84163 is the triple-charged ion of the dimer, 1030.32067 is the quadruple-charged ion of the trimer, and 1099.00914 is the quintuple-charged ion of the tetramer.

The dimers, trimers and tetramers formed by the compounds of the present invention further assembled into nanospheres having a diameter of 2 to 300 nm. Among nanospheres of such sizes, nanospheres having a diameter less than 100 nm was over 99%. It is a well known fact in nanopharmacology that nanospheres having a diameter of less than 100 nm are unlikely to be engulfed by macrophages during transportation in blood and may readily cross the capillary wall. These properties allow the compounds according to the present invention to cross the blood-brain barrier. It is the property of crossing the blood-brain barrier of the compounds according to the present invention that enables the metabolic products of the compounds according to the present invention to be detectable in brain tissues in rats receiving treatment of stroke.

Experimental Example 17. Experiments on High-Resolution FT-MS Monitoring the Metabolic Products in Brain Tissues in Rats Treated with Compound Ie According to the Present Invention The entire rat brain was taken out and placed into a 50 mL centrifuge tube, into which 10 mL 0.9% NaCl was added, and homogenized to obtain a uniform suspension which was then centrifuged at 3000 rpm for 10 min. 5 mL supernatant was added into 10 mL methanol and evenly mixed by shaking, and centrifuged at 3000 rpm for 10 min. The supernatant was concentrated under reduced pressure until dry, followed by addition of 1 mL methanol, and again centrifuged at 12000 rpm for 10 min. The resultant supernatant was used for monitoring of the content of metabolic products in brain tissues in rats treated with compound Ie.

High-resolution FT-MS experimental results showed two metabolic products M1 and M2 in the brain. Among them, M1 had a $[M+1]^+$ of 291.06971 and a molecular formula of $C_{15}H_{19}O_5N_2$; and M2 had a $[M+1]^+$ of 307.04350 and a molecular formula of $C_{15}H_{19}O_4N_2$. (MS conditions: loading: 10 μL; ionization mode: ES+; cone voltage: 30 V; mobile phase flow rate: 0.2 mL/min). According to the above data, the metabolic products M1 and M2 were assumed as the following compounds:

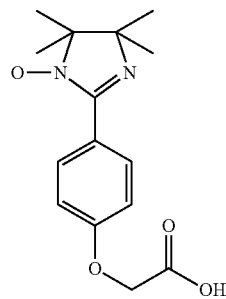 [SMILES: CC1(C)N=C(c2ccc(OCC(=O)O)cc2)N(O)C1(C)C]

M1

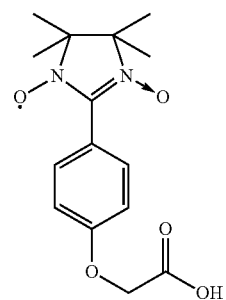

M2

|  | M1 | M2 |
|---|---|---|
| Theoretical MW | 291.1345 | 307.1249 |
| Measured MW | 291.0697 | 307.0435 |

This demonstrated that the compound Ie of the present invention did indeed cross the blood-brain barrier, enabling the effect of NO free radical scavenging, thrombolysis and the anti-thrombus effect in brain.

What is claimed is:

1. A ternary conjugate having the following formula Ie:

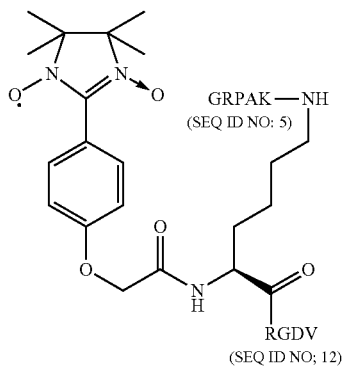

Ie

2. A pharmaceutical composition comprising the ternary conjugate according to claim 1 and a pharmaceutically acceptable carrier.

3. The pharmaceutical composition according to claim 2, wherein the ternary conjugate is in the form of a nanospherical structure.

4. A method of treating stroke or cerebral infarction, the method comprises administering to a subject in need thereof an effective amount of the ternary conjugate of claim 1.

5. The method of claim 4, wherein the ternary conjugate is administered after three hours from an onset of symptoms.

6. A method for performing thrombolysis, NO free radical scavenging, or antithrombotic therapy in a subject, the method comprises administering to a subject in need thereof an effective amount of the ternary conjugate of claim 1.

* * * * *